US010982285B2

(12) United States Patent
Freedman et al.

(10) Patent No.: US 10,982,285 B2
(45) Date of Patent: Apr. 20, 2021

(54) BIOMARKERS FOR THE IDENTIFICATION OF PROSTATE CANCER AND METHODS OF USE

(71) Applicants: Duke University, Durham, NC (US); George Washington University, Washington, DC (US)

(72) Inventors: Jennifer Freedman, Durham, NC (US); Yanru Wang, Durham, NC (US); Hongliang Liu, Durham, NC (US); Qingyi Wei, Durham, NC (US); Daniel George, Durham, NC (US); Steven Patierno, Durham, NC (US); Bi-Dar Wang, Potomac, MD (US); Norman Lee, Dayton, MD (US)

(73) Assignees: DUKE UNIVERSITY, Durham, NC (US); THE GEORGE WASHINGTON UNIVERSITY, Washington, DC (US)

( * ) Notice: Subject to any disclaimer, the term of this patent is extended or adjusted under 35 U.S.C. 154(b) by 495 days.

(21) Appl. No.: 15/344,222

(22) Filed: Nov. 4, 2016

(65) Prior Publication Data

US 2017/0166977 A1    Jun. 15, 2017

Related U.S. Application Data

(60) Provisional application No. 62/250,723, filed on Nov. 4, 2015, provisional application No. 62/393,293, filed on Sep. 12, 2016.

(51) Int. Cl.
| | |
|---|---|
| *C12Q 1/68* | (2018.01) |
| *C12P 19/34* | (2006.01) |
| *C12Q 1/6886* | (2018.01) |
| *A61K 38/22* | (2006.01) |

(52) U.S. Cl.
CPC ........... *C12Q 1/6886* (2013.01); *A61K 38/22* (2013.01); *C12Q 2600/106* (2013.01); *C12Q 2600/118* (2013.01); *C12Q 2600/156* (2013.01)

(58) Field of Classification Search
CPC ........... C12Q 1/6886; C12Q 2600/106; C12Q 2600/118; C12Q 2600/156
See application file for complete search history.

(56) References Cited

PUBLICATIONS

Robin Dong-Woo Lee et al, Large-scale profiling and identification of potential regulatory mechanisms for allelic gene expression in colorectal cancer cells. Gene 512 (2013) 16-22 (Year: 2013).*
Joelle Michaud et al, Isolation and Characterization of a Human Chromosome 21q22.3 Gene (WDR4) and Its Mouse Homologue That Code for a WD-Repeat Protein. Genomics 68, 71-79 (2000) (Year: 2000).*
Reference SNP (refSNP) Cluster Report: rs2248490, pp. 1-5, printed on Apr. 4, 2019, from www.ncbi.nlm.nih.gov/projects/SNP (Year: 2019).*
Reference SNP (refSNP) Cluster Report: rs11911090 from www.ncbi.nlm.nih.gov, printed pp. 1-4 on Dec. 12, 2019. (Year: 2019).*
Reference SNP (refSNP) Cluster Report: rs15736 from www.ncbi.nlm.nih.gov, printed pp. 1-5 on Dec. 12, 2019. (Year: 2019).*
Submitted SNP(ss) Report NCBI Assay Id(ss#): ss160521731, Aug. 4, 2009, 1 printed page from www.ncbi.nlm.nih.gov (Year: 2009).*
Submitted SNP(ss) Report NCBI Assay Id(ss#): ss160375355, Aug. 4, 2009, 2 printed pages from www.ncbi.nlm.nih.gov (Year: 2009).*
Submitted SNP(ss) Report NCBI Assay Id(ss#): ss160016501, Aug. 4, 2009, 1 printed page from www.ncbi.nlm.nih.gov (Year: 2009).*
Tindall, E.A. et al, Clinical Presentation of Prostate Cancer in Black South Africans, The Prostate 74:880-891, Published online Apr. 9, 2014 (Year: 2014).*
1000 Genomes Project Consortium, An Integrated Map of Genetic Variation from 1,092 Human Genomes, Nature, 2012, 491:56-65.
Akaike, A New Look at the Statistical Model Identification, IEEE Transactions on Automatic Control, 1974, 19(6):716-723.
Al Olama, et al., A Meta-Analysis of Genome-Wide Association Studies to Identify Prostate Cancer Susceptibility Loci Associated with Aggressive and Non-Aggressive Disease, Human Molecular Genetics, 2013, 22(2):408-415.
Al Olama, et al., A Meta-Analysis of 87,040 Individuals Identifies 23 New Susceptibility Loci for Prostate Cancer, Nat. Genet., 2014, 46(10):1103-1109.
Al Olama, et al., Risk Analysis of Prostate Cancer in PRACTICAL, a Multinational Consortium, Using 25 Known Prostate Cancer Susceptibility Loci, Cancer Epidemiology, Biomarkers & Prevention, 2015, 24(7):1121-1129.
Anastas, et al., WNT Signalling Pathways as Therapeutic Targets in Cancer, Nature Reviews Cancer, 2013, 13:11-26.
Andriole, et al., Prostate Cancer Screening in the Randomized Prostate, Lung, Colorectal, and Ovarian Cancer Screening Trial: Mortality Results After 13 Years of Follow-Up, J. Natl. Cancer Inst.,. 2012, 104:125-132.
Aulchenko, et al., GenABEL: An R Library for Genome-Wide Association Analysis, Bioinformatics, 2007, 23(10):1294-1296.
Beck, et al., Unravelling Cancer Stem Cell Potential, Nature Reviews Cancer, 2013, 13:727-738.
Benjamini, et al., Controlling the False Discovery Rate in Behavior Genetics Research, Behavioural Brain Research, 2001, 125:279-284.
Berndt, et al., Two Susceptibility Loci Identified for Prostate Cancer Aggressiveness, Nature Communications, 2015, 6:6889, 7 pages.
Bijnsdorp, et al., Exosomal ITGA3 Interferes With Non-Cancerous Prostate Cell Functions and is Increased in Urine Exosomes of Metastatic Prostate Cancer Patients, Journal of Extracellular Vesicles, 2013, 2:22097, 10 pages.
Bonuccelli, et al., The Milk Protein a-casein Functions as a Tumor Suppressor Via Activation of STAT1 Signaling, Effectively Preventing Breast Cancer Tumor Growth and Metastasis, Cell Cycle, 2012, 11(21):3972-3982.

(Continued)

*Primary Examiner* — Stephen T Kapushoc
(74) *Attorney, Agent, or Firm* — Quarles & Brady LLP

(57) ABSTRACT

The present disclosure provides biomarkers for the identification of prostate cancer and methods of use. The present disclosure also provide biomarkers that can be used for determining risk of developing prostate cancer, aggressiveness of prostate cancer and survival rate for subpopulations of African American males or non-Hispanic white males.

11 Claims, 17 Drawing Sheets
(15 of 17 Drawing Sheet(s) Filed in Color)

(56) References Cited

PUBLICATIONS

Borque, et al., Genetic Predisposition to Early Recurrence in Clinically Localized Prostate Cancer, BJU International, 2013, 111(4):549-558.
Bostrom, et al., Genomic Predictors of Outcome in Prostate Cancer, European Urology, 2015, 68:1033-1044.
Boyle, et al., Annotation of Functional Variation in Personal Genomes Using RegulomeDB, Genome Research, 2012, 22:1790-1797.
Broustas, et al., RAD9 Enhances Radioresistance of Human Prostate Cancer Cells Through Regulation of ITGB1 Protein Levels, Prostate, 2014, 74(14):1359-1370.
Candi, et al., TAp63 and Np63 in Cancer and Epidermal Development, Cell Cycle, 2007, 6(3):274-285.
Chambless, et al., Estimation of Time-Dependent Area Under the ROC Curve for Long-Term Risk Prediction, Statistics in Medicine, 2006, 25(20):3474-3486.
Chang, et al., Validation of Genome-Wide Prostate Cancer Associations in Men of African Descent, Cancer Epidemiology, Biomarkers & Prevention, 2011, 20(1):23-32.
Choudhury, et al., The Role of Genetic Markers in the Management of Prostate Cancer, European Urology, 2012, 62:577-587.
Ciardiello, et al., EGFR Antagonists in Cancer Treatment, New England Journal of Medicine, 2008, 358(1):1160-1174.
Clark, et al., The RNA Helicase p68 Is a Novel Androgen Receptor Coactivator Involved in Splicing and Is Overexpressed in Prostate Cancer, Cancer Research, 2008, 68(19):7938-7946.
Collins, et al., Identification and Isolation of Human Prostate Epithelial Stem Cells Based on a2B1-Integrin Expression, Journal of Cell Science, 2001, 114:3865-3872.
Collins, et al., Prospective Identification of Tumorigenic Prostate Cancer Stem Cells, Cancer Research, 2005, 65(23):10946-10951.
Cook, et al., A Genome-Wide Association Study of Prostate Cancer in West African Men, Hum. Genet., 2014, 133(5):509-521.
Crook, et al., Prognostic Factors for Newly Diagnosed Prostate Cancer and Their Role in Treatment Selection, Seminars in Radiation Oncology, 2013, 23(3):165-172.
Encode Project Consortium, An Integrated Encyclopedia of DNA Elements in the Human Genome, Nature, 2012, 489:57-74.
Ferlay, et al., Cancer Incidence and Mortality Worldwide: Sources, Methods and Major Patterns in GLOBOCAN 2012, International Journal of Cancer, 2014, 136:E359-E386.
Fletcher, et al., ABC Transporters in Cancer: More Than Just Drug Efflux Pumps, Nature Reviews Cancer, 2010, 10:147-156.
Frampton, et al., Activation of MET Via Diverse Exon 14 Splicing Alterations Occurs in Multiple Tumor Types and Confers Clinical Sensitivity to MET Inhibitors, Cancer Discovery, 2015, 5(8):1-10.
Goldstein, et al., Trop2 Identifies a Subpopulation of Murine and Human Prostate Basal Cells With Stem Cell Characteristics, PNAS, 2008, 105(52):20882-20887.
Haiman, et al., Characterizing Genetic Risk at Known Prostate Cancer Susceptibility Loci in African Americans, PLoS Genetics, 2011, 7(5):e1001387, 10 pages.
Haiman, et al., Genome-Wide Association Study of Prostate Cancer in Men of African Ancestry Identifies a Susceptibility Locus at 17q21, Nat. Genet., 2011, 43(6):570-573.
Hao, et al., In Vitro and In Vivo Prostate Cancer Metastasis and Chemoresistance Can Be Modulated by Expression of Either CD44 or CD147, PLoS One, 2012, 7(8):e40716, 14 pages.
Hayes, et al., Macrophage Inhibitory Cytokine-1 H6D Polymorphism, Prostate Cancer Risk, and Survival, Cancer Epidemiol. Biomarkers Prev., 2006, 15(6):1223-1225.
Higgins, et al., Quantifying Heterogeneity in a Meta-Analysis, Statistics in Medicine, 2002, 21:1539-1558.
Howie, et al., A Flexible and Accurate Genotype Imputation Method for the Next Generation of Genome-Wide Association Studies, PLoS Genetics, 2009, 5(6):e1000529, 15 pages.
Hu, et al., A Genome-Wide Association Study Identifies Two New Lung Cancer Susceptibility Loci at 13q12.12 and 22q12.2 in Han Chinese, Nature Genetics, 2011, 43(8):792-796.
Hurt, et al., CD44+ CD24-Prostate Cells are Early Cancer Progenitor/Stem Cells That Provide a Model for Patients With Poor Prognosis, British Journal of Cancer, 2008, 98:756-765.
Jeffers, et al., Activating Mutations for the Met Tyrosine Kinase Receptor in Human Cancer, Proc. Natl. Acad. Sci. USA, 1997, 94:11445-11450.
Jiao, et al., Identification of CD166 as a Surface Marker for Enriching Prostate Stem/Progenitor and Cancer Initiating Cells, PLoS One, 2012, 7(8):e42564, 14 pages.
Jorde, et al., Genetic Variation, Classification and 'Race', Nature Genetics Supplement, 2004, 36(11):S28-S33.
Karatas, et al., The Role of ATP-Binding Cassette Transporter Genes in the Progression of Prostate Cancer, Prostate, 2016, 76(5):434-444.
Kiemeney, et al., Sequence Variant on 8q24 Confers Susceptibility to Urinary Bladder Cancer, Nature Genetics, 2008, 40(11):1307-1312.
Kim, et al., Genetic Variants at 1q32.1, 10q11.2 and 19q13.41 are Associated With Prostate-Specific Antigen for Prostate Cancer Screening in Two Korean Population-Based Cohort Studies, Gene, 2015, 556(2):199-205.
Knipe, et al., Genetic Variation in Prostate-Specific Antigen-Detected Prostate Cancer and the Effect of Control Selection on Genetic Association Studies, Cancer Epidemiology, Biomarkers & Prevention, 2014, 23(7):1356-1365.
Kolonel, et al., A Multiethnic Cohort in Hawaii and Los Angeles: Baseline Characteristics, American Journal of Epidemiology, 2000, 151(4):346-357.
Kolonel, et al., The Multiethnic Cohort Study: Exploring Genes, Lifestyle and Cancer Risk, Nature Reviews Cancer, 2004, 4:1-9.
Kornblihtt, et al., Alternative Splicing: A Pivotal Step Between Eukaryotic Transcription and Translation, Nature Reviews Molecular Cell Biology, 2013, 14(3):153, 13 pages.
Kurozumi, et al., Tumor-Suppressive microRNA-223 Inhibits Cancer Cell Migration and Invasion by Targeting ITGA3/ITGB1 Signaling in Prostate Cancer, Cancer Science, 2016, 107(1):84-94.
Kyjacova, et al, Radiotherapy-Induced Plasticity of Prostate Cancer Mobilizes Stem-Like Non-Adherent, Erk Signaling-Dependent Cells, Cell Death and Differentiation, 2015, 22:898-911.
Lange, et al., Genome-Wide Association Scan for Variants Associated with Early-Onset Prostate Cancer, PLoS One, 2014, 9(4):e93436, 8 pages.
Lappalainen, et al., Transcriptome and genome Sequencing Uncovers Functional Variation in Humans, Nature, 2013, 501(7468):506-511.
Lichtenstein, et al., Environmental and Heritable Factors in the Causation of Cancer, New England Journal of Medicine, 2000, 343(2):78-85.
Lilja, et al., Prostate-Specific Antigen and Prostate Cancer: Prediction, Detection and Monitoring, Nature Reviews Cancer, 2008, 8:268-278.
Lin, et al., SNP-SNP Interaction Network in Angiogenesis Genes Associated with Prostate Cancer Aggressiveness, PLoS One, 2013, 8(4):e59688, 9 pages.
Liu, et al., NOTCH1 Signaling Promotes Chemoresistance Via Regulating ABCC1 Expression in Prostate Cancer Stem Cells, Molecular and Cellular Biochemistry, 2014, 393(1-2):265-270.
Mamat, et al., Transcriptional Regulation of Aldehyde Dehydrogenase I A I Gene by Alternative Spliced Forms of Nuclear Factor Y in Tumorigenic Population of Endometrial Adenocarcinoma, Genes & Cancer, 2011, 2(10)979-984.
Mancuso, et al., The Contribution of Rare Variation to Prostate Cancer Heritability, Nature Genetics, 2016, 48:30-35.
Marcato, et al., Aldehyde Dehydrogenase—Its Role as a Cancer Stem Cell Marker Comes Down to the Specific Isoform, Cell Cycle, 2011, 10(9):1378-1384.
Medema, Cancer Stem Cells: The Challenges Ahead, Nature Cell Biology, 2013, 15:338-344.
Mimeault, et al., Frequent Gene Products and Molecular Pathways Altered in Prostate Cancer- and Metastasis-Initiating Cells and Their Progenies and Novel Promising Multitargeted Therapies, Mol. Med., 2011, 17(9-10):949-964.

(56) References Cited

PUBLICATIONS

National Cancer Institute, Cancer Statistics Review, 1975-2013—Previous Version—SEER Cancer Statistics Review, https://seer.cancer.gov/archive/csr/1975_2013/, 2013.

National Cancer Institute, Cancer Stat Facts: Prostate Cancer, https://seer.cancer.gov/statfacts/html/prost.html, 2018.

National Comprehensive Cancer Network: Prostate Cancer—Version 2.2016, https://www.nccn.org/store/login/login.aspx?ReturnURL=https://www.nccn.org/professionals/physician_gls/pdf/prostate.pdf, 2016.

Oken, et al., Baseline Chest Radiograph for Lung Cancer Detection in the Randomized Prostate, Lung, Colorectal and Ovarian Cancer Screening Trial, Journal of the National Cancer Institute, 2005, 97(24):1832-1839.

Paradowska, et al., Aberrant Epigenetic Modifications in the CTCF Binding Domain of the IGF2/H19 Gene in Prostate Cancer Compared with Benign Prostate Hyperplasia, International Journal of Oncology, 2009, 35:87-96.

Peraldo-Neia, et al., Epidermal Growth Factor Receptor (EGFR) Mutation Analysis, Gene Expression Profiling and EGFR Protein Expression in Primary Prostate Cancer, BMC Cancer, 2011, 11:31, 12 pages.

Pignon, et al., p63-expressing Cells are the Stem Cells of Developing Prostate, Bladder, and Colorectal Epithelia, PNAS, 2013, 110(20):8105-8110.

Ponta, et al., CD44: From Adhesion Molecules to Signalling Regulators, Nature Reviews Molecular Cell Biology, 2003, 4:33-45.

Powell, et al., The Effect of Race/Ethnicity on Prostate Cancer Treatment Outcome is Conditional: A Review of Wayne State University Data, Journal of Urology, 2004, 171(4):1508-1512.

Qin, et al., The PSA-/lo Prostate Cancer Cell Population Harbors Self-Renewing Long-Term Tumor Propagating Cells that Resist Castration, Cell Stem Cell, 2012, 10:556-569.

Reinhardt, et al., Prostate Cancer Risk Alleles are Associated with Prostate Cancer Tumor Volume and Prostate Size, Journal of Urology, 2014, 191(6):1733-1736.

Richardson, et al., CD133, A Novel Marker for Human Prostatic Epithelial Stem Cells, Journal of Cell Science, 2004, 117:3539-3545.

Robbins, et al., Differences in Socioeconomic Status and Survival Among White and Black Men with Prostate Cancer, American Journal of Epidemiology, 2000, 151(4):409-416.

Rosenberg, et al., Genetic Diversity and Societally Important Disparities, Genetics, 2015, 201:1-12.

San Francisco, et al., Association of RNASEL and 8q24 Variants with the Presence and Aggressiveness of Hereditary and Sporadic Prostate Cancer in a Hispanic Population, J. Cell. Mol. Med., 2014, 18(1):125-133.

Schumacher, et al., Genome-Wide Association Study Identifies New Prostate Cancer Susceptibility Loci, Human Molecular Genetics, 2011, 20(19):3867-3875.

Seguin, et al., Integrins and Cancer: Regulators of Cancer Stemness, Metastasis, and Drug Resistance, Trends Cell Biol., 2015, 25(4):234-240.

Shuch, et al., Racial Disparity of Epidermal Growth Factor Receptor Expression in Prostate Cancer, Journal of Clinical Oncology, 2004, 22(23):4725-4729.

Siegel, et al., Cancer Statistics, 2016, CA Cancer J. Clin., 2016, 66:7-30.

Stranger, et al., Patterns of Cis Regulatory Variation in Diverse Human Populations, PLoS Genetics, 2012, 8(4): e1002639, 13 pages.

Tan, et al., Cancer Genomics: Diversity and Disparity Across Ethnicity an Geography, Journal of Clinical Oncology, 2016, 34(1):91-101.

Tryka, et al., NCBI's Database of Genotypes and Phenotypes: dbGaP, Nucleic Acids Research 2014, 42:D975-D979.

Vanhara, et al., Growth/Differentiation Factor-15: Prostate Cancer Suppressor or Promoter?, Prostate Cancer and Prostatic Diseases, 2012, 15:320-328.

Wacholder, et al., Assessing the Probability That a Positive Report is False: An Approach for Molecular Epidemiology Studies, Journal of the National Cancer Institute, 2004, 96(6):434-442.

Wang, et al., Androgen Receptor-Target Genes in African American Prostate Cancer Disparities, Hindawi Publishing Corporation, Prostate Cancer, vol. 2013, Article ID 763569, 15 pages, 2013.

Welter, et al., The NHGRI GWAS Catalog, a Curated Resource of SNP-Trait Associations, Nucleic Acids Research, 2014, 42:D1001-D1006.

Xu, et al., SNPinfo: Integrating GWAS and Candidate Gene Information Into Functional SNP Selection for Genetic Association Studies, Nucleic Acids Research, 2009, pp. 1-6.

Yang, et al., GCTA: A Tool for Genome-Wide Complex Trait Analysis, American Journal of Human Genetics, 2011, 88:76-82.

Yeager, et al., Genome-Wide Association Study of Prostate Cancer Identifies a Second Risk Locus at 8q24, Nature Genetics, 2007, 39(5):645-649.

Zhang, et al., miR-1303 Targets Claudin-18 Gene to Modulate Proliferation and Invasion of Gastric Cancer Cells, Digestive Diseases and Sciences, 2014, 59(8):1754-1763.

* cited by examiner

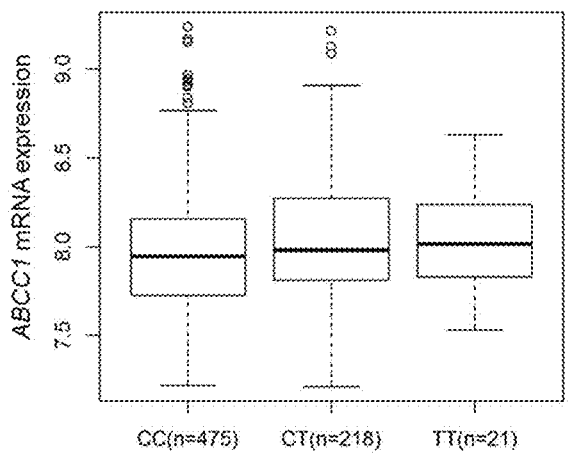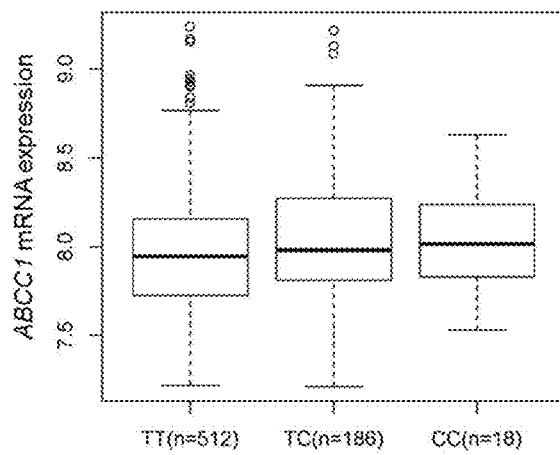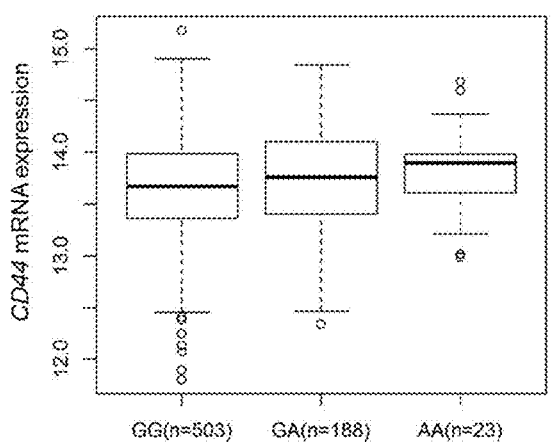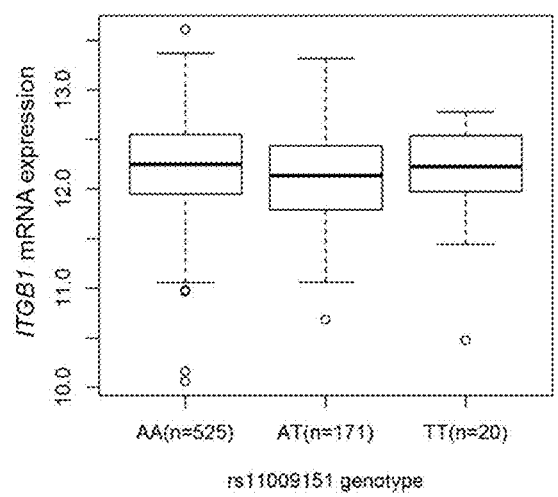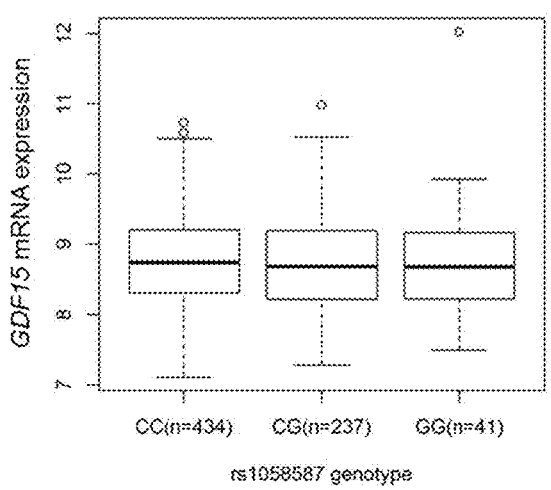

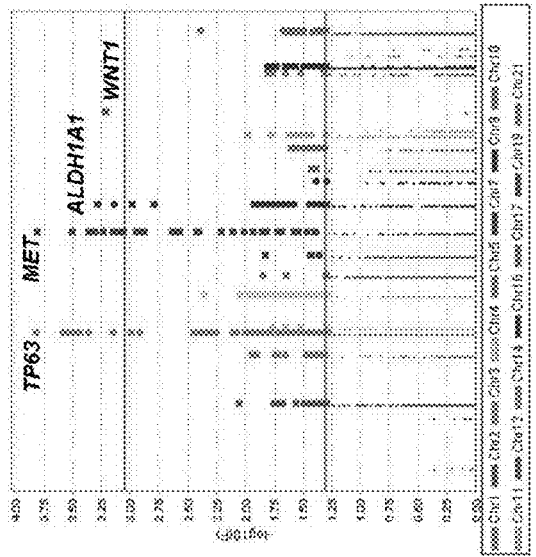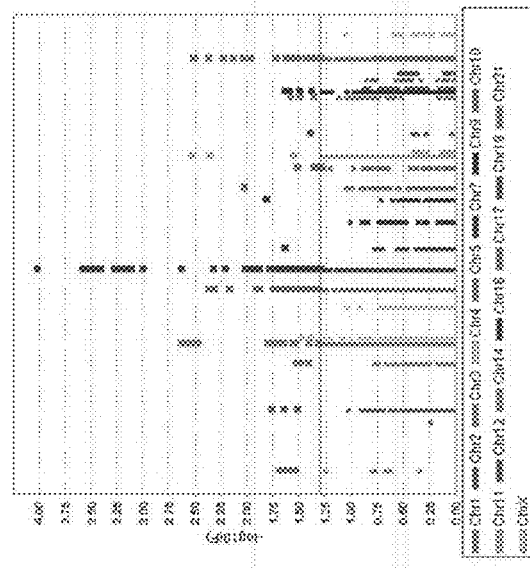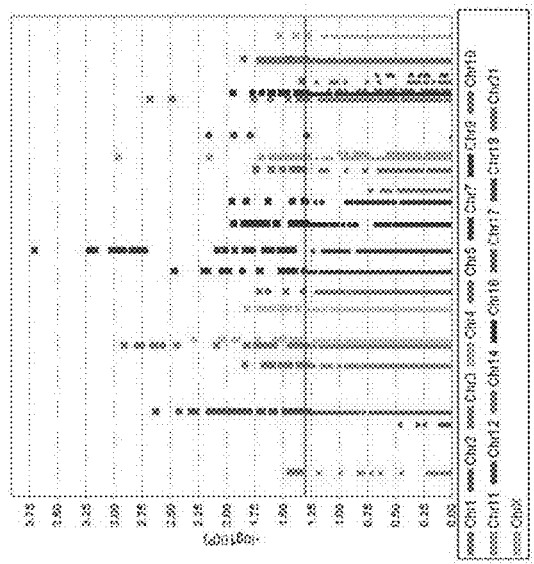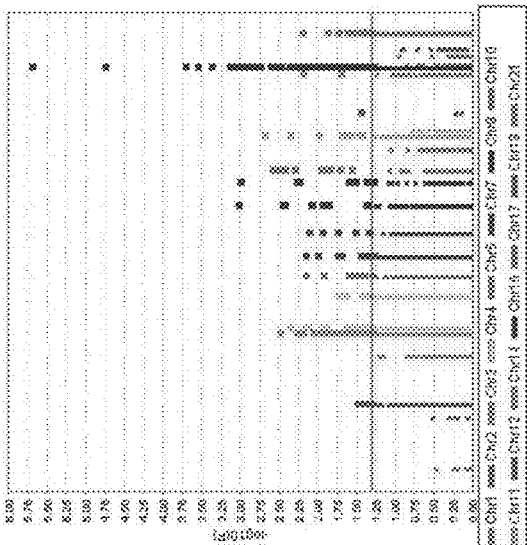
FIG. 10A  FIG. 10B  FIG. 10C  FIG. 10D  FIG. 10E  FIG. 10F

BIOMARKERS FOR THE IDENTIFICATION OF PROSTATE CANCER AND METHODS OF USE

CROSS-REFERENCE TO RELATED APPLICATIONS

This application claims priority to U.S. Provisional Application No. 62/250,723, filed Nov. 4, 2015, and U.S. Provisional Application No. 62/393,293, filed Sep. 12, 2016, each of which is incorporated herein in its entirety.

STATEMENT REGARDING FEDERALLY SPONSORED RESEARCH

This invention was made with Government supports under Federal Grant No. W81XWH-14-1-0569 awarded by the Army/MRMC. The Government has certain rights to this invention.

BACKGROUND

Prostate cancer is the second leading cause of cancer-related deaths in the US among men, with 220,800 new cases and 27,540 deaths estimated to occur in 2015. African American (AA) men exhibit a nearly 2-fold higher incidence and 3-fold higher mortality rate from prostate cancer compared to white men and disparities in tumor aggressiveness remain after controlling for social determinants of health. Very few studies have utilized this population-based difference to identify molecular mechanisms of tumor aggressiveness. Thus, there is an urgent need to elucidate the molecular mechanisms underlying the more aggressive prostate cancer biology in AA men.

Racial, ethnic and geographic disparities of prostate cancer have been observed in large_population-level studies (1-3). Notably, African Americans (AAs) have the highest rate of prostate cancer and prostate cancer in patients of African descent often exhibits a more aggressive phenotype (3). Specifically, according to the Surveillance, Epidemiology, and End Results Program (SEER) dataset in the US, the age-adjusted rate of prostate cancer was 203.5 per 100,000 among AA men versus 121.9 per 100,000 among white men for the period between 2009 and 2013 (3). Studies focusing on prostate cancer patients of African-descent have indicated that disparities in both incidence and mortality persist even after controlling for factors associated with social determinants of health and access to care (4). Though the mechanisms underlying prostate cancer disparities largely remain to be identified, high-throughput DNA sequencing has begun to elucidate a genomic landscape of cancer traits in recent years (5,6). In the context of this progress, it is likely that disparities in cancer incidence and mortality could be attributed to the diversity in the genome (7,8). For example, recent genome-wide association studies (GWASs) have identified more than a hundred independent loci associated with prostate cancer susceptibility (9). Approximately half of the risk factors for prostate cancer could be linked to inherited genetic factors (10). The GWAS-identified loci provide partial evidence for cancer risk assessment in the general population and have the potential to pave the way toward precision approaches for early detection and prevention of cancer (11,12). Among these studies, a few have been undertaken in populations of African descent, and most validation studies of susceptibility loci have not been consistent across different races and ethnicities (13-16). Therefore, studies in different racial and ethnic populations are needed to reveal the diverse etiology of prostate cancer and the_mechanisms underlying the observed disparities in genetic susceptibility to prostate cancer.

Accordingly, there is a need for providing improved methods for making a prognosis or assessing the risk regarding the development of prostate cancer, including the ability to determine the tumor aggressiveness and projected response and outcome to cancer treatment.

SUMMARY OF THE INVENTION

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

The present invention relates to the genetic profiling of a patient to identify single nucleotide polymorphisms (SNPs) affecting a person's risk of developing cancer, the aggressiveness of a patient's cancer and a person's survival from cancer to assist in improving diagnosis and clinical treatment decisions. The detection of SNPs associated with cancer risk, aggressiveness and/or survival has the potential to classify patients according to genetic factors, as a means for improving prediction of risk, prognosis and selection of treatments. The patient mat be a patient with cancer, a patient at risk of developing cancer, or any suitable patient.

In one aspect, a method for detecting a risk of cancer (e.g. prostate cancer) in a subject is provided. The method comprises the steps of: (i) collecting a sample from the subject; and (ii) detecting the presence of at least one SNP in a gene selected from the group consisting of TP63, MET, WNT1, ALDH1A1, FN1, COL, SEMA, ACACA, FASN, EGFR, and combinations thereof in the sample, wherein the presence of the SNP indicates an increased or decreased risk of prostate cancer in the subject. In some embodiments, the detecting the presence of at least one SNP in a gene selected from the group consisting of TP63, MET, WNT1, EGFR, and combinations indicates an increased risk of developing prostate cancer. In some embodiments, the detection of the presence of at least one SNP is a gene ALDH1A1 and the detection indicates a decreased risk of prostate cancer, more specifically a decreased risk of prostate cancer if the patient is African American.

In some aspects, a the SNPs are selected from the group consisting of TP63 rs56197129, TP63 rs6795002, TP63 rs6782221, TP63 rs6795465, TP63 rs56413159, TP63 rs73199732, TP63 rs55851920, TP63 rs7616437, MET rs116458171, MET rs139335187, MET rs201395418, MET rs567033632, MET rs115628473, MET rs377420134, MET rs916941, MET rs138238598, MET rs6966012, MET rs115240747, MET rs114707545, MET rs115293079, MET rs149188493, ALDH1A1 rs8187942, ALDH1A1 rs722921, WNT1 rs855723, FN1 rs11651 G/A, FN1 rs13652 C/T, COL6A3 rs36104025 G/C, COL6A3 rs3790993 C/G, SEMA3C rs1058425 T/C, ACACA rs1714987 G/C, FASN rs59638227 G/A in the sample, wherein the presence of the SNP indicates an increased or decreased risk of cancer in the subject. In some aspects, at least two SNPs are detected, in further aspects at least four SNPs, in further aspects at least five SNPs, in further aspects at least six SNPs.

In another aspect, a method for selectively treating a subject with a risk for cancer (e.g. prostate cancer) comprising the steps of: (a) confirming/determining an increased risk of cancer (e.g. prostate cancer) in a subject by a method comprising the steps of: (i) obtaining a sample from a subject; and (ii) detecting the presence of at least one SNP in a gene selected from the group consisting of TP63, MET, WNT1, FN1, COL, SEMA, ACACA, FASN, EGFR, and combinations thereof in the sample, wherein the presence of the at least one SNP indicates a risk of cancer; and (b) treating the subject with a risk of cancer with a cancer therapy.

In yet another aspect, a method for selectively treating a subject with aggressive prostate cancer is provided. The method comprises the steps of; (a) confirming the aggressive prostate cancer in a subject by a method comprising the steps of: (i) obtaining a sample from a subject; (ii) detecting the presence of at least one SNP in a gene selected from the group consisting of TP63, MET, WNT1, ALDH1A1, ACACA, SEMA3C, RELN, MYBPC1, NCOR2 and WDR4 in the sample, wherein the presence of the at least one SNP confirms either an aggressive form of prostate cancer or a non-aggressive form of prostate cancer; and (b) treating the subject with the aggressive form of prostate cancer with a cancer therapy suitable for treatment thereof. In other aspects, the subject is an African American male and the at least one SNP is selected from the group consisting of SEMA3C rs17275986 (G/A), RELN rs362708 (G/A), MYBPC1 rs3817552 (G/C), NCOR2 rs8546 (A/G), WDR4 rs15736 (G/A), WDR4 rs11911090 (T/C), and WDR4 rs2248490 (C/G).

In another aspect, a kit for detecting or determining a risk of cancer in a subject is provided. The kit comprises a means for detecting at least one SNP selected from the group consisting of TP63 rs56197129, TP63 rs6795002, TP63 rs6782221, TP63 rs6795465, TP63 rs56413159, TP63 rs73199732, TP63 rs55851920, TP63 rs7616437, MET rs116458171, MET rs139335187, MET rs201395418, MET rs567033632, MET rs115628473, MET rs377420134, MET rs916941, MET rs138238598, MET rs6966012, MET rs115240747, MET rs114707545, MET rs115293079, MET rs149188493, ALDH1A1 rs8187942, ALDH1A1 rs722921, WNT1 rs855723, FN1 rs11651 G/A, FN1 rs13652 C/T, COL6A3 rs36104025 G/C, COL6A3 rs3790993 C/G, SEMA3C rs1058425 T/C, ACACA rs1714987 G/C, FASN rs59638227 G/A in the sample, wherein the presence of the SNP indicates a risk of prostate cancer in the subject. Other aspects will be appreciated as described herein.

In another aspect, the present disclosure provides a method for detecting the presence of at least one SNP in a subject to assess a risk of cancer comprising the steps of;

(i) collecting a sample from the subject;

(ii) detecting the presence of at least one SNP within a gene selected from the group consisting of TP63, MET, WNT1, ALDH1A1, FN1, COL, SEMA, ACACA, FASN, EGFR, and combinations thereof in the sample, wherein the presence of the SNP indicates a risk of cancer in the subject.

In some aspects, the patient is African American, and step (ii) comprises detecting the presence of at least one SNP within a gene selected from the group consisting of TP63, MET, WNT1 and combinations thereof, wherein the presence of the SNP is associated with an increased risk of developing prostate cancer in the African American patient. In other aspects, the patient is African American, and step (ii) comprises detecting the presence of at least one SNP within a gene selected from the group consisting of ALDH1A1, FN1, COL6A3, SEMA3C, ACACA, and FASN, wherein the detection of at least one SNP indicated a decreased risk of developing prostate cancer. In a preferred aspect, the SNP is within the gene ALDH1A1, suitable ALDH1A1 rs8187942 or ALDH1A1 rs722921.

8. In other aspects, the patient is a non-Hispanic white male, and step (ii) comprises detecting the presence of at least one SNP within the gene selected from the group consisting of EGFR, FN1, FASN, wherein the presence of the SNP is associated with an increased risk of developing prostate cancer in the non-Hispanic white male patient. In yet another aspect, the patient is a non-Hispanic white male, and step (ii) comprises detecting the presence of at least one SNP within the gene COL6A3, SEMA3C, ACACA, wherein the presence of the SNP is associated with a decreased risk of developing prostate cancer in the non-Hispanic white male patient.

In a further aspect, the disclosure provides a method for selectively treating a subject with a higher risk for cancer comprising the steps of; (a) detecting at least one SNP associated with a higher risk of cancer in the subject by a method comprising the steps of: (i) obtaining a sample from a subject; (ii) detecting the presence of at least one SNP in a gene selected from the group consisting of TP63, MET, WNT1, FN1, COL, FASN, EGFR, and combinations thereof in the sample, wherein the presence of the at least one SNP confirms a higher risk of cancer; and (b) treating the subject with a risk of cancer with a cancer therapy.

In yet another aspect, the disclosure provides a method for detecting at least one SNP in a subject associated with tumor aggressiveness in a subject by a method comprising the steps of: (i) obtaining a sample from a subject; (ii) detecting the presence of at least one SNP in a gene selected from the group consisting of TP63, MET, WNT1, RELN, MYBPC1, NCOR2 and WDR4 in the sample, wherein the presence of the at least one SNP is associated with aggressive prostate cancer.

In yet another aspect, the disclosure provides a method of selectively treating a subject with aggressive prostate cancer comprising the steps of: (a) detecting at least on SNP associated with aggressive prostate cancer in the subject; and (b) treating the subject having an aggressive prostate cancer with at least one cancer therapy.

In still another aspect, a method of determining prostate cancer survival of a patient, comprising the steps of detecting at least on SNP within a gene selected from CD44, ABCC1, GDF15 and ITGB1 wherein the detection of at least one SNP is associated with prostate cancer survival.

In yet another aspect, the disclosure provides a kit for detecting a risk of prostate cancer in a subject comprising a means for detecting at least one SNP selected from the group consisting of TP63, MET, WNT1, FN1, COL, FASN, EGFR, and combinations thereof in the sample, wherein the presence of the SNP indicates a risk of prostate cancer in the subject.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 3A Correlation between the five independent and significant SNPs and the relative mRNA expression in lymphoblastoid cell lines of 716 individuals from HapMap 3 Project including 107 CEU, 242 CHB, 41 MEX and 326 AFR populations. rs35605 and ABCC1 (reporter: ILMN 1802404).

FIG. 3B Correlation between the five independent and significant SNPs and the relative mRNA expression in lymphoblastoid cell lines of 716 individuals from HapMap 3 Project including 107 CEU, 242 CHB, 41 MEX and 326 AFR populations. rs212091 and ABCC1 (reporter: ILMN 1802404).

FIG. 3C Correlation between the five independent and significant SNPs and the relative mRNA expression in lymphoblastoid cell lines of 716 individuals from HapMap 3 Project including 107 CEU, 242 CHB, 41 MEX and 326 AFR populations. rs9666607 and CD44 (reporter: ILMN 1803429).

FIG. 3D Correlation between the five independent and significant SNPs and the relative mRNA expression in lymphoblastoid cell lines of 716 individuals from HapMap 3 Project including 107 CEU, 242 CHB, 41 MEX and 326 AFR populations. rs11009151 and ITGB1 (reporter: ILMN 1723467).

FIG. 3E Correlation between the five independent and significant SNPs and the relative mRNA expression in lymphoblastoid cell lines of 716 individuals from HapMap 3 Project including 107 CEU, 242 CHB, 41 MEX and 326 AFR populations. rs1058587 and GDF15 (reporter: ILMN 1763658).

FIG. 10A Manhattan plots of the four studies and the meta-analysis results of the two racial populations. The red horizontal line indicates P=0.05 and the blue line indicates FDR=0.2. 6,549 common SNPs from the Ghana study.

FIG. 10B Manhattan plots of the four studies and the meta-analysis results of the two racial populations. The red horizontal line indicates P=0.05 and the blue line indicates FDR=0.2. 6,267 common SNPs from the MEC AA study.

FIG. 10C Manhattan plots of the four studies and the meta-analysis results of the two racial populations. The red horizontal line indicates P=0.05 and the blue line indicates FDR=0.2. The meta-analysis of 5,448 SNPs in two studies of African descendants.

FIG. 10D Manhattan plots of the four studies and the meta-analysis results of the two racial populations. The red horizontal line indicates P=0.05 and the blue line indicates FDR=0.2. 5,239 common SNPs from the PLCO study.

FIG. 10E Manhattan plots of the four studies and the meta-analysis results of the two racial populations. The red horizontal line indicates P=0.05 and the blue line indicates FDR=0.2. 5,345 common SNPs from the BPC3 study.

FIG. 10F Manhattan plots of the four studies and the meta-analysis results of the two racial populations. The red horizontal line indicates P=0.05 and the blue line indicates FDR=0.2. The meta-analysis of 4,934 SNPs in two studies of non-Hispanic whites.

DETAILED DESCRIPTION OF THE INVENTION

Figure 1A:
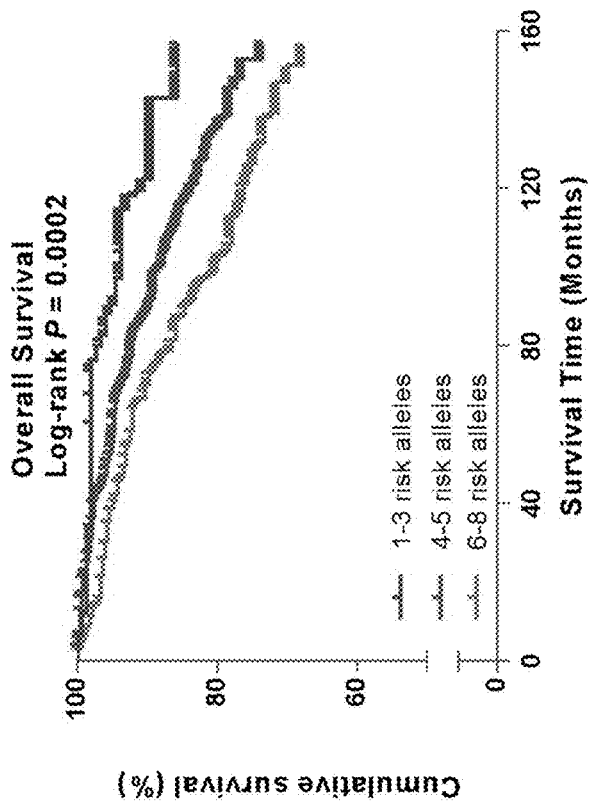
FIG. 1A Kaplan-Meier survival curves of prostate cancer patients according to combined risk alleles of the five independent and significant SNPs.

The present invention has been described in terms of one or more preferred embodiments, and it should be appreciated that many equivalents, alternatives, variations, and modifications, aside from those expressly stated, are possible and within the scope of the invention.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

Distinct gene expression patterns, somatic and germline single nucleotide polymorphisms (SNPs), splice variants and epigenetic patterns underlying AA prostate cancer can serve as novel precision biomarkers and/or molecular targets for precision medicine interventions. Such differences will 1) increase our understanding of the molecular mechanisms underlying prostate cancer in AA men, 2) pave the way toward developing novel specific approaches for prevention and treatment that will help reduce prostate cancer disparities for AAs and 3) improve prevention and treatment in men of all races with aggressive disease driven by these mechanisms.

The present invention relates to the genetic profiling of a patient to identify single nucleotide polymorphisms (SNPs) affecting a person's risk of developing cancer, the aggressiveness of a patient's cancer and a patient's survival from cancer and assisting in improving diagnosis and clinical treatment decisions. The detection of SNPs associated with cancer has the potential to classify patients according to genetic factors, as a means for improving prediction of risk, prognosis and selection of treatments. Therefore, the present invention provides methodologies and kits for predicting a patient's risk of developing cancer, aggressiveness of a patient's cancer and the patient's chance of survival based upon the presence or absence of at least one SNP. The present invention also relates to associating the occurrence of SNPs with the survival of the patient by detecting at least one SNP associated with an increased or decreased survival, as discussed in Table 3 and Example 3. Further, the present invention provides methods and kits for predicting the aggressiveness of the cancer by detecting at least one SNP associated with tumor aggressiveness.

The present invention relates to prostate cancer biomarkers, specifically SNPs. The prostate cancer biomarkers of the present invention may be used in, but are not limited to, methods of detecting prostate biomarkers in a subject, methods to detect a subject's risk of prostate cancer, methods to preventatively treat a subject at risk for prostate cancer, and methods for treating a subject with prostate cancer. One of skill in the art will readily appreciate the utility of the prostate cancer biomarkers in a variety of methods. Further the present invention provides kits for detecting prostate cancer biomarkers and kits for determining the aggressiveness of prostate cancer and kits for treating a subject for prostate cancer, specifically an aggressive form of prostate cancer.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

"About" is used to provide flexibility to a numerical range endpoint by providing that a given value may be "slightly above" or "slightly below" the endpoint without affecting the desired result.

As used herein, "treatment" or "treating" refers to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. Specifically, treatment results in the reduction in tumor load or volume in the patient, and in some instances, leads to regression and elimination of the tumor or tumor cells. As used herein, the term "treatment" is not necessarily meant to imply cure or complete abolition of the tumor. Treatment may refer to the inhibiting or slowing of the progression of the tumor, reducing the incidence of tumor, reducing metastasis of the tumor, or preventing additional tumor growth. In some embodiments, treatment results in complete regression of the tumor.

By "ameliorate," "amelioration," "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the compositions of the present invention, where the untreated subjects have, or are subject to developing, the same or similar tumor.

The term "effective amount" or "therapeutically effective amount" refers to an amount sufficient to effect beneficial or desirable biological and/or clinical results.

The term "disease" as used herein includes, but is not limited to, any abnormal condition and/or disorder of a structure or a function that affects a part of an organism. It may be caused by an external factor, such as an infectious disease, or by internal dysfunctions, such as cancer, autoimmune diseases and the like. In a preferred embodiment, the disease is cancer, preferably prostate cancer.

As is known in the art, a cancer is generally considered as uncontrolled cell growth. The methods of the present invention can be used to treat any cancer including, but not limited to, carcinoma, for example, breast cancer, prostate cancer, small-cell lung cancer, non-small cell lung cancer, liver cancer, and the like. In certain embodiments, the cancer comprises prostate cancer. The term "cancer" and "tumor" are used herein interchangeably.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is suffering from cancer (e.g., prostate cancer). In a preferred embodiment, the patient is suffering from an aggressive form of the cancer, for example an aggressive form of prostate cancer. In one embodiment, the subject is preferably an African American male suffering from prostate cancer. In another embodiment, the subject is a non-Hispanic white male.

As used herein, the term "cancer therapy" and "therapy" refer to a therapy known to one skilled in the art, including but not limited to, for example a therapy selected from the group consisting of chemotherapy, hormone therapy, androgen therapy, radiation, surgery, vaccine therapy, immunotherapy and combinations thereof. A suitable therapy include, but are not limited to, splice-switching oligomers as disclosed in PCT Patent Application No. PCT/US2016/6549 filed on Nov. 4, 2016 entitled "Splice-Switching Oligonucleotides and Methods of Use" which claims priority U.S. Provisional Application Nos. 62/250,713 and 62/274,427, the contents of which are incorporated by reference in their entireties. Suitable therapies are known by one skilled in the art. For example, in patients that have high expression of a SNPs associated with EGFR with a higher risk of prostate cancer, suitable SSOs can be used to treat the prostate cancer specific to EGFR, as disclosed in the above-noted PCT application.

In some embodiments, if the SNPs identified modulate expression of proteins/variants or drive production of novel proteins/variants, the proteins/variants can be targeted at the mRNA level or the protein level to treat the cancer. At the mRNA level e.g. siRNAs could be used. At the protein level e.g. targeted therapeutics, small molecules, antibodies, pharmacologic inhibitors of signaling could be used. If the SNPs play a role in splicing regulation and drive production of novel proteins/variants by affecting splicing then splice-switching oligomers (SSOs) could be used to target the pre-mRNA/splicing process. For example, in non-Hispanic white males which have a SNP within the EGFR gene, suitable SSOs that target the EGFR splicing sites may be used to treat the cancer.

"Chemotherapy" refers to the administration to a patient of a chemotherapeutic drug, agent, compound or pharmaceutical that used for killing cancer cells. A "surgery" refers to the act of surgery or surgical procedures that involve the use of operative manual and instrumental techniques on a patient to investigate and/or treat a pathological condition such as disease or injury. A "radiation" in the context of cancer refers to the use of high-energy radiation such as ionizing radiation to shrink tumors and kill cancer cells. "Hormone therapy" for prostate cancer is also called androgen deprivation therapy (ADT) or androgen suppression therapy. The hormone therapy reduces the levels of male hormones, called androgens, in the body, or to stop them from affecting prostate cancer cells as androgens stimulate prostate cancer cells to grow.

The term "immunotherapy" refers to a treatment or therapy that results in an immune response for the treatment of a disease. An immunotherapy is a therapy used to treat a disease by inducing, amplifying or enhancing an immune response against antigens specific to the disease, for example, tumor associated antigens expressed on cancer cells. In some instances, immunotherapy may be a cell-based immunotherapy that employs target immune effector cells such as lymphocytes, macrophages, dendritic cells, natural killer cells (NK cells), cytotoxic T lymphocytes (CTL), and the like to target abnormal antigens expressed on the surface of cancer/tumor cells. In a preferred embodiment, at least one immunotherapy may be a T cell immunotherapy. Suitable T cell immunotherapies are known in the art and include, but are not limited to, for example, vaccines (e.g. DNA vaccine), oncolytic viral therapies that engage/recruit T cells, adoptive immunotherapies approaches (e.g. CAR T cells), or biospecific T cell engagers (BiTEs).

As used herein, the term "alternative splicing" refers to variations in the splicing of pre-mRNAs to generate mature mRNAs in genes which contain multiple exons. During normal growth and differentiation, gene expression involves splicing of pre-mRNAs to generate mature mRNAs. It is now appreciated that >90% of genes containing multiple exons in the genome are subject to alternative splicing, in which specific exons are included or skipped to create multiple protein isoforms from a single pre-mRNA transcript. In addition to playing an important role during normal growth and differentiation, alternative splicing has also been shown to contribute to carcinogenesis.

Complete changes in the isoforms generated as well as modest shifts in the relative proportions of the isoforms generated from alternative splicing of an individual gene can be pathogenic. Both cis-acting splicing elements, which are elements within the genes themselves, and trans-acting splicing factors, which are factors from outside the gene, regulate splicing. Variation in these elements and factors drives alternative splicing.

As used herein the term "single nucleotide polymorphism" or "SNP" refers to a variation in a single nucleotide that occurs at a specific position in a genome, where each variation is present to some appreciable degree within the population comprising the genome. The number recited for each SNP are defined as number of nucleotides 5' or 3' counting from the A of the ATG-translation initiation codon, respectively which is altered in the SNP.

As used herein the term "cis-acting polymorphism" refers to a SNP within a gene or which regulates the expression or splicing of that gene. Cis-acting polymorphisms may result in altered isoforms in several genes that have functional consequences, including, but not limited to, for example, alterations in immune response, MHC antigen presentation and response to therapies, among others.

Without being bound by any particular theory, previous work has theorized the contribution of alternative splicing as a novel molecular mechanism underlying the more aggressive prostate cancer in AA men. A subset of these alternatively spliced target genes whose splicing is significantly altered in AA prostate cancer and are prostate cancer-associated genes, androgen receptor target genes or genes whose splicing is significantly altered in additional cancers (breast, lung and liver) have been identified. The subsets of alternatively spliced target genes that differ from AA men and non-Hispanic white men are discussed more in Example 4 below.

SNPs located in splicing regulatory regions of the targeted genes of interest have the potential to effect splicing of the alternatively spliced genes between prostate cancer in AA and non-hispanic white males. These SNPs are associated with prostate cancer risk (either increased or decreased risk of developing prostate cancer), aggressiveness of the prostate cancer and/or survival of the patient in white and AA groups of patients. SNPs that significantly associate with prostate cancer risk (Table 2, FIG. 13), aggressiveness (Table 3, FIG. 14) and survival (Table 4, FIG. 15) in non-Hispanic white and AA groups are outlined below based on analysis of publically available data in the Prostate, Lung, Colorectal and Ovarian Cancer Screening Trial (PLCO) and the Multiethnic Cohort Study (MEC). As shown in Table 1 and FIG. 13, the odd ratio (OD) provides a measure of the risk of developing prostate cancer. Depending on if the OD is above or below 1 correlates with the SNP being associated with a higher risk (>1 OD) or lower/decreased risk (<1 OD, protective risk) of developing prostate cancer in that population of patients (e.g. AA or non-Hispanic white patients). Further SNPs associated with an increased or decreased risk of developing prostate cancer in AA or white patient groups is also discussed in Example 4 below and the SNPs are detailed and listed in Table 13. As stated, for Table 13, SNPs with an OD>1 indicate an increased risk of developing prostate cancer, and <1 indicates a decreased risk of developing prostate cancer.

One aspect of the present invention relates to the use of identified SNPs as biomarkers for prostate cancer. The invention relates to the detection of at least one SNP for the detection or prognosis of prostate cancer, the detection of an increased or decreased risk of developing prostate cancer, the detection of a higher risk of developing an aggressive form of prostate cancer (or in the alternative, a decreased risk of developing an aggressive form of prostate cancer or higher chance of developing non-aggressive form of prostate cancer), or the increased or decreased survival of a subject having prostate cancer.

Suitable SNPs are described in Example 4 below. Briefly, in some embodiments, the SNPS within the gene TP63, MET, WNT are associated with increased prostate cancer risk in AA males. In some embodiments, SNPs within the gene ALDH1A1 are associated with a decreased risk (or protective phenotype) of developing prostate cancer in AA males. Further, SNPs within the gene EGFR are associated with increased prostate cancer risk in non-Hispanic white males. These SNPs are predicted to be functional, playing roles in RNA splicing and transcriptional regulation and therefore are targets for treatment of the underlying prostate cancer.

In some embodiments, at least one SNP is selected and detected, alternatively at least two SNPs, alternatively at least three SNPs, alternatively at least four SNPs, alternatively at least five SNPs, alternatively at least six SNPs are selected and detected.

In some aspects, the detection of the presence of more than one SNP with an odd ratio of greater than 1, for example, at least two SNP, at least three SNP, at least 4 SNP, at least 5 SNP indicates a higher risk of developing prostate cancer.

In some embodiments, a method of determining susceptibility of an individual to prostate cancer comprising obtaining a sample of genetic material from the individual and determining the presence of at least one SNPs described herein are provided.

In further preferred embodiments SNPs are determined by sequencing, custom SNP genotyping assay or SNP chip, which are known methods in the art.

The method may further comprise obtaining a sample from the individual and determining the presence of prostate cancer marker substance or SNP therein. The marker substance or SNP may be specific for the presence of prostate cancer in an individual.

Samples may be tissue samples or body fluid sample. In alternative embodiments samples may be obtained from subjects (e.g. patients with or without cancer) by other methods well known in the art, including but not limited to, samples of blood, serum, urine, ascites and intraperitoneal fluids.

Blood samples may be taken via venipuncture, (e.g. by vacuum collection tube or syringe,) catheter, cannula, or by finger prick or heel prick as appropriate to the needs of the patient and the amount of blood required. Once a blood sample has been taken it may be treated prior to analysis (e.g. with sodium citrate, EDTA, ethanol or Heparin) for the purposes of preservation or in order to maximize the accuracy and/or reliability of the signal obtained by analysis of the sample.

Methods of processing (e.g. centrifugation and/or filtration) may be used to separate a blood sample into fractions each of which may be tested independently. For example, a blood serum sample is produced by allowing a whole-blood sample to clot on contact with air where the clotted fraction is removed by centrifugation to leave the serum as the supernatant.

Urine samples are preferably collected by urination or catheterization.

The cells and/or liquid collected in a sample taken from a patient may be processed immediately or preserved in a suitable storage medium for later processing. For example, in the case of a blood sample the cells are often preserved in an EDTA containing storage medium for later processing and analysis. The sample may be treated for the purposes of preservation or for maximizing the accuracy and/or reliability of the signal obtained by analysis of the sample. Methods of processing (e.g. centrifugation and/or filtration) may be used to separate a sample into fractions each of which may be tested independently.

In one example, genomic DNA may be isolated from samples obtained from the patients by techniques described in the art. The genomic DNA may be subsequently amplified by polymerase chain reaction (PCR) by using any methodology available in the art, thus providing amplified regions of interest of the genomic DNA. The primers used to amplify the DNA may be already known in the art, or designed using available software. The parameters, enzymes and reagents used to perform the PCR may be carefully chosen to ensure the integrity of DNA after amplification. The PCR products may be purified and isolated to allow their sequencing. One skilled in the art is aware of numerous molecular biology methods, apparatus and reagents for purification of PCR products. In some embodiments, purified PCR products may be sequenced.

In one example, the PCR products may be sequenced by techniques described and well known in the art. Examples of available techniques and methods for sequencing of PCR products may include subcloning and sequencing or direct sequencing of the PCR product using methods well known to the skilled person in the art. For example, pyrosequencing may be used to directly sequence purified PCR products.

Aspects of the present disclosure that are described with respect to methods can be utilized in the context of kits discussed in this disclosure. Similarly, aspects of the present disclosure that are described with respect to the kits can be utilized in the context of the methods. This disclosure provides kits. The kits can be suitable for use in the methods described herein.

In one embodiment, the disclosure provides kits for detecting or determining a risk of cancer or presence of cancer in a subject comprising a means for detecting at least one SNP described herein. In a preferred embodiment, the cancer is prostate cancer. Suitable means for detecting a SNP in a sample are known in the art. In one embodiment, the means for detecting or determining the SNPs are sequencing or SNP chip.

In another embodiment, the disclosure provides kits for treating a subject with cancer or at risk of developing an aggressive form of cancer, preferably prostate cancer, the kit comprising means for determining a risk of cancer in a subject by means for detecting the presence of at least one SNP and a means for treating the subject.

In one example, the kit may further include but is not limited to, for example probes or primers for detecting the genotypes of the SNPs and amplification of a sequence comprising the at least one SNP which allows the determination of the genotype defined by the SNPs. The reagents can be defined as those necessary to isolate a nucleic acid from a sample and detect the presence or absence of at least one SNP.

Suitable methods for identifying SNPs include, but are not limited to, sequencing, custom SNP genotyping assays and SNP chips.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products.

In one example, genomic DNA may be isolated from samples obtained from the patients by techniques described in the art. The genomic DNA may be subsequently amplified by polymerase chain reaction (PCR) by using any methodology available in the art, thus providing amplified regions of interest of the genomic DNA. The primers used to amplify the DNA may be already known in the art, or designed using available software. The parameters, enzymes and reagents used to perform the PCR may be carefully chosen to ensure the integrity of DNA after amplification. The PCR products may be purified and isolated to allow their sequencing. Numerous molecular biology art describe methods, apparatus and reagents for purification of PCR products. Purified PCR products may be sequenced.

In one example, the PCR products may be sequenced by techniques described and well known in the art. Examples of available techniques and methods for sequencing of PCR products may include subcloning and sequencing or direct sequencing of the PCR product using methods well known to the skilled person in the art. For example, pyrosequencing may be used to directly sequence purified PCR products.

In some embodiments, a probe is used to determine the SNPs. The term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present disclosure be limited to any particular detection system or label. In some embodiments, the kit includes a SNP chip that can detect at least one of the SNPs identified herein.

The term "increased" in the context of a patient's chance of survival refers to the increased prolongation of life expectancy relative to the presence or absence of an SNP. The term "decreased" in the context of a patient's chance of survival refers to the maintenance or reduce life expectancy relative to the presence or absence of an SNP.

The term "aggressive" or "aggressiveness" as it pertains to cancer relates to a cancer that is at stage 3 or higher and/or a gleson score of ≥8.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

Suitable SNPs for practicing the methods of the present invention are described in Table 1-3, related to the risk of developing prostate cancer (Table 1), aggressiveness of the prostate cancer (Table 2) and the survival of a subject with prostate cancer (Table 3) which has been determined for the subpopulations of African American males and non-Hispanic white males.

TABLE 1

Significant associations between splicing-related SNPs in prioritized target genes and prostate cancer risk in either PLCO European population or MEC African American population.

| SNP | Gene | PLCO European population(N = 2251) | | | | MEC African American(N = 1371) | | | |
|---|---|---|---|---|---|---|---|---|---|
| | | A1_Cases[1] | A1_Controls[1] | OR(95% CI)[2] | P[2] | A1_Cases[1] | A1_Controls[1] | OR(95% CI)[2] | P[2] |
| r511651 (G/A) | FN1 | 0.35 | 0.32 | 1.19(1.01-1.38) | 0.033 | 0.11 | 0.11 | 0.97(0.75-1.25) | 0.819 |
| rs13652 (C/T) | FN1 | 0.13 | 0.11 | 1.29(1.02-1.63) | 0.031 | 0.19 | 0.19 | 0.99(0.82-1.21) | 0.949 |
| rs36104025 (G/C) | COL6A3 | 0.09 | 0.08 | 1.34(1.02-1.75) | 0.036 | — | — | — | — |
| rs3790993 (C/G) | COL6A3 | 0.45 | 0.46 | 0.85(0.73-0.99) | 0.036 | 0.43 | 0.44 | 0.96(0.82-1.12) | 0.627 |
| rs1058425 (T/C) | SEMA3C | 0.1791 | 0.1962 | 0.85(0.7-1.03) | 0.094 | 0.3982 | 0.4336 | 0.82(0.70-0.96) | 0.0145 |
| rs1714987 (G/C) | ACACA | 0.17 | 0.2 | 0.8(0.66-0.96) | 0.02 | 0.27 | 0.27 | 0.98(0.82-1.17) | 0.823 |
| rs59638227 (G/A) | FASN | 0.30 | 0.29 | 1.02(0.86-1.21) | 0.792 | 0.1154 | 0.1425 | 0.74(0.58-0.94) | 0.0142 |

[1]Frequency of A1 allele.
[2]Adjusted for the top three principle components and age at diagnosis.

Figure 13:
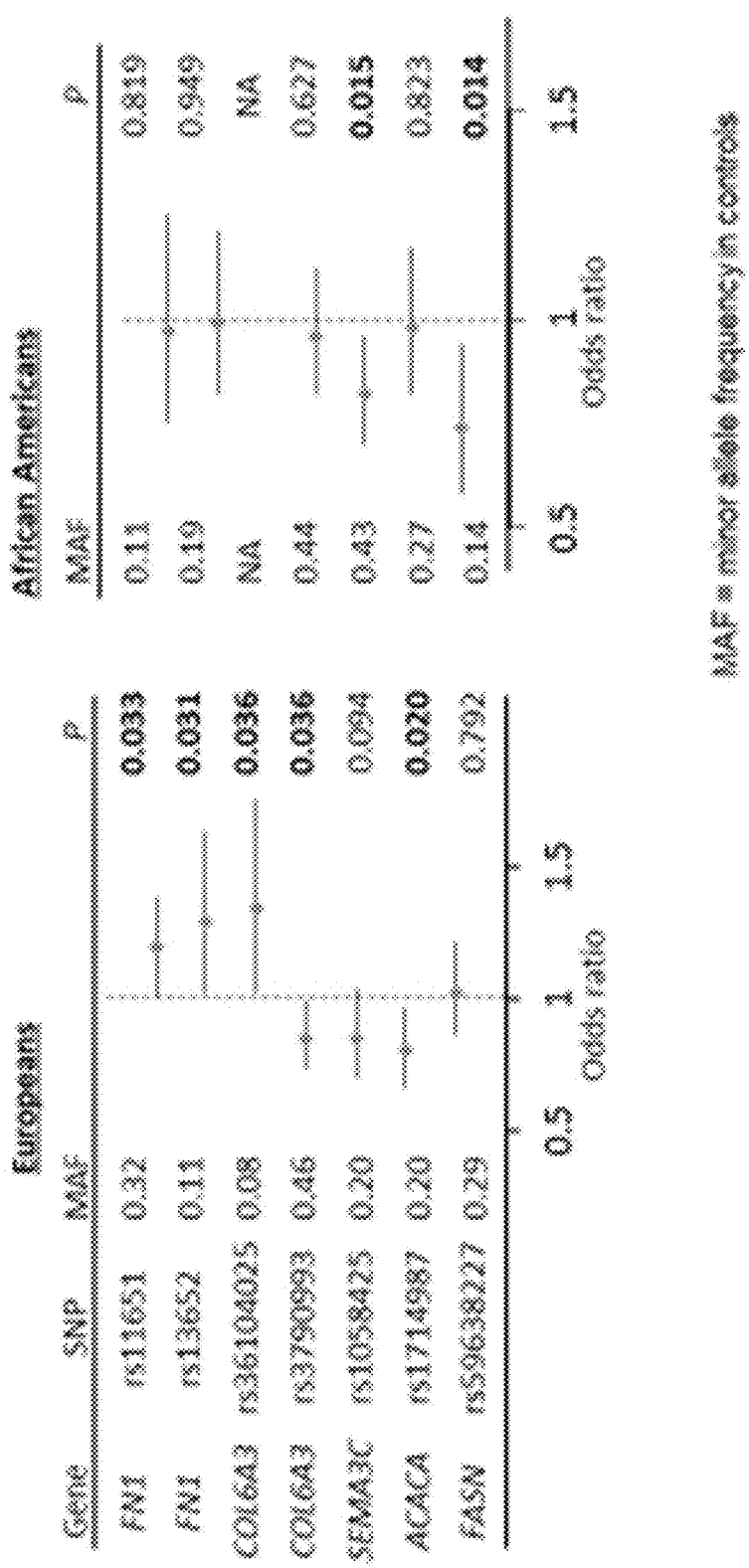
FIG. 13 depicts the odds ratio of splicing-related SNPs in prioritized target genes and prostate cancer risk in either PLCO European population or MEC African American population.

The odds ratio (OR) were graphed in FIG. 13. An odds ratio of greater than 1 is associated with an increased risk of developing prostate cancer. An odds ratio of less than 1 (<1) is associated with a decreased risk of developing prostate cancer (e.g. provide a protective effect).

TABLE 2

Significant associations between splicing-related SNPs in prioritized target genes and prostate cancer aggressiveness in either PLCO European population or African American population.

| SNP | Gene | PLCO population | | | | African American | | | |
|---|---|---|---|---|---|---|---|---|---|
| | | A1_Aggressive (N = 237)[1] | A1_Non Aggressive (N = 843)[1] | OR(95% CI)[2] | P[2] | A1_Aggressive (N = 234)[1] | A1_Non-Aggressive (N = 436)[1] | OR(95% CI)[2] | P[2] |
| rs1714987 (G/C) | ACACA | 0.134 | 0.182 | 0.70 (0.52-0.93) | 0.015 | 0.260 | 0.271 | 0.97 (0.73-1.28) | 0.826 |
| rs17275986 (G/A) | SEMA3C | 0.213 | 0.212 | 0.98 (0.76-1.25) | 0.861 | 0.061 | 0.096 | 0.59 (0.36-0.96) | 0.034 |
| rs362708 (G/A) | RELN | NA | NA | NA | NA | 0.414 | 0.354 | 1.30 (1.00-1.67) | 0.047 |
| rs3817552 (G/C) | MYBPC1 | 0.148 | 0.144 | 1.05 (0.78-1.41) | 0.7373 | 0.144 | 0.099 | 1.53 (1.06-2.22) | 0.024 |
| r58546 (A/G) | NCOR2 | 0.159 | 0.160 | 0.98 (0.74-1.31) | 0.9047 | 0.133 | 0.092 | 1.49 (1.01-2.22) | 0.046 |
| r515736 (G/A) | WDR4 | 0.359 | 0.381 | 0.90 (0.73-1.11) | 0.3163 | 0.442 | 0.368 | 1.40 (1.09-1.80) | 0.009 |
| rs11911090 (T/C) | WDR4 | 0.101 | 0.081 | 1.27 (0.90-1.78) | 0.174 | 0.185 | 0.141 | 1.40 (1.01-1.95) | 0.044 |
| rs2248490 (C/G) | WDR4 | 0.491 | 0.492 | 1.00 (0.82-1.23) | 0.9697 | 0.356 | 0.276 | 1.51 (1.16-1.99) | 0.003 |

[1]Frequency of A1 allele.
[2]Adjusted for the top three principle components and age at diagnosis.

Figure 14:
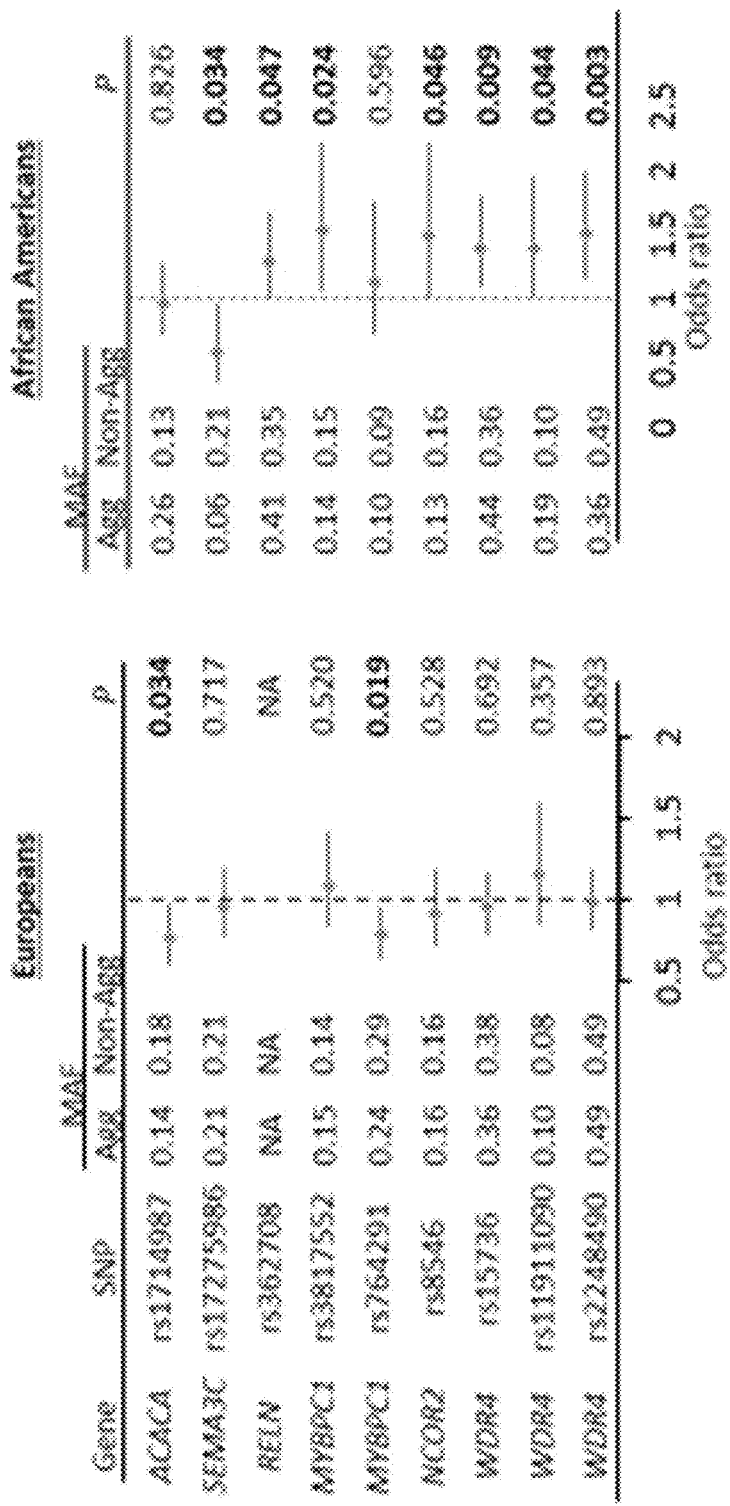
FIG. 14 depicts the odds ratio splicing-related SNPs in prioritized target genes and prostate cancer aggressiveness in either PLCO European population or African American population.

The odds ratio (OR) were graphed in FIG. 14. An odds ratio of greater than 1 is associated with an increased risk of developing aggressive form of prostate cancer. An odds ratio of less than 1 (<1) is associated with a decreased risk of developing aggressive prostate cancer (e.g. increased chance of developing non-aggressive prostate cancer). Aggressive form of prostate cancer is defined as stage III/IV or Gleason score ≥8.

sample, wherein the presence of the SNP indicates a risk of cancer in the subject. In some embodiments, the gene is a gene listed in Table 1 or Table 13, or the SNP is a SNP listed in Table 1 or Table 13.

In some embodiments, the SNP detected for assessing the risk of a cancer includes at least one SNP that is selected from the group consisting of TP63 rs56197129, TP63 rs6795002, TP63 rs6782221, TP63 rs6795465, TP63

TABLE 3

Significant associations between splicing-related SNPs in prioritized target genes and survival of 1150 prostate cancer patients in PLCO.

| SNP | Gene | A1A1/A1A2/A2A2 | Overall (N = 1150) | | Aggressiveness[2] (N = 237) | | Non-aggressiveness (N = 843) | |
| --- | --- | --- | --- | --- | --- | --- | --- | --- |
| | | | HR (95% CI)[1] | P[1] | HR (95% CI)[1] | P[1] | HR (95% CI)[1] | P[1] |
| rs3738073 (T/C) | RHOU | 48/378/723 | 1.34 (1.06-1.68) | 0.013 | 1.65 (1.02-2.65) | 0.04 | 1.33 (1.00-1.77) | 0.047 |
| rs7596677 (T/A) | FN1 | 66/395/647 | 1.07 (0.85-1.34) | 0.564 | 1.59 (0.01-2.50) | 0.045 | 0.92 (0.69-1.23) | 0.577 |
| rs1131296 (A/G) | COL6A3 | 185/572/394 | 0.88 (0.71-1.08) | 0.21 | 0.64 (0.42-0.99) | 0.044 | 0.95 (0.74-1.22) | 0.69 |
| rs1880959 (A/C) | SEMA3C | 8/215/921 | 0.71 (0.5-1.02) | 0.067 | 0.82 (0.41-1.65) | 0.575 | 0.63 (0.40-0.99) | 0.047 |
| rs2229862 (A/G) | RELN | 3/118/1030 | 1.53 (1.04-2.26) | 0.031 | 3.56 (1.71-7.43) | 0.001 | 1.02 (0.61-1.72) | 0.933 |
| rs362691 (C/G) | RELN | 11/236/901 | 0.85 (0.62-1.17) | 0.328 | 0.38 (0.17-0.87) | 0.022 | 1.03 (0.71-1.49) | 0.888 |
| rs9666607 (A/G) | CD44 | 109/493/549 | 1.28 (1.04-1.58) | 0.019 | 1.13 (0.75-1.70) | 0.558 | 1.29 (1.00-1.67) | 0.050 |
| rs1467558 (T/C) | CD44 | 45/337/769 | 1.24 (0.97-1.57) | 0.081 | 1.10 (0.67-1.80) | 0.701 | 1.37 (1.02-1.82) | 0.034 |
| rs17706535 (G/A) | LMO7 | 8/216/903 | 0.91 (0.65-1.27) | 0.573 | 0.47 (0.23-0.96 | 0.039 | 1.09 (0.72-1.64) | 0.684 |
| rs15736 (A/G) | WDR4 | 167/540/444 | 1.25 (1.03-1.52) | 0.023 | 1.32 (0.90-1.94) | 0.157 | 1.15 (0.90-1.46) | 0.259 |

[1]Adjusted for age, stage, Gleason score, primary treatment and the top three principle components.
[2]Aggressive was defined as "stage III/IV or Gleason score ≥ 8".

Figure 15:
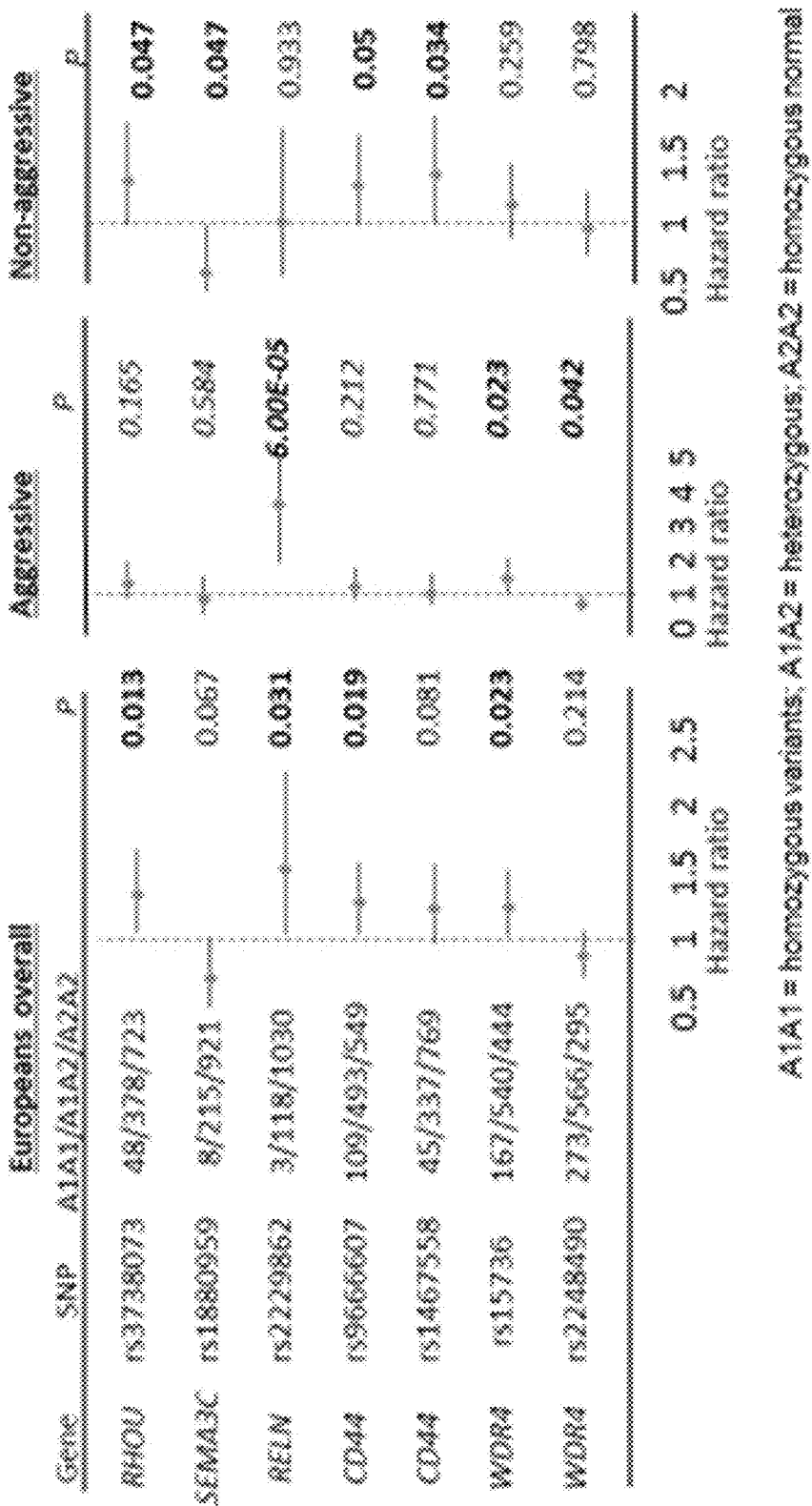
FIG. 15 depicts the odds ratio of splicing-related SNPs in prioritized target genes and survival of 1150 prostate cancer patients in PLCO.

The odds ratio (OR) were graphed in FIG. 15. An odds ratio of greater than 1 is associated with an increased risk of developing aggressive form of prostate cancer and a decreased risk of survival. An odds ratio of less than 1 (<1) is associated with a decreased risk of developing aggressive prostate cancer (e.g. increased chance of developing non-aggressive prostate cancer) and an decreased chance of survival.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The following non-limiting examples are included for purposes of illustration only, and are not intended to limit the scope of the range of techniques and protocols in which the compositions and methods of the present invention may find utility, as will be appreciated by one of skill in the art and can be readily implemented.

In one embodiment, a method for detecting the presence of at least one SNP in a subject to assess a risk of cancer is provided. The method comprises (i) collecting a sample from the subject; (ii) detecting the presence of at least one SNP within a gene selected from the group consisting of TP63, MET, WNT1, ALDH1A1, FN1, COL, SEMA, ACACA, FASN, EGFR, and combinations thereof in the rs56413159, TP63 rs73199732, TP63 rs55851920, TP63 rs7616437, MET rs116458171, MET rs139335187, MET rs201395418, MET rs567033632, MET rs115628473, MET rs377420134, MET rs916941, MET rs138238598, MET rs6966012, MET rs115240747, MET rs114707545, MET rs115293079, MET rs149188493, ALDH1A1 rs8187942, ALDH1A1 rs722921, WNT1 rs855723, FN1 rs11651 G/A, FN1 rs13652 C/T, COL6A3 rs36104025 G/C, COL6A3 rs3790993 C/G, SEMA3C rs1058425 T/C, ACACA rs1714987 G/C, FASN rs59638227 G/A, EGFR rs2072454, EGFR rs2270247, EGFR rs730437, EGFR rs2075109, EGFR rs2075110, EGFR rs6944695, EGFR rs2075111, EGFR rs12718946, and combinations thereof.

In one embodiment, the patient is African American, and step (ii) comprises detecting the presence of at least one SNP within a gene selected from the group consisting of TP63, MET, WNT1 and combinations thereof, wherein the presence of the SNP is associated with an increased risk of developing prostate cancer in the African American patient. Suitably, the SNP may be selected from the group consisting of TP63 rs56197129, TP63 rs6795002, TP63 rs6782221, TP63 rs6795465, TP63 rs56413159, TP63 rs73199732, TP63 rs55851920, TP63 rs7616437, MET rs116458171, MET rs139335187, MET rs201395418, MET rs567033632, MET rs115628473, MET rs377420134, MET rs916941, MET rs138238598, MET rs6966012, MET rs115240747, MET rs114707545, MET rs115293079, MET rs149188493, and WNT1 rs855723.

In another embodiment, the patient is African American mail and the detecting comprises detecting a SNP listed in Table 1 or Table 13, wherein the SNP has an odds ratio (OR) of less than 1 indicating a decreased risk of developing prostate cancer, for example, at least one SNP within a gene selected from the group consisting of ALDH1A1, FN1, COL6A3, SEMA3C, ACACA, and FASN, for example, at least one SNP is selected from the group consisting of ALDH1A1 rs8187942, ALDH1A1 rs722921, FN1 rs11651 G/A, FN1 rs13652 C/T, COL6A3 rs36104025 G/C, COL6A3 rs3790993 C/G, SEMA3C rs1058425 T/C, ACACA rs1714987 G/C, FASN rs59638227 G/A and combinations thereof.

In a preferred embodiments, the patient is African American, and step (ii) comprises detecting the presence of the at least one SNP within the gene ALDH1A1, wherein the presence of the SNP is associated with a decreased risk of developing prostate cancer in the African American patient. Suitable SNPs include ALDH1A1 rs8187942 or ALDH1A1 rs722921, In some embodiments, the patient is a non-Hispanic white male, and step (ii) comprises detecting the presence of at least one SNP within the gene selected from the group consisting of EGFR, FN1, FASN, wherein the presence of the SNP is associated with an increased risk of developing prostate cancer in the non-Hispanic white male patient. Suitable SNPs include, for example, EGFR rs2072454, EGFR rs2270247, EGFR rs730437, EGFR rs2075109, EGFR rs2075110, EGFR rs6944695, EGFR rs2075111, EGFR rs12718946, FN1 rs11651 G/A, FN1 rs13652 C/T, COL6A3 rs36104025 G/C, FASN rs59638227 G/A, and combinations thereof.

In another embodiment, the patient is a non-Hispanic white male, and step (ii) comprises detecting the presence of at least one SNP within the gene COL6A3, SEMA3C, ACACA, wherein the presence of the SNP is associated with a decreased risk of developing prostate cancer in the non-Hispanic white male patient. Suitable SNPs include, for example, COL6A3 rs3790993 C/G, SEMA3C rs1058425 T/C, ACACA rs1714987 G/C, and combinations thereof.

Methods for selectively treating a subject with a higher risk for cancer are also provided. The methods include the step of detecting at least one SNP associated with a higher risk of cancer or a higher risk of aggressive cancer in the subject and treating the subject with a higher risk of cancer with at least one cancer therapy. Suitable SNPs include, for example, SNPs listed in Table 1, 2, 13 or 21, e.g., SNPs within the genes TP63, MET, WNT1, FN1, COL, FASN, EGFR, and combinations thereof. Suitable SNPs include, but are not limited to, e.g. TP63 rs56197129, TP63 rs6795002, TP63 rs6782221, TP63 rs6795465, TP63 rs56413159, TP63 rs73199732, TP63 rs55851920, TP63 rs7616437, MET rs116458171, MET rs139335187, MET rs201395418, MET rs567033632, MET rs115628473, MET rs377420134, MET rs916941, MET rs138238598, MET rs6966012, MET rs115240747, MET rs114707545, MET rs115293079, MET rs149188493, WNT1 rs855723,FN1 rs11651 G/A, FN1 rs13652 C/T, COL6A3 rs36104025 G/C, COL6A3 rs3790993 C/G, FASN rs59638227 G/A, EGFR rs2072454, EGFR rs2270247, EGFR rs730437, EGFR rs2075109, EGFR rs2075110, EGFR rs6944695, EGFR rs2075111, EGFR rs12718946, and combinations. In some embodiments, the patient is African American, and the SNP is a SNP associated with a higher risk of prostate cancer or more aggressive prostate cancer in an African American patient as detailed herein. In other embodiments, the patient is a non-Hispanic white male, and the SNP is an SNP associated with higher risk of prostate cancer or more aggressive prostate cancer as detailed herein Table 1 and 13 provides SNPs that are associated with a risk of developing prostate cancer in an AA or white male patient and can be used in the practice of the present invention. Suitable, SNPs associated with an increased risk of cancer in white males include, e.g. EGFR rs2072454, EGFR rs2270247, EGFR rs730437, EGFR rs2075109, EGFR rs2075110, EGFR rs6944695, EGFR rs2075111, EGFR rs12718946, FN1 rs11651 G/A, FN1 rs13652 C/T, COL6A3 rs36104025 G/C, FASN rs59638227 G/A, and combinations thereof. Suitable SNPs associated with an increased risk of cancer in AA include TP63 rs56197129, TP63 rs6795002, TP63 rs6782221, TP63 rs6795465, TP63 rs56413159, TP63 rs73199732, TP63 rs55851920, TP63 rs7616437, MET rs116458171, MET rs139335187, MET rs201395418, MET rs567033632, MET rs115628473, MET rs377420134, MET rs916941, MET rs138238598, MET rs6966012, MET rs115240747, MET rs114707545, MET rs115293079, MET rs149188493, and WNT1 rs855723.

Methods of detecting at least one SNP in a subject associated with tumor aggressiveness in a subject are provided. Suitably, the method comprises obtaining a sample from the subject and detecting the presence of at least one SNP that is associated with tumor aggressiveness as detailed in Example 4 and Tables 2 and 21. Suitable SNP in a gene selected from the group consisting of TP63, MET, WNT1, RELN, MYBPC1, NCOR2 and WDR4.

Further, methods of selectively treating a subject with aggressive prostate cancer are provided. The method comprises detecting at least on SNP in the subject that is associated with an increased risk of aggressive prostate cancer; and treating the subject having an aggressive prostate cancer with at least one cancer therapy. In some embodiments, the patient is African American and wherein the SNP is in a gene selected from TP63, MET, WNT1, MYBPC1, RELN, NCOR2, WDR4 and combinations thereof. In some embodiments, the SNP is an SNP selected from the SNPs in Table 2 or 21 which have an odds ratio of greater than 1. In some embodiments the patient is a non-Hispanic white male and wherein the SNP is rs2072454 (EGFR) or another SNP within EGFR.

Methods of determining prostate cancer survival of a patient are also provided. The method comprises detecting at least on SNP within a gene selected from Table 3 or described in Example, 3 (including SNPs listed therein). For example, the SNP within a gene selected from CD44, ABCC1, GDF15 and ITGB1 wherein the detection of at least one SNP is associated with prostate cancer survival. In one embodiment, the at least one SNP is selected from the group consisting of rs11009151 T, rs9666607 A, rs35605 C, rs212091 T and rs1058587 G; and is associated with an increased risk of death from prostate cancer. In some embodiments, the detecting at least three SNPs was associated with a higher risk of death from prostate cancer. In further embodiments, the patients with TC and TT genotypes of rs35605 and TC and CC genotypes of rs212091 had a decreased risk of death from prostate cancer and an increased survival rate.

The following non-limiting examples are included for purposes of illustration only, and are not intended to limit the scope of the range of techniques and protocols in which the compositions and methods of the present invention may find utility, as will be appreciated by one of skill in the art and can be readily implemented.

EXAMPLE 1

The embodiment described here demonstrates genetic variants of CD44-related stemness pathway genes in risk of prostate cancer Background Evidence suggests that cells having a stemness phenotype play an important role in cancer initiation. Prostate cells having a stemness phenotype, characterized by proliferation, self-renewal and pluripotency have been identified. CD44 has been extensively reported for its critical role in regulation of stemness. In the present study, we explored associations between genetic variants in 25 CD44-related stemness pathway genes and prostate cancer (PCa) risk in two racial groups by analyzing published genome-wide association studies (GWASs) of PCa.

Methods

We used two non-Hispanic white GWAS datasets from the Prostate, Lung, Colorectal and Ovarian (PLCO) Cancer Screening Trial and the Breast and Prostate Cancer Cohort Consortium (BPC3) and two African GWAS datasets from the Multiethnic/Minority Cohort Study of Diet and Cancer (MEC) and the Ghana Prostate Study. First, we evaluated associations of 5,075 single-nucleotide polymorphisms (SNPs) in 25 CD44-related stemness pathway genes with PCa risk in 1,609 cases and 2,550 controls of non-Hispanic whites. Second, we determined the heterogeneity in risk associated with the SNPs in 1,144 cases and 1,116 controls of African ancestry. Third, we performed in silico bioinformatics and SNP-mRNA expression correlation analyses to investigate potential functions of the SNPs.

Results

We identified eight intronic SNPs in ACPP and EGFR with consistent effects on PCa risk in both populations. We found 141 SNPs in seven genes (ACPP, TP63, ITGA1, EGFR, NOTCH1, CD44, ABCC1 and ERG) with heterogeneity in the two different racial populations. After bioinformatics analyses, six SNPs in three genes (ACPP, ITGA1 and EGFR) were predicted to be functional: three variants in exon regions were predicted to play a role in splicing regulation, ITGA1 rs2279587 G>A, ITGA1 rs12520591 T>G and EGFR rs2072454 T>C; two variants located in EGFR 3'UTR were both predicted to have miRNA binding affinity, rs10228436 G>A and rs10277413 T>G; one variant in ACPP rs218699 C>T annotated within the transcription binding sequence. After linkage disequilibrium analysis, four independent SNPs (r5218699, rs12520591, rs2075454 and r510228436) were selected as tags. Among these, EGFR rs2072454 T>C showed significant associations with opposite effects on PCa risk in different populations [adjusted odd ratio (adjOR)=1.21, 95% confident interval (CI)=1.09-1.34, P=3.47E-04 for non-Hispanic whites; adjOR=0.86, 95% CI=0.76-0.97, P=0.017 for Africans].

Conclusions

Six functional SNPs in the CD44-related stemness pathway genes, ITGA1 rs2279587 G>A, ITGA1 rs12520591 T>G, EGFR rs2072454 T>C, EGFR rs10228436 G>A, EGFR rs10277413 T>G; ACPP rs218699 C>T showed heterogeneity in non-Hispanic white and African populations in association with PCa risk. These genetic variants may serve as novel biomarkers that reveal molecular mechanisms underlying the observed racial differences in PCa risk.

EXAMPLE 2

The embodiment described here demonstrates that single-nucleotide polymorphisms of race-related alternatively spliced genes are associated with prostate cancer risk, aggressiveness and/or survival.

Background

African American (AA) men exhibit nearly 2-fold higher incidence and 3-fold higher mortality rates from prostate cancer (PC) compared with white men. This disparity likely results from a complex interplay between behavioral, social, neighborhood and biological factors, which all work collectively to generate increased tumor aggressiveness in AAs. Recent data from our laboratory, evaluating human PC biopsy tissue led to the identification of alternative splicing events between AA and white PC that track with increased growth and more aggressive invasion characteristics of PC in AA men. In the present study, we explored associations between genetic variants of 30 such alternatively spliced genes and PC risk, aggressiveness and survival in white and AA groups by analyzing published genome-wide association studies (GWAS) of PC.

Methods

We used GWAS datasets from the Multiethnic Cohort Study of Diet and Cancer (MEC), including AA PC cases and controls, and the Prostate, Lung, Colorectal, and Ovarian Cancer Screening Trial (PLCO), including white PC cases and controls, to evaluate associations of 11,073 and 10,385 single-nucleotide polymorphisms (SNPs), respectively, in 30 genes identified to be alternatively spliced between white and AA PC with PC risk, aggressiveness and survival. For risk, we evaluated 1150 cases and 1101 controls in PLCO and 670 cases and 658 controls in MEC, for aggressiveness, we evaluated 237 aggressive and 843 non-aggressive in PLCO and 234 aggressive and 436 non-aggressive in MEC, and for survival, we evaluated 1150 overall, 237 aggressive and 843 non-aggressive in PLCO. We then performed in silico bioinformatics to investigate potential functions of the SNPs.

Results

Significant associations between SNPs in FN1, COL6A3 and ACACA and SNPs in SEMA3C and FASN and PC risk in white and AA populations, respectively, were identified. In addition, SNPs in ACACA and SNPs in SEMA3C, RELN, MYBPC1, NCOR2 and WDR4 were found to be significantly associated with PC aggressiveness in white and AA populations, respectively. Furthermore, significant associations between SNPs in RHOU, FN 1, COL6A3, SEMA3C, RELN, CD44, LMO7 and WDR4 and PC survival in a white population were identified. All of the aforementioned SNPs were predicted to play a role in splicing regulation.

Conclusions

SNPs of race-related alternatively spliced genes that are predicted to play a role in splicing regulation are significantly associated with PC risk, aggressiveness and/or survival in white and/or AA populations. Such variants have the potential to serve as novel molecular targets and biomarkers of increased risk of aggressive PC or therapeutics against aggressive PC. Ultimately, such biomarkers and therapeutic agents could serve as novel precision medicine interventions, reducing the mortality burden from PC among AA men.

EXAMPLE 3

Studies suggest that a stemness phenotype contributes to cancer initiation, progression and lack of treatment efficacy, and thus a poor prognosis. The present Example identifies five single nucleotide polymorphisms (SNPs) of prostate cancer-related stemness pathway genes that are associated with prostate cancer survival and are predicted to play roles in RNA splicing regulation, miRNA binding site activity, protein activity or transcription factor binding. These findings further support a mechanistic link between a stemness phenotype and poor cancer prognosis. The SNPs identified here may serve as novel precision biomarkers that have prognostic significance for prostate cancer in distinguishing aggressive from indolent disease at the time of screening and diagnosis. In addition, the prostate cancer-related stemness pathway genes in which the SNPs have been identified may serve as novel molecular targets for developmental therapeutics against aggressive prostate cancer.

Purpose

Prostate cancer is a clinically and molecularly heterogeneous disease, with a wide variation in outcomes that are only partially predicted by grade and stage. Additional prognostic tools distinguishing indolent from aggressive disease are needed. Evidence suggests that phenotypic characteristics of stemness are correlated with poor cancer prognosis. Given this correlation, we identified single nucleotide polymorphisms (SNPs) of stemness pathway genes and examined their associations with survival of prostate cancer patients.

Experimental Design

SNPs within stemness pathway genes were analyzed for association with overall survival of prostate cancer in 1,150 prostate cancer patients enrolled in the Prostate, Lung, Colorectal and Ovarian Cancer Screening Trial. Those significant SNPs predicted to be functional were selected for linkage disequilibrium analysis and combined and stratified analyses. Internal validation was performed. Validated SNPs were evaluated for association with corresponding gene expression.

Results

SNPs of the CD44 (r59666607), ABCC1 (r535605 and r5212091), GDF15 (r51058587) and ITGB1 (r511009151) genes were associated with prostate cancer survival and were predicted to be functional. Specifically, a role for rs9666607 of CD44 and rs35605 of ABCC1 in splicing regulation, rs212091 of ABCC1 in miRNA binding site activity, rs1058587 of GDF15 in causing an amino acid change in the GDF15 protein and rs11009151 of ITGB1 in affecting transcription factor binding was predicted.

Conclusions rs9666607 of CD44, rs35605 and rs212091 of ABCC1, rs1058587 of GDF15 and rs11009151 of ITGB1 represent novel prognostic markers for overall survival of prostate cancer. These findings support a contribution of the stemness pathway to prostate cancer patient outcome.

Given the previous identification of germline SNPs that are associated with prostate cancer prognosis, it is likely that identifying genetic variation in additional oncogenic signaling pathways will lead to novel tools for prostate cancer prognosis. In the post-genomic and post-GWAS era, it is possible to take a hypothesis-driven, targeted pathway-based, multigene approach to identify genetic variation in an oncogenic signaling pathway and its association with cancer survival. Given the potential of prostate cells having a stemness phenotype to portend a poor prognosis, it is likely that genetic variation contributing to this phenotype could serve as novel precision biomarkers that have prognostic significance for prostate cancer in distinguishing aggressive from indolent disease at the time of screening and diagnosis and/or as novel molecular targets for developmental therapeutics against aggressive prostate cancer. To elucidate such genetic variation, we applied a hypothesis-driven, targeted pathway-based, multigene approach to identify SNPs of CD44-related stemness pathway genes and examine their associations with survival of prostate cancer patients using available genotyping data from the Prostate, Lung, Colorectal and Ovarian Cancer Screening Trial (PLCO) (27).

Materials and Methods

Study Population

The current study included 1,150 prostate cancer cases that were diagnosed among men enrolled in the PLCO cohort (27). The PLCO originally enrolled 77,500 men and 77,500 women aged 55 to 74. It is a National Cancer Institute (NCI)-funded, multicenter, randomized trial focused on screening for cancer at ten medical centers in the United States between 1993 and 2011. The PLCO collected blood specimens from the first screening visit, gathered extensive information about each participant and followed all participants for at least 13 years after enrollment. Genomic DNA extracted from the blood samples was genotyped using Illumina HumanHap300v1.1 and HumanHap250Sv1.0 (dbGaP accession: phs000207.v1.p1) (28). Tumor staging was determined according to the 5$^{th}$ edition American Joint Committee on Cancer (AJCC) staging system. The follow-up time was defined from prostate cancer diagnosis to the date of last follow-up or time of death. We used overall survival (OS) of prostate cancer as the primary endpoint of the current study. The institutional review boards of each participating institution approved the PLCO and the use of biospecimens for further research, and all subjects signed a written informed consent. The current analyses were conducted after application to and approval from the NIH/NCI.

Gene and SNP Selection

Based on the online database Genecards (http://http://www.genecards.org//), 25 CD44-related stemness pathway genes that reportedly play a role in prostate cancer were selected, using the search terms "prostate cancer stem cell" (Table 7). Genotyped SNPs within these genes and their ±2-kb flanking regions were selected for association analysis. There were available data for 635 genotyped SNPs of the aforementioned 25 genes in PLCO. SNPs were selected by using the following criteria: SNPs located on autosomal chromosomes; minor allelic frequency (MAF)≥5%; a genotyping rate≥95% and Hardy-Weinberg equilibrium (HWE) ≥1×10$^{-6}$. As a result, 635 genotyped SNPs of the aforementioned 25 genes were extracted from the PLCO prostate cancer GWAS data (dbGaP accession: phs000207.v1.p1). Nineteen genotyped SNPs of ten of the aforementioned genes showed an association with prostate cancer overall survival and passed multiple testing correction by the false positive report probability (FPRP) method that is independent of the number of tests. These ten gene regions were further imputed, filtering the imputed SNPs with the criteria of MAF≥5%, genotyping rate≥95% and HWE≥1×10$^{-6}$. Subsequently, 3,848 qualified imputed SNPs were identified and tested for their associations with the survival of prostate cancer patients. The functional relevance of the SNPs was predicted by SNPinfo and RegulomeDB, which are publically available online tools. SNPinfo incorporates functional predictions of protein structure, gene regulation, splicing and microRNA binding (29). RegulomeDB was used to identify the SNPs with previously reported links to expression quantitative trait loci (eQTL) labeled within a score of "1" (30).

Statistical Analysis

Figure 4:
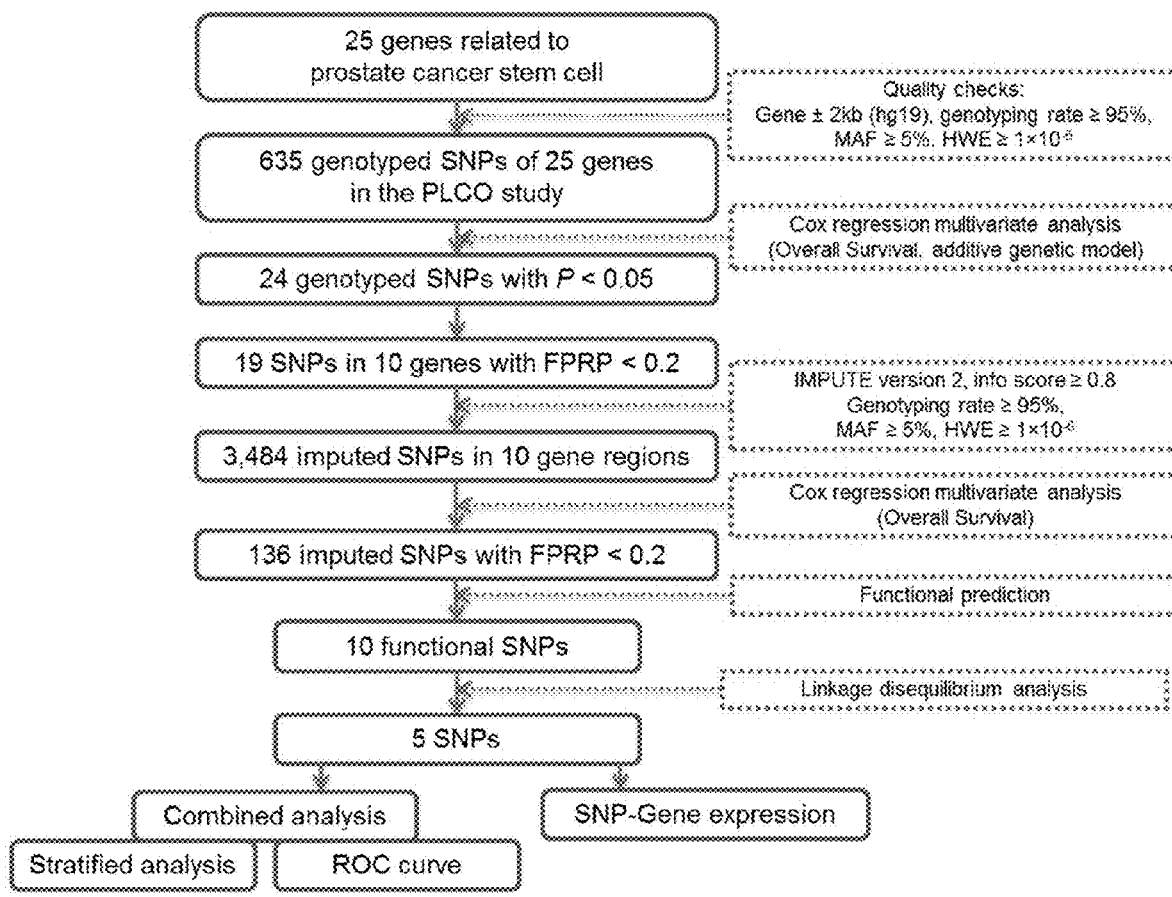
FIG. 4 Overall flowchart. Abbreviations: PLCO: The Prostate, Lung, Colorectal and Ovarian Cancer Screening Trial; SNP: Single nucleotide polymorphism; FPRP: False positive report probability; MAF: Minor allele frequency; HWE: Hardy-Weinberg equilibrium; ROC: Receiver operating characteristic.

FIG. 4 provides a flow chart that outlines the analyses. Briefly, Cox proportional hazards regression models were completed for each of the SNPs related to the 25 Prostate Cancer Stem Cell-related genes. For multiple testing corrections, the FPRP approach was used with a cut-off value of 0.2 to lower the probability of false positive findings (31). Imputation was then performed with IMPUTE2 according to the European population from the 1000 Genomes Project (phase 1 release V3) (32). Imputed SNPs with info value≥0.8 were qualified for further analysis. Following imputation, Cox multiple regression models were again applied as well as multiple testing correction. Further filtering was completed using functional prediction utilizing SNPinfo and eQTL annotation of RegulomeDB. Pairwise linkage disequilibrium (LD) was estimated by using the data from 373 European individuals in the 1000 Genomes Project. The number of effect genotypes was summarized to evaluate the combined effects of all the independent SNPs.

Kaplan-Meier curves and log-rank tests were used to evaluate the associations between genotypes and OS. The heterogeneity of associations between subgroups in stratified analyses was assessed using the $\chi^2$-based Q-test. Cox regression models were used to estimate the hazards ratio (HR) and 95% confidence interval (CI) for the associations of demographic and clinical characteristics with OS. Associations between SNPs and OS (in additive genetic models) were obtained by both univariate and multivariable Cox regression analyses performed by using the GenABEL package of R software, with adjustments for age, Gleason score, stage and primary treatment (33). In selecting our final multivariable model, we combined risk alleles of the final set of independent SNPs into genetic "scores" to test their joint effects on prostate cancer survival. All patients were allocated into eight groups, with one to eight risk alleles. Final model selection was completed based on the lowest Akaike information criterion (AIC) (34). A time-dependent receiver operating characteristic (ROC) analysis was performed to calculate area under curve (AUC) of SNPs and clinical characteristics in a ⅔ training set and in a randomly selected ⅓ testing set by using "survAUC" package of R software (35). As an internal validation, the final model was replicated in 1000 bootstrap samples, where in each cohort sampled, a random ⅔ training set and ⅓ testing set were analyzed. We reported the mean bootstrap AUC, and 95% confidence intervals of the AUC for 1, 3, and 5-year survival, as well as the bootstrap P-value comparing the model with clinical variables alone to clinical+genomic variables in 1000 bootstrap training sets.

In analyzing associations between SNPs and corresponding gene expression, we performed linear regression analysis using R software. Gene expression levels were obtained from the HapMap 3 project using Illumina Human-6 v2 Expression BeadChip, including 107 Northern Europeans from Utah (CEU), 242 Han Chinese in Beijing, China (CHB), 41 individuals of Mexican (MEX) ancestry and 326 individuals of African (AFR) ancestry (36). All statistical analyses were calculated using SAS software (version 9.1.3; SAS Institute, Cary, N.C., USA) unless otherwise specified.

Results

Basic Characteristics of the Study Population

The overall workflow of the current study is summarized in FIG. 4. Basic characteristics of 1,150 prostate cancer patients from the PLCO are described in Table 4. The median age of the patients was 67 years. Of these 1,150 patients, 215 (18.7%) were deceased at the last follow-up (Table 4). In multivariate analyses, five of the six selected variables were found to be significantly associated with prostate cancer OS. These variables were age at diagnosis (HR=1.80, >67 vs. ≤67), Gleason score (HR=2.52, ≥8 vs. 2-6), tumor stage (HR=1.76, III/IV vs. I/II), aggressiveness (HR=1.89, non-aggressive vs. aggressive) and treatment (HR=2.06, 1.56, 4.28, and 2.68 for radiotherapy alone, radiotherapy+hormone therapy, hormone therapy alone and other treatments vs. radical prostatectomy, respectively).

Multivariate Analyses of Associations Between SNPs and Prostate Cancer OS

Figure 5:
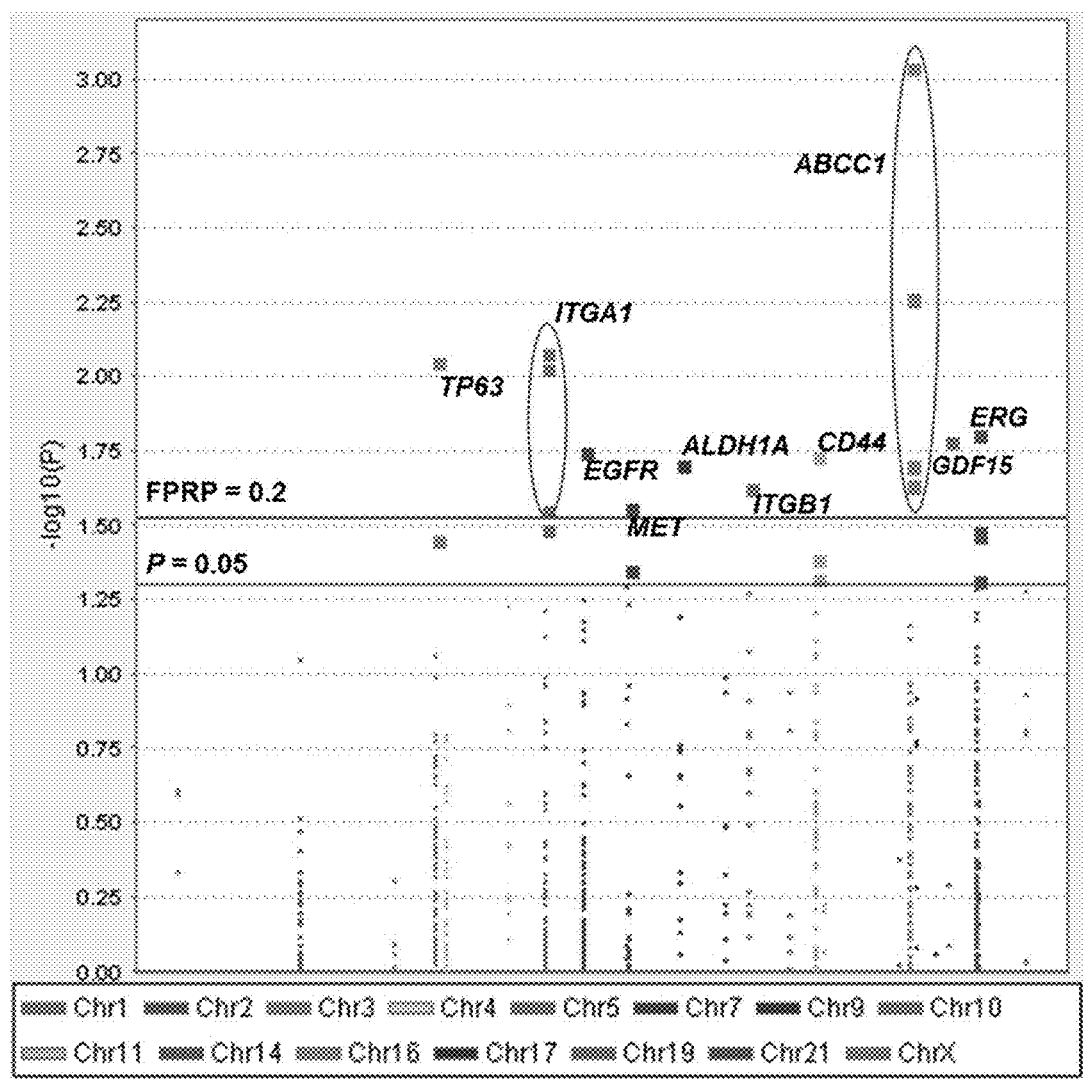
FIG. 5 Manhattan plot of the genotyped data from the PLCO study. The statistical values across the chromosomes of association between 635 SNPs in 25 genes and prostate cancer overall survival are plotted as −log 10 P values. The blue horizontal line indicates P=0.05 and the red line indicates false positive report probability (FPRP)=0.2.
Figure 6:
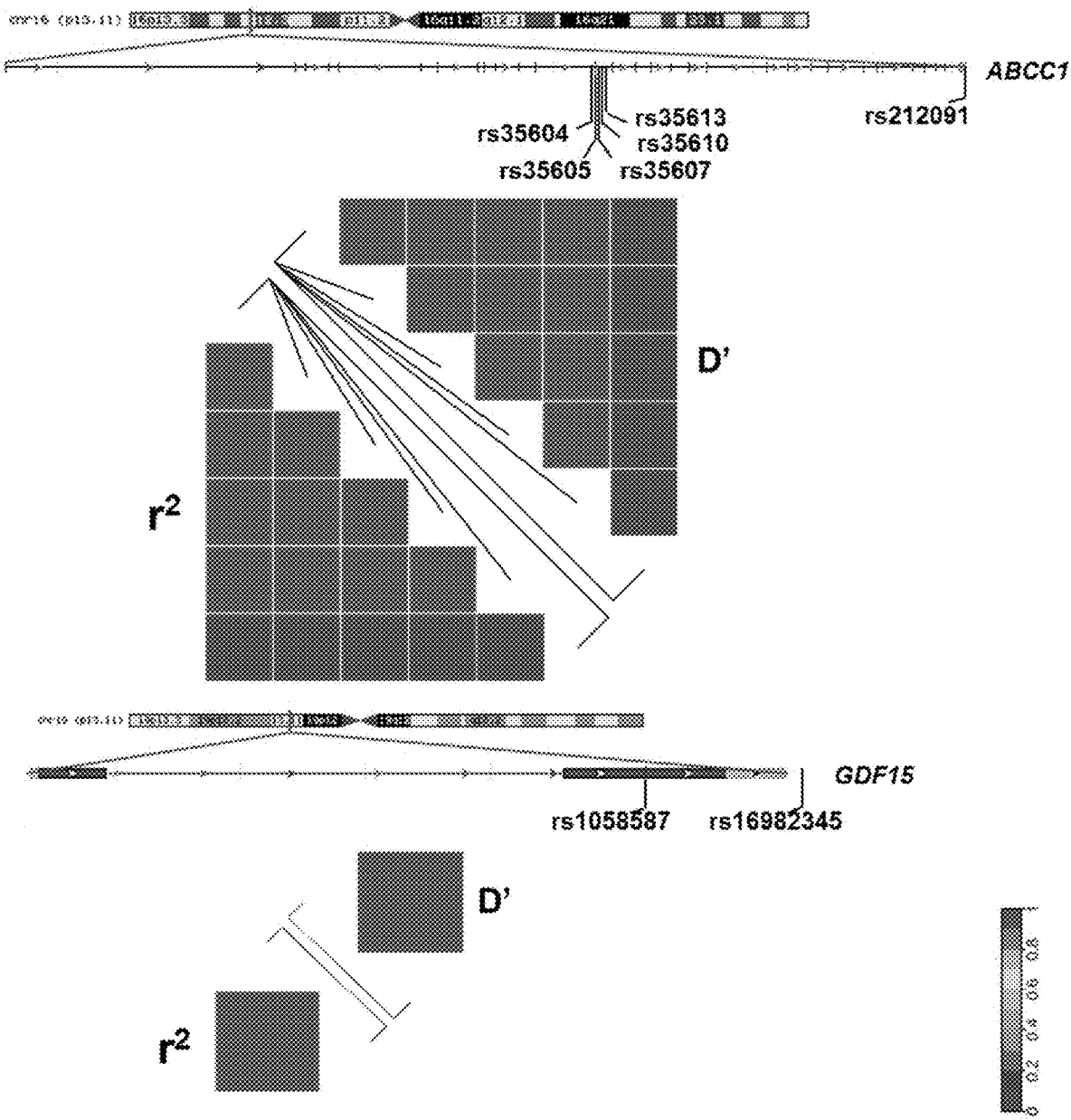
FIG. 6 Linkage disequilibrium plots of the selected SNPs on ABCC1 and GDF15 by using data from European individuals of the 1000 Genomes Project.
Figure 7A:
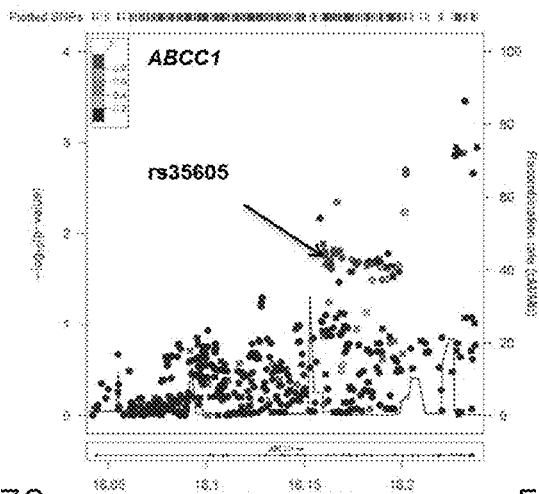
FIG. 7A Regional association plots of the five independent and significant SNPs based on imputation data from the PLCO study. The left-hand Y-axis shows the −log 10 P-value of each SNP, which is plotted according to the chromosomal base-pair position. The genome build and linkage population were plotted according to the hg19/1000 Genomes European. The right-hand Y-axis shows the recombination rate estimated from the recombination rate estimated for European populations from the HapMap Data Rel 22/phase II.
Figure 7B:
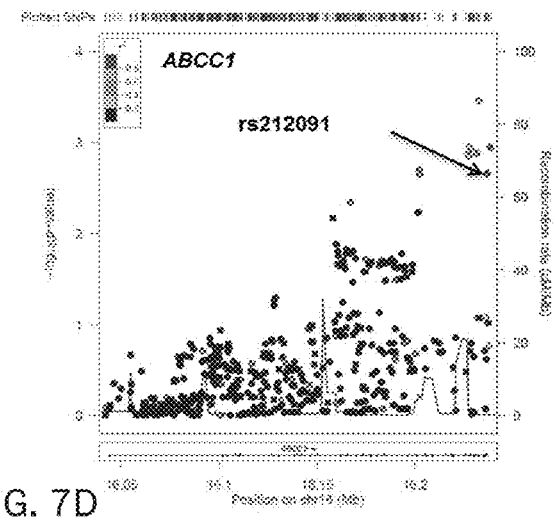
FIG. 7B Regional association plots of the the five independent and significant SNPs based on imputation data from the PLCO study. The left-hand Y-axis shows the −log 10 P-value of each SNP, which is plotted according to the chromosomal base-pair position. The genome build and linkage population were plotted according to the hg19/1000 Genomes European. The right-hand Y-axis shows the recombination rate estimated from the recombination rate estimated for European populations from the HapMap Data Rel 22/phase II.
Figure 7C:
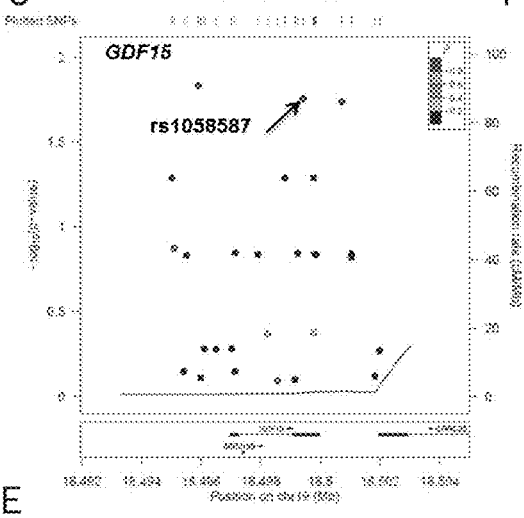
FIG. 7C Regional association plots of the the five independent and significant SNPs based on imputation data from the PLCO study. The left-hand Y-axis shows the −log 10 P-value of each SNP, which is plotted according to the chromosomal base-pair position. The genome build and linkage population were plotted according to the hg19/1000 Genomes European. The right-hand Y-axis shows the recombination rate estimated from the recombination rate estimated for European populations from the HapMap Data Rel 22/phase II.
Figure 7D:
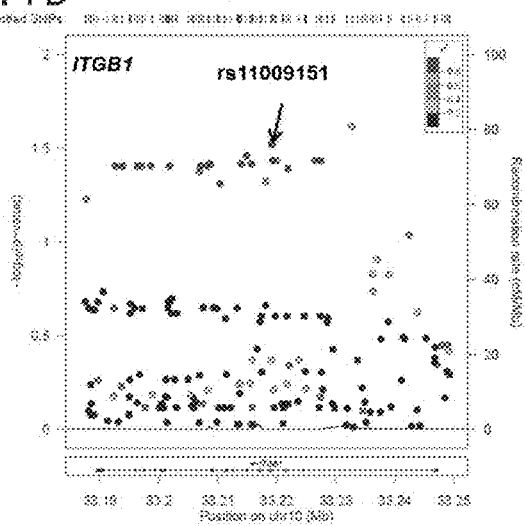
FIG. 7D Regional association plots of the the five independent and significant SNPs based on imputation data from the PLCO study. The left-hand Y-axis shows the −log 10 P-value of each SNP, which is plotted according to the chromosomal base-pair position. The genome build and linkage population were plotted according to the hg19/1000 Genomes European. The right-hand Y-axis shows the recombination rate estimated from the recombination rate estimated for European populations from the HapMap Data Rel 22/phase II.
Figure 7E:
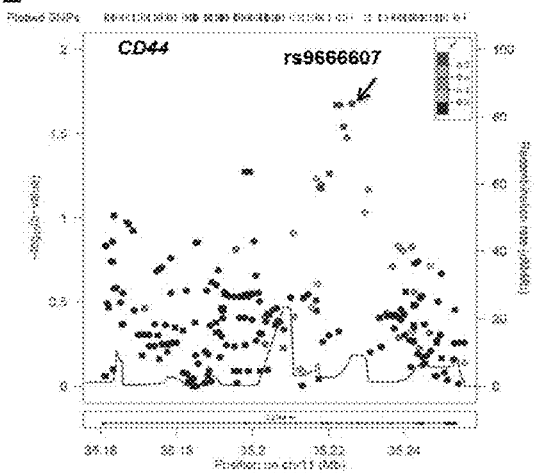
FIG. 7E Regional association plots of the the five independent and significant SNPs based on imputation data from the PLCO study. The left-hand Y-axis shows the −log 10 P-value of each SNP, which is plotted according to the chromosomal base-pair position. The genome build and linkage population were plotted according to the hg19/1000 Genomes European. The right-hand Y-axis shows the recombination rate estimated from the recombination rate estimated for European populations from the HapMap Data Rel 22/phase II.
Figure 8A:
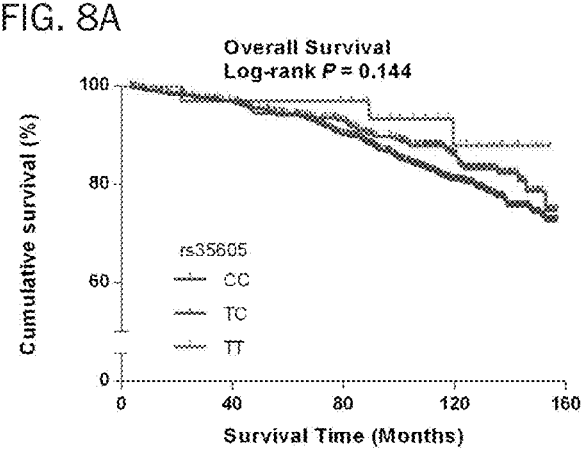
FIG. 8A Kaplan-Meier survival curves of prostate cancer patients according to genotypes of the five independent and significant SNPs, FIG. 8A depicting SNP rs35605 in ABCC1.
Figure 8B:
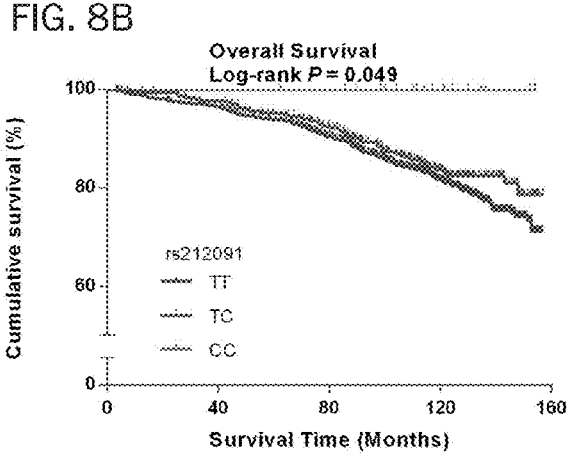
FIG. 8B Kaplan-Meier survival curves of prostate cancer patients according to genotypes for SNP rs212091 in ABCC1.
Figure 8C:
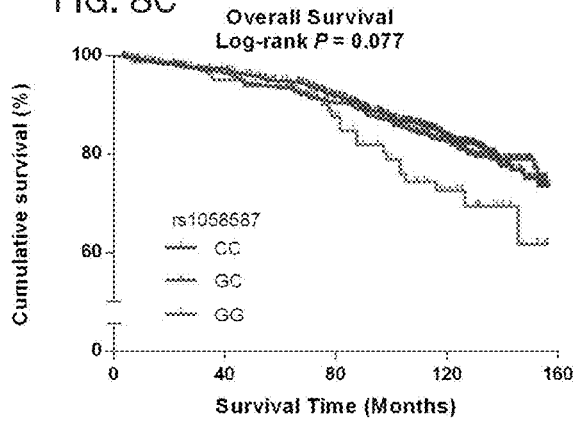
FIG. 8C Kaplan-Meier survival curves of prostate cancer patients according to genotypes for SNP rs1058587 in GDF15.
Figure 8D:
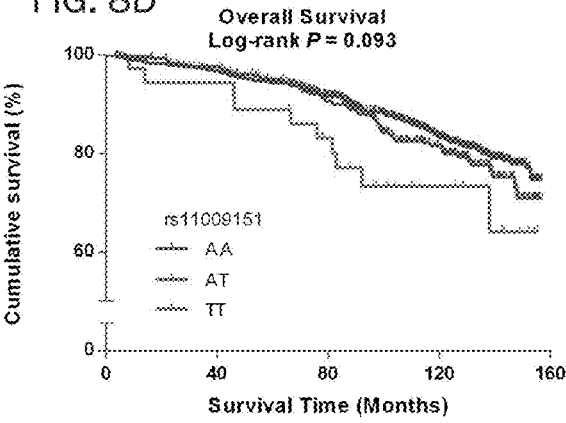
FIG. 8D Kaplan-Meier survival curves of prostate cancer patients according to genotypes for SNP rs11009151 in ITGB1.
Figure 8E:
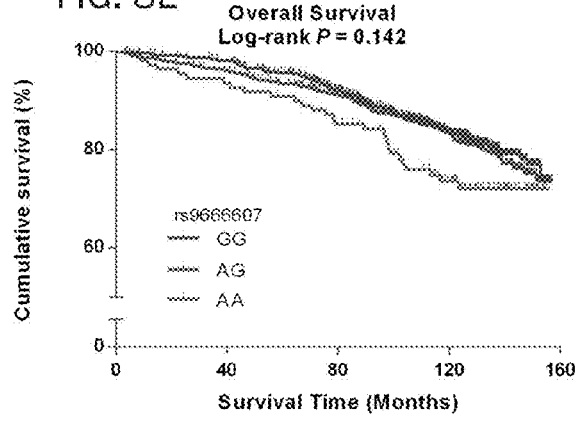
FIG. 8E Kaplan-Meier survival curves of prostate cancer patients according to genotypes for SNP rs9666607 in CD44.

Multivariate Cox models were used to assess the associations of 635 genotyped SNPs with OS controlling for age, Gleason score, stage and primary treatment (as summarized in the Manhattan plot, FIG. 5). Of these 635 SNPs, 24 SNPs were individually significantly associated with OS at P<0.05 in an additive genetic model. After adjustment for multiple testing, 19 SNPs in ten genes (TP63, ITGA1, EGFR, MET, ALDH1A1, ITGB1, CD44, ABCC1, GDF15 and ERG) remained statistically significant, with FPRP<0.2 (Table 8). After imputation and quality checks for SNP inclusion, as aforementioned, 136 of the 3,848 imputed SNPs of these ten genes remained significantly associated with prostate cancer OS (Table 9). Among these 136 SNPs, ten SNPs with potential functions predicted by SNPinfo and eQTL annotation of RegulomeDB were selected for further analyses (Table 9).

LD Analysis of the Ten Imputed SNPs

In the LD analysis of the ten imputed SNPs predicted to be functional, five SNPs of ABCC1 (r535604, rs35605, rs35607, rs35610 and r535613) and two SNPs of GDF15 (rs1058587 and rs16982345) were in high LD, respectively (all $r^2$>0.8) (FIGS. 6 and 7A-7E). Compared to the high LD SNPs of the corresponding genes, rs35605 of ABCC1 and rs1058587 of GDF15 exhibited more functional relevance, and both were located in exonic regions (Table 5). Therefore, rs35605, rs1058587 and three other SNPs (r5212091, rs11009151, and r59666607) were chosen as independent SNPs for additional analyses.

Combined and Stratified Analyses of the Five Independent SNPs

The minor allele of rs35605 and rs212091 of ABCC1 were found to be associated with better OS of prostate cancer, with a variant-allele attributed HR of 0.71 (95% CI: 0.53-0.94, P=0.018) and 0.61 (95% CI: 0.45-0.83, P=0.002), respectively (Table 10). Compared with their corresponding reference genotypes in a dominant genetic model, patients with TC and TT genotypes of rs35605 and TC and CC genotypes of rs212091 had a decreased risk of death (HR=0.71, 95% CI=0.51-0.97 and P=0.034; HR=0.63, 95% CI =0.45-0.87 and P=0.006, respectively; Table 10). Meanwhile, minor alleles of rs11009151 of ITGB1, rs9666607 of CD44 and rs1058587 of GDF15 were associated with a worse OS from prostate cancer in an additive genetic model, with HR of 1.31 (95% CI: 1.03-1.67, P=0.026), 1.28 (95% CI: 1.04-1.58, P=0.018), and 1.29 (95% CI: 1.05-1.59, P=0.015), respectively (Table 10). Compared with the reference genotypes in a recessive genetic model, patients with risk genotypes of the three SNPs had an increased risk of death (RR=1.74 and P=0.015 for rs11009151, HR=1.86 and P=0.002 for rs9666607, HR=1.71 and P=0.015 for rs1058587, respectively; Table 10).

Figure 1B:
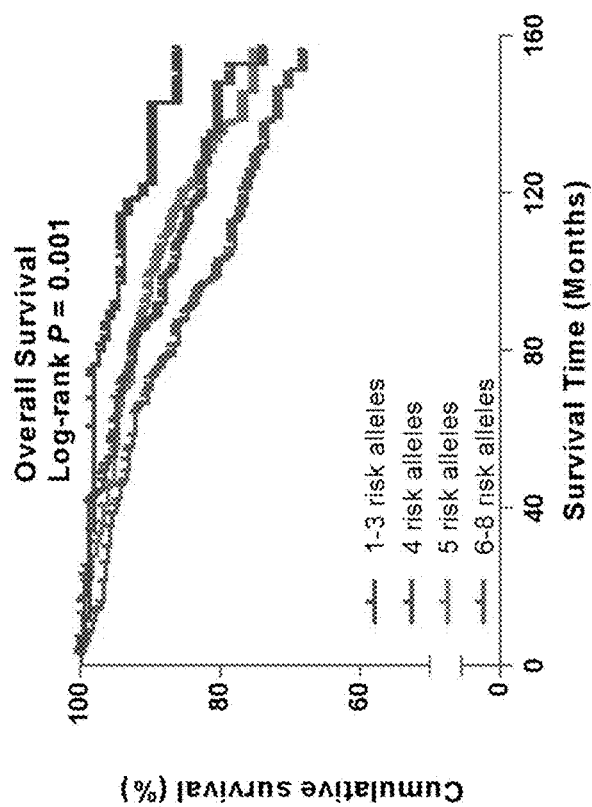
FIG. 1B Kaplan-Meier survival curves of prostate cancer patients according to combined risk alleles of the five independent and significant SNPs.

In Table 6, we assessed three models that combined the risk alleles utilizing different groupings. Based on the Akaike information criterion (AIC), the model that trichotomized all patients into low, medium and high-risk groups (patients with 1-3, 4-5 and 6-8 risk alleles, respectively) was preferred. In this model, an increase in per-unit risk score was associated with an increased risk of death after adjustments (HR=1.82, 95% CI=1.46-2.27, P=1.05×10$^{-7}$, Table 6). Compared with the low-risk group, the medium-risk group had a 2.45-fold increased risk of death (HR=2.45, 95% CI=1.39-4.30, P=0.002, Table 6), and the group with highest number of risk alleles had a notably 4.00-fold increased risk of death (HR=4.00, 95% CI=2.25-7.12, P=2.41×10$^{-6}$, Table 6). To visualize the HR effects, we present Kaplan-Meier survival curves of the association between OS and genotypes on the five SNPs in FIG. 8 and the combined effects in FIGS. 1A-1B.

In subgroup analyses of patients with different risk scores, which were stratified by age, PSA before diagnosis, Gleason score, stage, aggressiveness or types of primary treatments, we found no significant evidence for heterogeneity across strata except for age group, with a suggestion of an even worse OS of patients with older age (P for heterogeneity=0.014, Table 11). For each independent SNP in stratified analysis, we observed heterogeneity in the age group for ABCC1 rs212091 (P for heterogeneity=0.037, Table 12). In the subgroup of older age, patients carried the protective allele C of rs212091 showed a better survival, which means the allele T was associated with an increased risk of death (Table 12).

ROC Curve and Internal Validation

Figure 2A:
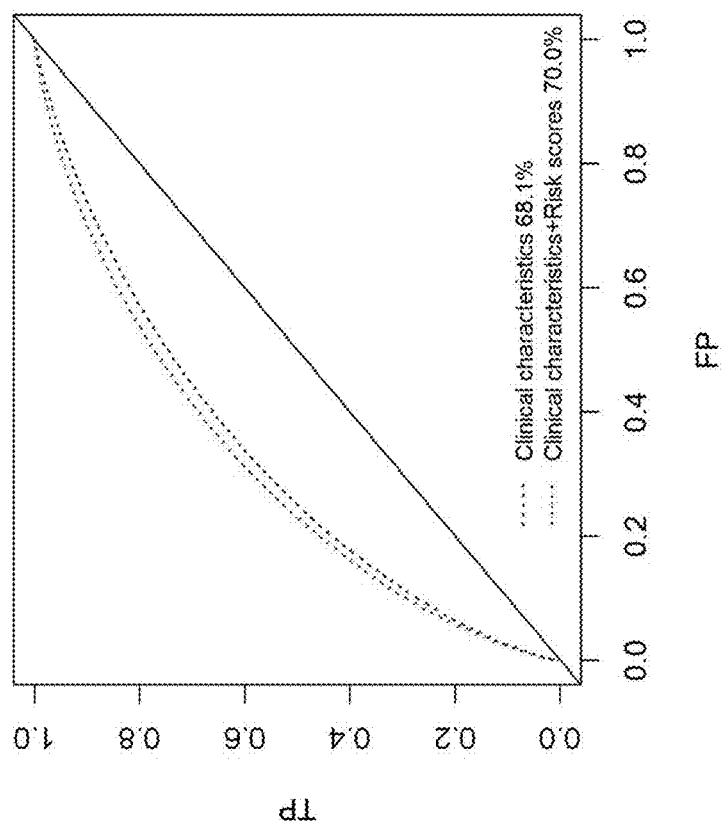
FIG. 2A Receiver-operating characteristic (ROC) curves for prediction of prostate cancer survival based on only clinical characteristics (age, Gleason score and tumor stage) or additionally combined effect genotypes, time-dependent area under curve (AUC).
Figure 2B:
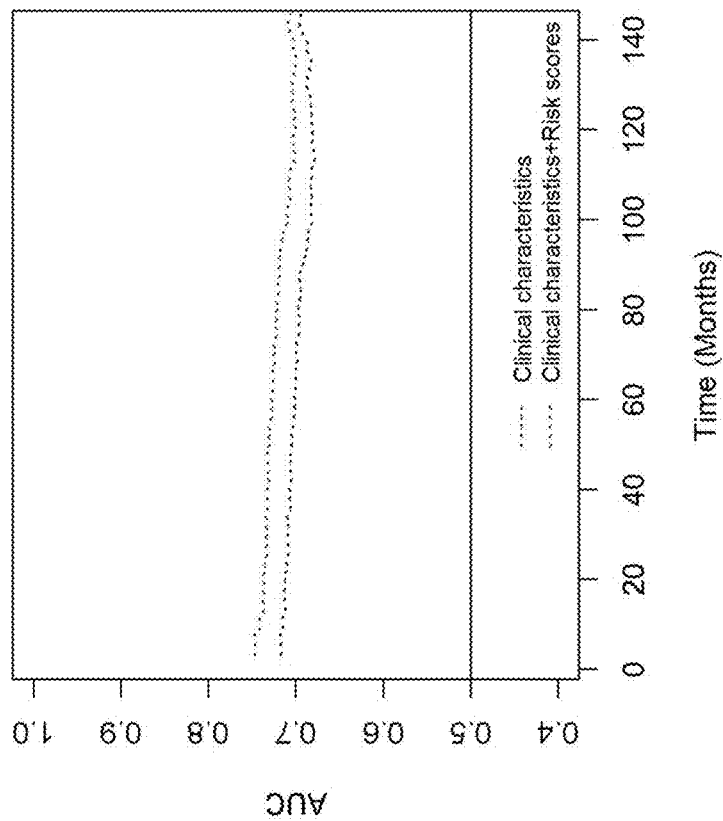
FIG. 2B Receiver-operating characteristic (ROC) curves for prediction of prostate cancer survival based on only clinical characteristics (age, Gleason score and tumor stage) or additionally combined effect genotypes, ROC curves corresponding to the time point of ten-year.

We further evaluated combined risk scores for their potential to predict prostate cancer OS by a time-dependent ROC. As shown in FIG. 2A, the AUC based on both trichotomized risk scores and clinical characteristics was greater than that with only clinical characteristics at different time points. The AUC of the ten-year survival models increased from 68.1% to 70.0% after adding the genetic scores to the clinical characteristics (FIG. 2B). The bootstrap mean AUC and 95% CIs for three-year survival were 73.2 (68.0-78.4) for clinical variables only, and 75.4 (70.4-80.3) for clinical plus genetic scores, bootstrap P-value=0.017; similarly, for five-year survival, 72.3 (67.6-76.8) for clinical variables only, and 74.5 (70.0-79.0) for clinical plus genetic, bootstrap P-value=0.011; and finally, for ten-year survival, 69.8 (65.9-73.6) for clinical variables only, and 71.9 (68.3-75.5) for clinical plus genetic scores, bootstrap P-value, P=0.004. The bootstrap mean HR was similar to the original data reported in Table 6, 1.86, with 95% bootstrap CI (1.39-2.48).

The Five Independent SNPs and mRNA Expression of the Related Genes

All five independent SNPs showed some evidence of functional relevance using online prediction tools, including SNPinfo and RegulomeDB. Both rs35605 of ABCC1 and rs9666607 of CD44 were located in exonic regions and predicted to play a role in splicing regulation by SNPinfo. The intronic SNP of ITGB1, rs11009151, had a RegulomeDB score of "1f", which was eQTL for genes and within the functional annotation of most confidence. Another SNP of ABCC1 was located in the 3' untranslated region (UTR) and predicted by SNPinfo to affect miRNA-binding site activity. The non-synonymous SNP (nsSNP) of GDF15 could result in an amino acid substitution of the corresponding protein product. To provide biological support for the observed associations and predictions, we evaluated the correlation between genotypes of the five independent SNPs and their related mRNA expression levels using mRNA expression data of the 716 individuals in the HapMap3 Project. Except for rs1058587 of GDF15, the other four SNPs were found to be significantly associated with the related mRNA expression (P=0.019 for rs35605 and ABCC1, P=0.014 for rs212091 and ABCC1, P=0.007 for rs9666607 and CD44, and P=0.011 for rs11009151 and ITGB1, FIG. 3). Moreover, individuals with the minor alleles of all these four SNPs showed a higher relative mRNA expression level, compared with other subjects. These findings suggested that these four independent SNPs could modulate gene expression levels, thus having functional consequences.

Discussion

In the present study, we examined whether SNPs of the CD44-related stemness pathway genes are associated with survival of prostate cancer patients using available genotyping data from the PLCO. After adjusting for age, Gleason score, stage and primary treatment, we identified five independent SNPs of the CD44, ABCC1, GDF15 and ITGB1 genes that are predicted to be functional and associated with prostate cancer survival. In addition to the role of CD44, ABCC1, GDF15 and ITGB1 in stemness, these genes also play additional roles in tumor cell biology. Specifically, CD44, which encodes cluster of differentiation 44 is a transmembrane glycoprotein (37). In the context of tumor cell biology, increased CD44 expression has been associated with metastasis and prognosis. Through its ligands, CD44 mediates cellular adhesion, migration, innate immunity, wound healing, cancer progression, metastasis and activation of a multitude of oncogenic signaling pathways and transporters. Activation of these oncogenic signaling pathways and transporters mediates cellular proliferation, migration, invasion, survival and therapeutic resistance. Consistent with the aforementioned roles of CD44, the CD44 rs9666607 G/A variant was associated with prostate cancer survival in the present study. There is much evidence that the CD44 gene undergoes alternative splicing. The aforementioned expression of CD44 in normal and cancer cells and CD44-mediated biological processes has been attributed to distinct CD44 isoforms. In the context of prostate cancer, androgens and the androgen receptor have been shown to play a role in regulating alternative splicing of the CD44 gene (38). SNPs in cis-acting splicing elements influence alternative splicing. Interestingly, the CD44 rs9666607 G/A variant was predicted to play a role in splicing regulation.

ABCC1, which encodes the ATP-binding cassette, subfamily C, member 1, is a member of the family of ABC transporters (39). These transmembrane proteins play an important role in ATP-dependent transport of lipids, metabolites and drugs. ABC transporters have garnered attention in oncology, as overexpression of such proteins, which efflux chemotherapeutic drugs from cells, has been shown to cause multidrug resistance. In the context of prostate cancer, overexpression of ABCC1 has been shown (40). In addition, CD44$^+$/CD133$^+$ prostate cancer cells exhibiting an increased resistance to cisplatin have been isolated, and the knockdown of increased expression of Notch1 in such cells has been shown to decrease expression of ABCC1 and increase sensitivity to cisplatin (41). More recently, ABC transporters are garnering additional attention, particularly with respect to roles in cancer initiation and progression and transport of lipids that effect oncogenic signaling pathways. Specifically, expression of ABCC1 has been correlated with degree of differentiation and microvascular invasion, tumor size, metastasis and prognosis. The knockdown of ABCC1 has revealed a role in cell proliferation, migration and survival. Substrates of ABCC1 include prostaglandins, leukotrienes and sphingosine-1-phosphate. Consistent with the aforementioned roles of ABCC1, two variants of ABCC1, rs35605 C/T and rs212091 T/C, were found to be associated with prostate cancer survival in the present study. These two ABCC1 variants were predicted to affect specific modes of gene regulation, including splicing and miRNA binding. As in the case of CD44, it is appreciated that dysregulation of alternative splicing can result in the production of alternative or aberrant splice isoforms that have been shown to affect tumorigenesis, including proliferation, apoptosis, angiogenesis, invasion and metastasis. The ABCC1 rs35605 C/T variant was predicted to play a role in splicing regulation. It is also appreciated that microRNAs can function as oncogenes or tumor suppressor genes, mediating expression of target mRNAs playing roles in hypoxia response, cellular proliferation and survival, angiogenesis, metastasis. The ABCC1 rs212091 T/C variant was predicted to affect miRNA-binding site activity, specifically involving hsa-miR-1303. miR-1303 has been shown to be overexpressed in gastric cancer (42). Inhibition of miR-1303 in gastric cancer cell lines resulted in a decrease in proliferation, migration and invasion.

GDF15, which encodes growth/differentiation factor-15, is a cytokine and member of the TGFβ family (43). It has been implicated in stress response, tissue homeostasis and repair, embryonic development, osteogenesis, hematopoiesis and cancer risk and progression. Specific to prostate cancer, elevated expression of GDF15 has been shown in prostatectomy and tumor-adjacent prostate tissues. GDF15 has shown potential as a biomarker for prostate cancer, as increased levels of GDF15 have been detected in serum from metastatic prostate cancer patients, GDF15 serum levels have predicted prostate cancer prognosis and GDF15 is one of seven genes found to discriminate tumor and control urine. Presently, there is conflicting evidence for GDF15 having prostate tumor suppressive and oncogenic activity. In addition, a SNP of GDF15 has been associated with a decreased risk of prostate cancer and an increased risk of death from prostate cancer (44). Consistent with the aforementioned roles of GDF15 as an oncogene and a prognostic factor for prostate cancer, the GDF15 rs1058587 C/G variant was found to be associated with prostate cancer survival in the present study. This variant was predicted to result in an amino acid change in GDF15.

ITGB1, which encodes integrin beta-1, is a member of the integrin family of heterodimeric transmembrane glycoproteins that mediate cell-extracellular matrix interactions (45). In the context of tumor cell biology, integrins mediate proliferation, migration and invasion, survival, metastasis, drug resistance and stemness. Specific to prostate cancer, increased expression of ITGB1 has been shown in prostate cancer biopsy and prostatectomy tissue and in urine exosomes from metastatic prostate cancer patients (46, 47). In addition, ITGB1 has been shown to contribute to prostate cancer cell proliferation, migration and invasion. Moreover, siRNA knockdown of ITGB1 has been shown to increase sensitivity of prostate cancer cells to radiotherapy (48). Consistent with the aforementioned roles of ITGB1, the ITGB1 rs11009151 A/T variant was found to be associated with prostate cancer survival in the present study. This variant was predicted to affect transcription factor binding, specifically involving STAT1, and be linked to expression of ITGB1. Interestingly, STAT1 has been shown to function as a tumor suppressor, activation of STAT1 has been associated with a decrease in CD44+ cells having a stemness phenotype and we have previously identified STAT1 as one of the androgen receptor target genes differentially expressed between African American and white prostate cancer (49, 50).

In conclusion, we have identified SNPs of CD44-related stemness pathway genes that are associated with survival of prostate cancer patients and are predicted to have biological functions. An internal validation procedure, utilizing bootstrap sampling and repeated generation of training and testing sets, demonstrated the utility of the genes we identified beyond the usual prognostic variables. In the future, these results should be confirmed in a larger, prospective study. In addition, associations of these SNPs with prostate cancer survival should be investigated in a racially diverse cohort. The PLCO cohort used here includes 1,150 non-Hispanic white prostate cancer patients and thus prohibited us from identifying SNPs of CD44-related stemness pathway genes and examining their associations with survival of African American prostate cancer patients. Given the higher prostate cancer incidence and mortality in African American men and the more aggressive biology of African American prostate cancer, studies to understand the molecular mechanisms underlying prostate cancer in African American men and to develop associated novel approaches for prevention and treatment that will help reduce prostate cancer disparities for African Americans are urgently needed. Moreover, the functional consequences of the SNPs should be assessed in prostate cancer cells. Furthermore, generation of a cohort with annotated behavioral, social, neighborhood and physiological factors would enable associations of these SNPs with such factors to be evaluated. Our findings that the AUC of the ten-year OS models significantly increased after adding the genetic scores to clinical variables and that in the time-dependent ROC, the cumulative AUC at different time points were greater than the one including only clinical variables suggest that these genetic factors have the potential to serve as novel molecular targets for development of biomarkers of aggressive prostate cancer. In addition, given the aforementioned roles of these CD44-related stemness pathway genes in tumor cell biology, these genetic factors also have the potential to serve as novel molecular targets for developmental therapeutics against aggressive prostate cancer.

REFERENCES FOR EXAMPLE 3

1. Siegel R L, Miller K D, Jemal A. Cancer statistics, 2016. CA Cancer J Clin. 2016; 66(1):7-30.
2. SEER Stat Fact Sheets: Prostate. Available from: http://seer.cancer.gov/statfacts/html/prost.html.
3. Robbins A S, Whittemore A S, Thom D H. Differences in socioeconomic status and survival among white and black men with prostate cancer. American journal of epidemiology. 2000; 151(4):409-16.
4. Crook J, Ots A F. Prognostic factors for newly diagnosed prostate cancer and their role in treatment selection. Semin Radiat Oncol. 2013; 23(3):165-72.
5. Bostrom P J, Bjartell A S, Catto J W, Eggener S E, Lilja H, Loeb S, et al. Genomic Predictors of Outcome in Prostate Cancer. European urology. 2015; 68(6):1033-44.
6. Beck B, Blanpain C. Unravelling cancer stem cell potential. Nature reviews Cancer. 2013; 13(10):727-38.
7. Collins A T, Habib F K, Maitland N J, Neal D E. Identification and isolation of human prostate epithelial stem cells based on alpha(2)beta(1)-integrin expression. Journal of cell science. 2001; 114(Pt 21):3865-72.
8. Richardson G D, Robson C N, Lang S H, Neal D E, Maitland N J, Collins A T. CD133, a novel marker for human prostatic epithelial stem cells. Journal of cell science. 2004; 117(Pt 16):3539-45.
9. Goldstein A S, Lawson D A, Cheng D, Sun W, Garraway I P, Witte O N. Trop2 identifies a subpopulation of murine and human prostate basal cells with stem cell characteristics. Proceedings of the National Academy of Sciences of the United States of America. 2008; 105(52):20882-7.
10. Jiao J, Hindoyan A, Wang S, Tran L M, Goldstein A S, Lawson D, et al. Identification of CD166 as a surface marker for enriching prostate stem/progenitor and cancer initiating cells. PloS one. 2012; 7(8):e42564.
11. Hurt E M, Kawasaki B T, Klarmann G J, Thomas S B, Farrar W L. CD44+ CD24(−) prostate cells are early cancer progenitor/stem cells that provide a model for patients with poor prognosis. Br J Cancer. 2008; 98(4):756-65.

12. Collins A T, Berry P A, Hyde C, Stower M J, Maitland N J. Prospective identification of tumorigenic prostate cancer stem cells. Cancer research. 2005; 65(23):10946-51.
13. Hao J, Madigan M C, Khatri A, Power C A, Hung T T, Beretov J, et al. In vitro and in vivo prostate cancer metastasis and chemoresistance can be modulated by expression of either CD44 or CD147. PloS one. 2012; 7(8):e40716.
14. Kyjacova L, Hubackova S, Krejcikova K, Strauss R, Hanzlikova H, Dzijak R, et al. Radiotherapy-induced plasticity of prostate cancer mobilizes stem-like non-adherent, Erk signaling-dependent cells. Cell Death Differ. 2015; 22(6):898-911.
15. Qin J, Liu X, Laffin B, Chen X, Choy G, Jeter C R, et al. The PSA(−/lo) prostate cancer cell population harbors self-renewing long-term tumor-propagating cells that resist castration. Cell Stem Cell. 2012; 10(5):556-69.
16. Mimeault M, Batra S K. Frequent gene products and molecular pathways altered in prostate cancer- and metastasis-initiating cells and their progenies and novel promising multitargeted therapies. Mol Med. 2011; 17(9-10): 949-64.
17. Al Olama A A, Kote-Jarai Z, Berndt S I, Conti D V, Schumacher F, Han Y, et al. A meta-analysis of 87,040 individuals identifies 23 new susceptibility loci for prostate cancer. Nature genetics. 2014; 46(10):1103-9.
18. Lange E M, Johnson A M, Wang Y, Zuhlke K A, Lu Y, Ribado J V, et al. Genome-wide association scan for variants associated with early-onset prostate cancer. PloS one. 2014; 9(4):e93436.
19. Amin Al Olama A, Kote-Jarai Z, Schumacher F R, Wiklund F, Berndt S I, Benlloch S, et al. A meta-analysis of genome-wide association studies to identify prostate cancer susceptibility loci associated with aggressive and non-aggressive disease. Hum Mol Genet. 2013; 22(2): 408-15.
20. Knipe D W, Evans D M, Kemp J P, Eeles R, Easton D F, Kote-Jarai Z, et al. Genetic variation in prostate-specific antigen-detected prostate cancer and the effect of control selection on genetic association studies. Cancer epidemiology, biomarkers & prevention: a publication of the American Association for Cancer Research, cosponsored by the American Society of Preventive Oncology. 2014; 23(7):1356-65.
21. Kim S, Shin C, Jee S H. Genetic variants at 1q32.1, 10q11.2 and 19q13.41 are associated with prostate-specific antigen for prostate cancer screening in two Korean population-based cohort studies. Gene. 2015; 556(2):199-205.
22. Borque A, del Amo J, Esteban L M, Ars E, Hernandez C, Planas J, et al. Genetic predisposition to early recurrence in clinically localized prostate cancer. BJU international. 2013; 111(4):549-58.
23. San Francisco I F, Rojas P A, Torres-Estay V, Smalley S, Cerda-Infante J, Montecinos V P, et al. Association of RNASEL and 8q24 variants with the presence and aggressiveness of hereditary and sporadic prostate cancer in a Hispanic population. J Cell Mol Med. 2014; 18(1):125-33.
24. Reinhardt D, Helfand B T, Cooper P R, Roehl K A, Catalona W J, Loeb S. Prostate cancer risk alleles are associated with prostate cancer volume and prostate size. The Journal of urology. 2014; 191(6):1733-6.
25. Lin H Y, Amankwah E K, Tseng T S, Qu X, Chen D T, Park J Y. SNP-SNP interaction network in angiogenesis genes associated with prostate cancer aggressiveness. PloS one. 2013; 8(4):e59688.
26. Berndt S I, Wang Z, Yeager M, Alavanja M C, Albanes D, Amundadottir L, et al. Two susceptibility loci identified for prostate cancer aggressiveness. Nat Commun. 2015; 6:6889.
27. Andriole G L, Crawford E D, Grubb R L, 3rd, Buys S S, Chia D, Church T R, et al. Prostate cancer screening in the randomized Prostate, Lung, Colorectal, and Ovarian Cancer Screening Trial: mortality results after 13 years of follow-up. Journal of the National Cancer Institute. 2012; 104(2):125-32.
28. Yeager M, Orr N, Hayes R B, Jacobs K B, Kraft P, Wacholder S, et al. Genome-wide association study of prostate cancer identifies a second risk locus at 8q24. Nature genetics. 2007; 39(5):645-9.
29. Xu Z, Taylor J A. SNPinfo: integrating GWAS and candidate gene information into functional SNP selection for genetic association studies. Nucleic acids research. 2009; 37 (Web Server issue): W600-5.
30. Boyle A P, Hong E L, Hariharan M, Cheng Y, Schaub M A, Kasowski M, et al. Annotation of functional variation in personal genomes using RegulomeDB. Genome research. 2012; 22(9):1790-7.
31. Wacholder S, Chanock S, Garcia-Closas M, El Ghormli L, Rothman N. Assessing the probability that a positive report is false: an approach for molecular epidemiology studies. Journal of the National Cancer Institute. 2004; 96(6):434-42.
32. Howie B N, Donnelly P, Marchini J. A flexible and accurate genotype imputation method for the next generation of genome-wide association studies. PLoS genetics. 2009; 5(6):e1000529.
33. Aulchenko Y S, Ripke S, Isaacs A, van Duijn C M. GenABEL: an R library for genome-wide association analysis. Bioinformatics. 2007; 23(10):1294-6. 34. Akaike H. A new look at the statistical model identification. Automatic Control, IEEE Transactions on 196. 1974: 716-23.
35. Chambless L E, Diao G. Estimation of time-dependent area under the ROC curve for long-term risk prediction. Stat Med. 2006; 25(20):3474-86.
36. Stranger B E, Montgomery S B, Dimas A S, Parts L, Stegle O, Ingle C E, et al. Patterns of cis regulatory variation in diverse human populations. PLoS genetics. 2012; 8(4):e1002639.
37. Ponta H, Sherman L, Herrlich P A. CD44: from adhesion molecules to signalling regulators. Nature reviews Molecular cell biology. 2003; 4(1):33-45.
38. Clark E L, Coulson A, Dalgliesh C, Rajan P, Nicol S M, Fleming S, et al. The RNA helicase p68 is a novel androgen receptor coactivator involved in splicing and is overexpressed in prostate cancer. Cancer research. 2008; 68(19):7938-46.
39. Fletcher J I, Haber M, Henderson M J, Norris M D. ABC transporters in cancer: more than just drug efflux pumps. Nature reviews Cancer. 2010; 10(2):147-56.
40. Karatas O F, Guzel E, Duz M B, Ittmann M, Ozen M. The role of ATP-binding cassette transporter genes in the progression of prostate cancer. The Prostate. 2016; 76(5): 434-44.
41. Liu C, Li Z, Bi L, Li K, Zhou B, Xu C, et al. NOTCH1 signaling promotes chemoresistance via regulating ABCC1 expression in prostate cancer stem cells. Mol Cell Biochem. 2014; 393(1-2):265-70.

42. Zhang S J, Feng J F, Wang L, Guo W, Du Y W, Ming L, et al. miR-1303 targets claudin-18 gene to modulate proliferation and invasion of gastric cancer cells. Dig Dis Sci. 2014; 59(8):1754-63.
43. Vanhara P, Hampl A, Kozubik A, Soucek K. Growth/differentiation factor-15: prostate cancer suppressor or promoter? Prostate Cancer Prostatic Dis. 2012; 15(4): 320-8.
44. Hayes VM, Severi G, Southey M C, Padilla E J, English D R, Hopper J L, et al. Macrophage inhibitory cytokine-1 H6D polymorphism, prostate cancer risk, and survival. Cancer epidemiology, biomarkers & prevention: a publication of the American Association for Cancer Research, cosponsored by the American Society of Preventive Oncology. 2006; 15(6):1223-5.
45. Seguin L, Desgrosellier J S, Weis S M, Cheresh D A. Integrins and cancer: regulators of cancer stemness, metastasis, and drug resistance. Trends Cell Biol. 2015; 25(4):234-40.
46. Kurozumi A, Goto Y, Matsushita R, Fukumoto I, Kato M, Nishikawa R, et al. Tumor-suppressive microRNA-223 inhibits cancer cell migration and invasion by targeting ITGA3/ITGB1 signaling in prostate cancer. Cancer science. 2016; 107(1):84-94.
47. Bijnsdorp I V, Geldof A A, Lavaei M, Piersma S R, van Moorselaar R J, Jimenez C R. Exosomal ITGA3 interferes with non-cancerous prostate cell functions and is increased in urine exosomes of metastatic prostate cancer patients. J Extracell Vesicles. 2013; 2.
48. Broustas C G, Lieberman HB. RAD9 enhances radioresistance of human prostate cancer cells through regulation of ITGB1 protein levels. The Prostate. 2014; 74(14): 1359-70.
49. Bonuccelli G, Castello-Cros R, Capozza F, Martinez-Outschoorn U E, Lin Z, Tsirigos A, et al. The milk protein alpha-casein functions as a tumor suppressor via activation of STAT1 signaling, effectively preventing breast cancer tumor growth and metastasis. Cell Cycle. 2012; 11(21):3972-82.
50. Wang B D, Yang Q, Ceniccola K, Bianco F, Andrawis R, Jarrett T, et al. Androgen receptor-target genes in african american prostate cancer disparities. Prostate cancer. 2013; 2013:763569.

EXAMPLE 4

Much evidence suggests that cells having a stemness phenotype play a pivotal role in oncogenesis, and prostate cells having this phenotype, characterized by self-renewal and pluripotency have been identified. We hypothesize that genetic variants of stemness-related genes contribute to racial disparities in prostate cancer (PCa) incidence. We used two genomewide association study (GWAS) datasets of African descent from the Multiethnic/Minority Cohort Study of Diet and Cancer (MEC) and the Ghana Prostate Study and two GWAS datasets of non-Hispanic whites from the Prostate, Lung, Colorectal and Ovarian (PLCO) Cancer Screening Trial and the Breast and Prostate Cancer Cohort Consortium (BPC3) to test our hypothesis. We evaluated associations of single nucleotide polymorphisms (SNPs) in 25 PCa-related stemness pathway genes with PCa risk in 1,609 cases and 2,550 controls of non-Hispanic whites (4,934 SNPs) and 1,144 cases and 1,116 controls of African descent (5,448 SNPs) with false discovery rate≤0.2. We identified 32 SNPs in five genes that were significantly associated with PCa risk, of which six SNPs in three genes (TP63, ALDH1A1 and WNT1) and eight EGFR SNPs showed heterogeneity between the two populations. Bioinformatics analysis revealed that EGFR rs2072454 and linkage disequilibrium SNPs of the identified SNPs in MET and ALDH1A1 (r2>0.6) are predicted to play a role in RNA splicing regulation. Furthermore, the rs116458171A allele correlated with lower MET mRNA expression in Africans and the rs2072454C allele correlated with higher EGFR mRNA expression in Europeans. These variants may serve as novel biomarkers for disparity in PCa risk.

Summary

SNPs in TP63, ALDH1A1, WNT1 and EGFR were associated with prostate cancer risk and showed heterogeneity between African descent and non-Hispanic white. Some of them were predicted to be functional, playing roles in RNA splicing and transcriptional regulation.

Introduction

Prostate cancer is the second most common cancer in men worldwide (1). In the US, prostate cancer has surpassed lung cancer as the most commonly diagnosed cancer and is the second leading cause of cancer-related deaths in men (2). It is estimated that approximately one man in seven will be diagnosed with prostate cancer in 2015 (2).

Racial, ethnic and geographic disparities of prostate cancer have been observed in large population-level studies (1-3). Notably, African Americans (AAs) have the highest rate of prostate cancer and prostate cancer in patients of African descent often exhibits a more aggressive phenotype (3). Specifically, according to the Surveillance, Epidemiology, and End Results Program (SEER) dataset in the US, the age-adjusted rate of prostate cancer was 203.5 per 100,000 among AA men versus 121.9 per 100,000 among white men for the period between 2009 and 2013 (3). Studies focusing on prostate cancer patients of African-descent have indicated that disparities in both incidence and mortality persist even after controlling for factors associated with social determinants of health and access to care (4).

Though the mechanisms underlying prostate cancer disparities largely remain to be identified, high-throughput DNA sequencing has begun to elucidate a genomic landscape of cancer traits in recent years (5, 6). In the context of this progress, it is likely that disparities in cancer incidence and mortality could be attributed to the diversity in the genome (7, 8). For example, recent genome-wide association studies (GWASs) have identified more than a hundred independent loci associated with prostate cancer susceptibility (9). Approximately half of the risk factors for prostate cancer could be linked to inherited genetic factors (10). The GWAS-identified loci provide partial evidence for cancer risk assessment in the general population and have the potential to pave the way toward precision approaches for early detection and prevention of cancer (11, 12). Among these studies, a few have been undertaken in populations of African descent, and most validation studies of susceptibility loci have not been consistent across different races and ethnicities (13-16). Therefore, studies in different racial and ethnic populations are needed to reveal the diverse etiology of prostate cancer and the mechanisms underlying the observed disparities in genetic susceptibility to prostate cancer.

For many years, clinical screening tests for prostate cancer have provided approaches to detect the disease at an early stage (17, 18). Two large population-based randomized trials, the Prostate, Lung, Colorectal and Ovary (PLCO) and European Randomized Screening for Prostate Cancer (ER-SPC), have demonstrated that digital rectal examination (DRE) and prostate-specific antigen (PSA) blood testing can improve the efficacy of prostate cancer screening (17, 18).

However, concerns that the PSA screening test has contributed to overtreatment remain a topic of ongoing controversy. It is reported that men with low PSA values still have a significant chance of having prostate cancer (19). Despite these challenges, the PSA blood test is still the most widely used early detection method for prostate cancer (19).

PSA is expressed and secreted by the luminal cells in the prostate and, in addition to being routinely used for prostate cancer detection, also serves as a differentiation marker and an indicator of recurrence following treatments (20). However, prostate cancer is heterogeneous, exhibiting divergent morphological and histopathological phenotypes (8, 19). Subpopulations of prostate cancer cells that have a lower or negative PSA level have been identified in high-grade, recurrent or metastatic tumors (21). Such subpopulations of cells that have been identified in castration-resistant prostate cancer exhibit a stemness phenotype, with preferential expression of stem cell markers, such as CD44, integrin α2 and ALDH1A1 (21). Cells having a stemness phenotype are thought to contribute to the development of malignant disease, characterized by self-renewal and generation of heterogeneous cell populations (22). Notably, these cells have the potential to contribute to driving cancer initiation, progression and metastasis. For example, CD133+/α2β1hi cells isolated from benign prostatic neoplasm have been shown to exhibit a molecular profile that is shared with embryonic stem cells (23). About 0.1% of CD44+/α2β1hi/CD133+ prostate cancer cells have shown self-renewal ability with high differentiation (23).

Given the evidence that cells exhibiting a stemness phenotype contribute to oncogenesis, we hypothesize that genetic variants in stemness pathway genes are associated with prostate cancer risk. In the present study, we explored associations of genetic variants in prostate cancer-related stemness pathway genes with prostate cancer risk using four published GWASs in two racial groups, Africans and non-Hispanic whites, to identify mechanisms underlying disparities in susceptibility to prostate cancer.

Materials and Methods

Study Populations

The present study included a total of 2,753 prostate cancer patients and 3,666 controls representing two populations, men of African descent and non-Hispanic white men, from four studies (Table 15 and 16). Specifically, there were 1,609 non-Hispanic white cases and 2,550 non-Hispanic white controls, of which 1,150 cases and 1,101 controls were from The Prostate, Lung, Colorectal and Ovary (PLCO) screening trial and 459 cases and 1,449 controls were from the Breast and Prostate Cancer Cohort Consortium (BPC3). For populations of African descent, the present study had 1,144 cases and 1,116 controls, including 670 cases and 658 controls from the African Americans in the Multiethnic Cohort Study of Diet and Cancer (MEC) and 474 cases and 458 controls from the Africans in the Ghana Prostate study.

The PLCO study is a NCI-funded multicenter randomized screening trial for cancer done in ten medical centers in the US between 1993 and 2011. The PLCO trial has enrolled 77,500 men and 77,500 women aged 55 to 74 (17) and collected blood samples and baseline information during the first screening visit and has followed each participant for at least 13 years after enrollment (24). (24) Genomic DNA extracted from the blood samples was used for GWAS and genotyped with Illumina HumanHap300v1.1 and HumanHap250Sv1.0 (dbGaP accession: phs000207.v1.p1) (25,26). There were 1,150 cases and 1,101 controls included in the present study.

The BPC3 Consortium was established to collect resources from 10 large prospective cohorts to conduct studies on inherited genetic variation, gene-gene and gene-environment interactions in cancer etiology (27). All prostate cancer cases within this Consortium had either a high histologic grade (Gleason score≥8) or extraprostatic extension (Stage C/D) with histopathological confirmation. Genomic DNA extracted from the blood samples was also used in GWAS and genotyped with Illumina Human 610-Quad (dbGaP accession: phs000812.v1.p1) (25). The genotype datasets of the BPC3 study from dbGaP consists of three studies: PLCO, the Alpha-Tocopherol, Beta-Carotene (ATBC) Study, and the Health Professionals Follow-up Study (HPFS) (27). After removal of those duplicated individuals from PLCO, the present study included two subgroups from BPC3: 245 cases and 1,245 controls from ATBC and 214 cases and 204 controls from HPFS.

The Ghana Prostate Study was designed to assess risk factors and biomarkers of prostate cancer in Ghanaian men (15). The study has two components, including a clinical component to recruit prostate cancer cases in Accra, the capital of Ghana, and a population screening survey component to estimate the prevalence of prostate cancer in the Accra male population (15). The cases and controls used for GWAS were selected from these two components. Genomic DNA extracted from the blood samples was genotyped with Illumina HumanOmni5-Quad (dbGaP accession: phs000838.v1.p1) (15, 25). After quality control, 474 cases and 458 controls were eligible for GWAS analysis.

The MEC study was established in Hawaii and Los Angeles between 1993 and 1996 to explore the relationship among diet and other lifestyle factors and cancer (18, 28). The MEC study of more than 215,000 men and women aged 45 to 75 years at recruitment includes primarily African Americans, Japanese, Latinos, Native Hawaiians, and Caucasians. Between 1993 and 1996, each of the enrolled individuals completed a 26-page mailed questionnaire that contained demographic information and medical information (18, 28). Institutional Review Boards at the University of Southern California and the University of Hawaii approved the study protocol. Incident cases of prostate cancer were identified by linkage to the SEER cancer registries in California and Hawaii (18, 28). For the present study, 670 prostate cancer cases and 685 controls of African descent were included. Genomic DNA of each group was used for GWAS and genotyped by Illumina Human660W-Quad_v1_A and Human1M-Duov3_B (dbGaP accession: phs000306.v3. pl) (18, 25, 28).

Gene and SNP Selection

A list of 25 sternness-related genes (Table 17) in prostate cancer was collected according to the online dataset GeneCards, http://http://www.genecards.org// using the search terms "prostate cancer stem cell." Genotyped SNPs within these genes and their ±2-kb flanking regions were selected for association analysis. Genotype imputation was performed with IMPUTE2 for each study according to the matched population from the 1000 Genomes Project Phase 3 (29). Imputed SNPs with info value≥0.8 were qualified for further analysis. As a result, there were 8,609, 8,600, 13,765, and 13,845 SNPs in the aforementioned 25 genes from populations of the PLCO, BPC3, Ghana and MEC studies, respectively. After filtering with minor allele frequency (MAF)≥0.05, genotyping call rate≥95% and Hardy-Weinberg equilibrium (HWE)≥10-5, there were 5,239, 5,345, 6,267, and 6,549 common SNPs from PLCO, BPC3, Ghana and MEC, respectively. For European populations, 4,934 common SNPs were included for both PLCO and BPC3. For populations of African descent, 5,448 common SNPs were included for both Ghana and MEC. Potential functional annotations of the SNPs were predicted using three online tools: SNPinfo, RegulomeDB, and HaploReg. SNPinfo (https://snpinfo.niehs.nih.gov/snpinfo/snpfunc.htm) incorporates functional predictions of protein structure, gene regulation, RNA splicing, and microRNA binding. RegulomeDB (http://www.regulomedb.org/) annotates SNPs with regulatory elements mainly in non-coding regions, which are summarized from the ENCODE project, and published literature. HaploReg v4.1 (http://archive.broadinstitute.org/mammals/haploreg/haploreg.php) shares similar data sources with RegulomeDB and provides specific annotations including eQTLs from GTEx and GEUVADIS.

Statistical Analysis

In each study, principal components (PCs) were calculated using Genome-wide Complex Trait Analysis (GCTA) on the linkage disequilibrium (LD)-pruned subset of the whole-genome typed dataset (30). The first 20 PCs were analyzed for their association with prostate cancer risk by univariate logistic regression analysis. Those with significant associations were included as covariates for the analyses between SNPs and prostate cancer risk. For each SNP, odd ratios (ORs) and their 95% confidence intervals (95% CIs) were estimated by unconditional logistic regression of case/control groups with adjustment for age and PCs using PLINK. In each population, the overall estimates of the SNPs presented in both studies were calculated using meta-analysis in fixed-effects models, if no heterogeneity or random-effects models, if heterogeneities exist. Cochran's Q statistics and I2 were used to assess the heterogeneity. The false discovery rate (FDR) approach was used as the multiple testing corrections to reduce the probability of false-positive findings (31). To test the heterogeneity between non-Hispanic whites and populations of African descent, the SNP with a Q-test P≤0.100 or I2>50.0% was considered as heterogeneous. The I2 index of 25%, 50%, and 75% would be considered low, medium, and high heterogeneity, respectively (32). Pairwise LD was estimated by using the data from the 1000 Genomes Project Phase 3 of the matched population reference (http://www.1000genomes.org/). The correlations between SNPs and corresponding mRNA expression levels were calculated by using a linear regression model in R software. Gene expression levels were obtained from the HapMap 3 project (https://hapmap.ncbi.nlm.nih.gov/) using Illumina Human-6 v2 Expression BeadChip, including 107 Northern Europeans from Utah (CEU) and 326 Africans (AFR)] (33). Statistical analyses were carried out by R (version 3.3.1), SAS (version 9.1.3; SAS Institute, Cary, N.C., USA) and PLINK (version 1.07), unless otherwise specified.

Results

Basic Characteristics of the Study Populations

The study flowchart is shown in FIG. 4. The overall analysis included 2,753 prostate cancer cases and 3,666 controls in non-Hispanic white and African descent populations from four studies (Tables 15 and 16). Distribution of age was statistically different between cases and controls (P<0.001), with the control group being older than the case group (≥70 years: 58.5% versus 43.8%). The additional details regarding different racial and ethnic groups from the four studies are presented in Table 16. To detect the population stratification, we calculated the first 20 PCs in each study and analyzed their association with prostate cancer risk (Table 18). The PCs with significance were selected as covariates included in the models to reduce effects caused by population stratification. Therefore, age and PCs were adjusted for any confounding effects in the following multivariate logistic regression analysis.

Figure 9A:
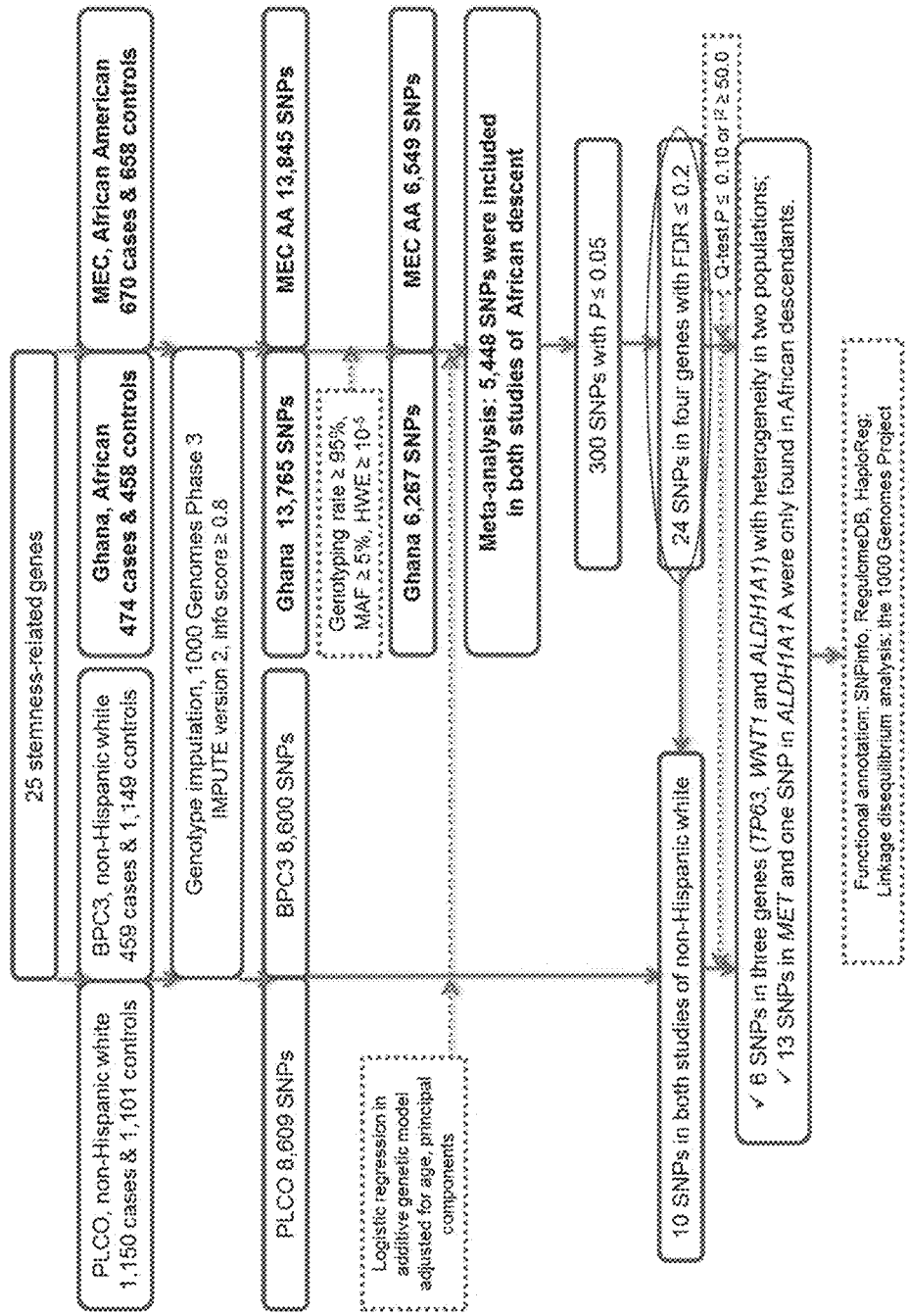
FIG. 9A Research flowchart to identify top SNPs in African descendants.
Figure 9B:
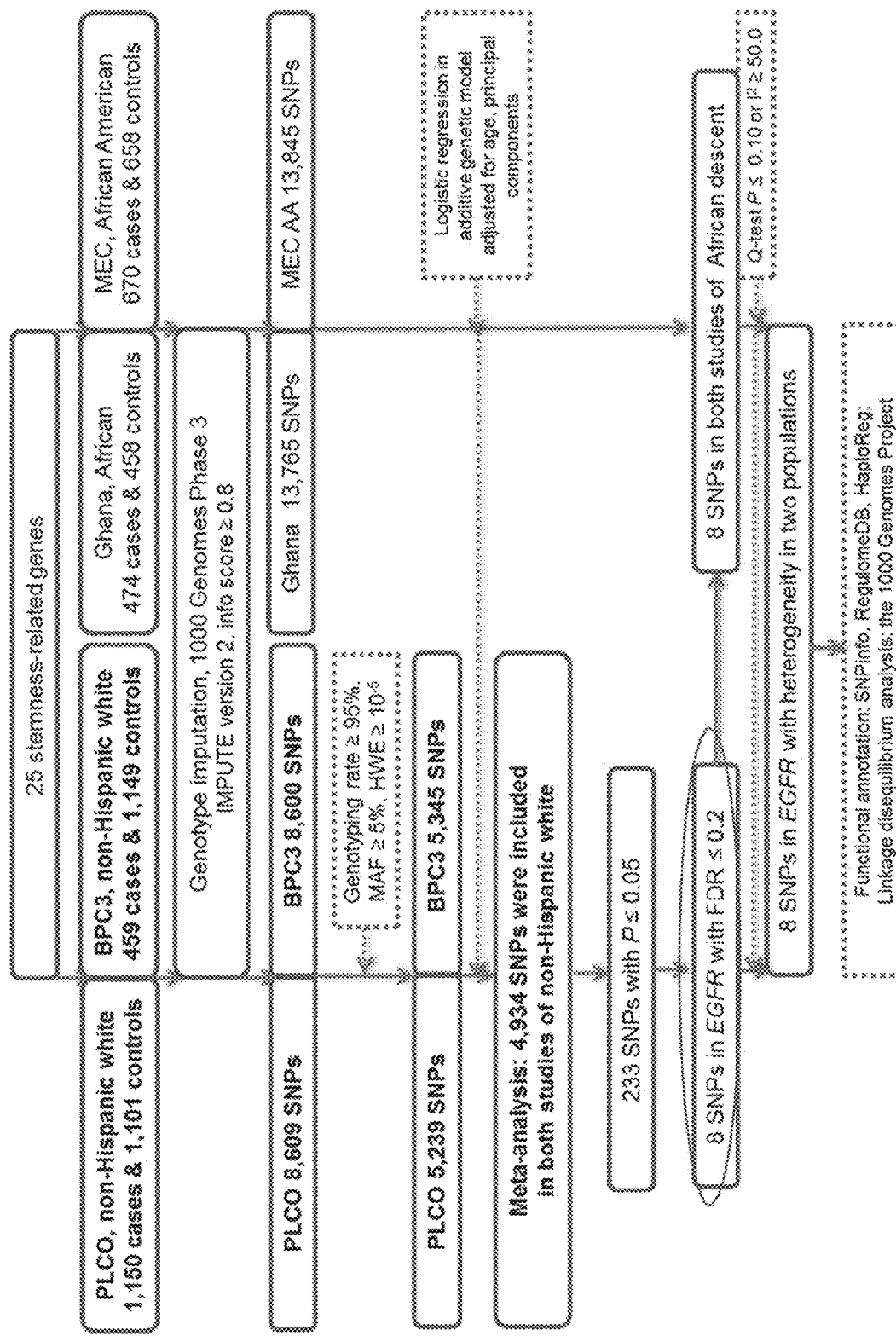
FIG. 9B Research flowchart to identify top SNPs in non-Hispanic whites and heterogeneity between the two racial populations.

Association Analysis of SNPs and Prostate Cancer Risk in Populations of African Descent The workflow of the current study is presented in FIGS. 9A-9B. Considering the allele frequency of each SNP varies between racial and ethnic populations, we separated our analyses into two parts. In the first part, we analyzed the association between common SNPs (MAF≥0.05) and prostate cancer risk in two populations of African descent (FIG. 9A). There were 6,267 and 6,549 common SNPs from the imputed datasets from the Ghana study and the MEC AA study, respectively (FIGS. 10A-10B). A meta-analysis was performed to combine the results of 5,448 overlapped SNPs from the two studies (FIG. 10C). As a result, 300 common SNPs were associated with prostate cancer risk with a P-value≤0.05 in the meta-analysis. For multiple test corrections, 24 SNPs in four genes (8 in TP63, 13 in MET, 2 in ALDH1A1, and 1 in WNT1) reached the FDR≤0.2 (Table 13). Two SNPs in ALDH1A1 were associated with a decreased risk of prostate cancer, whereas the minor alleles of the other 22 SNPs in three genes were all associated with an increased risk of prostate cancer.

Potential functions of these 24 SNPs predicted by three online tools are summarized in Table 19. Most of these SNPs are located in intronic regions of the corresponding genes, except rs149188492, which is located in the 3' untranslated region (UTR) of MET and rs855723, which is located in the 5' upstream region of WNT1. All 24 SNPs are predicted to play a role in transcriptional regulation, including transcription factor binding sites, DNase I hypersensitive sites, promoter histone marks, and enhancer histone marks (Table 14). Among the 13 SNPs of MET, three (rs139335187, rs201395418 and rs5567033632) were in high LD (r2>0.8) with rs13223756 and four (rs5377420134, rs115240747, rs114707545 and rs115293079) were in moderate LD (r2=0.63-0.72) with rs13223756 based on LD data from the 1000 Genomes Phase 3 African population. The rs13223756 SNP is located in an exonic region of MET and predicted to be involved in RNA splicing regulation by SNPinfo. In ALDH1A1, the risk-associated SNPs rs722921 and rs13959 were in moderate LD (r2=0.69) based on the 1000 Genomes Phase 3 population of African descent. ALDH1A1 rs13959 is located in an exonic region and predicted to affect RNA splicing by SNPinfo.

Association Analysis of SNPs and Prostate Cancer Risk in Non-Hispanic Whites

Similar to the previous analysis for populations of African descent, we analyzed the associations of prostate cancer risk and common SNPs in two datasets of non-Hispanic whites, including 5,239 SNPs in the PLCO study and 5,345 SNPs in the BPC3 study (FIGS. 10D-10E). We combined the overlapped 4,934 common SNPs in both studies using a meta-analysis (FIG. 10F). We identified 233 SNPs associated with prostate cancer risk with a P-value≤0.05. Eight SNPs in EGFR remained significant with the FDR≤0.2 and showed an increased risk of prostate cancer. One of these SNPs, rs2072454, is in an exonic region of EGFR, the other seven SNPs of EGFR are located in intronic regions. Functional annotation from the three online tools indicated that rs2072454 was predicted to play a role in RNA splicing and the other intronic variants were predicted to play roles in transcriptional regulation (Table 19).

Heterogeneity of the SNPs Between Populations of African Descent and Non-Hispanic Whites To evaluate potential disparity between populations of African descent and non-Hispanic whites, we calculated the association of the top SNPs and prostate cancer risk in the other populations of case-control comparisons. In the top 24 SNPs of African descent, only 10 were found in non-Hispanic whites from PLCO and BPC3 and the other 14 SNPs (13 in MET and 1 in ALDH1A1) were specific variants of African descent and significantly associated with prostate cancer risk only in men of African descent (Table 13). According to European data from the 1000 Genomes Project and the two non-Hispanic white population datasets in the present study, there was only one allele for these 14 SNPs in European descendants. Of the 24 SNPs, 10 were not validated in non-Hispanic whites and six, in three genes (4 in TP63, 1 in ALDH1A1 and 1 in WNT1) showed moderate to high heterogeneity between the two populations of African descent and non-Hispanic whites (I2=51.2-81.7, Table 14 and Table 20). In contrast, the top eight EGFR SNPs from non-Hispanic whites were not validated in African descendants. Moreover, the eight SNPs showed high heterogeneity between populations of African descent and non-Hispanic whites (all Q-test P<0.100 and I2>75.0, Table 14 and Table 20).

LD Analysis

Figure 11A:
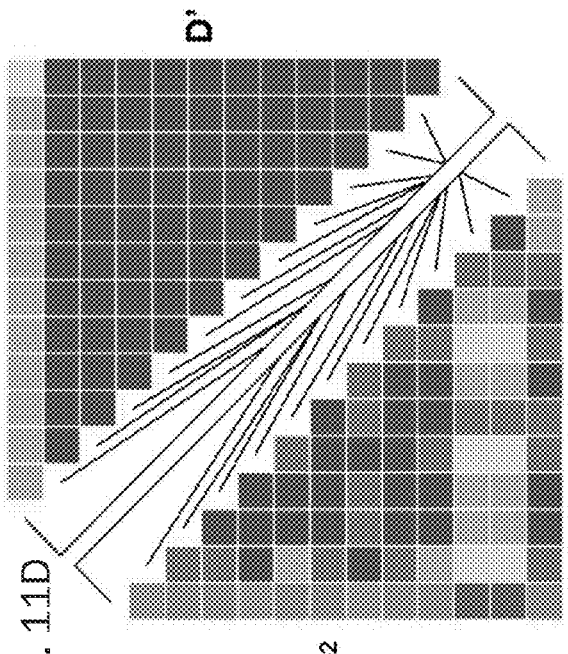
FIG. 11A Overview of the top SNPs in the two racial populations based on the 1000 Genomes Project Phase 3 database. Genome browser of gene regions from UCSC browser (NCBI37/hg19) for TP63.
Figure 11C:
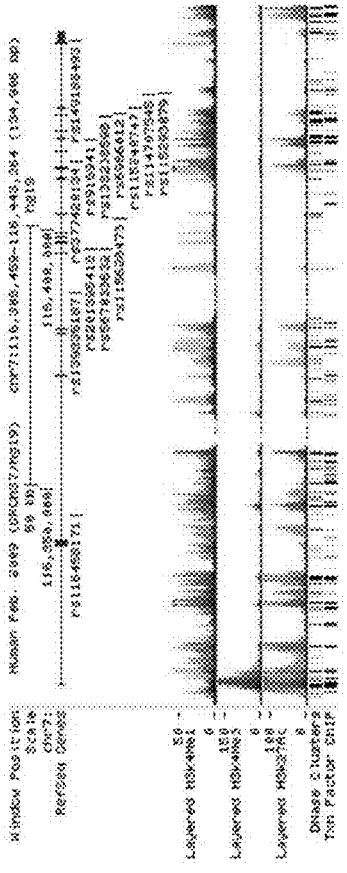
FIG. 11C Overview of the top SNPs in the two racial populations based on the 1000 Genomes Project Phase 3 database. Genome browser of gene regions from UCSC browser (NCBI37/hg19) for MET.
Figure 11B:
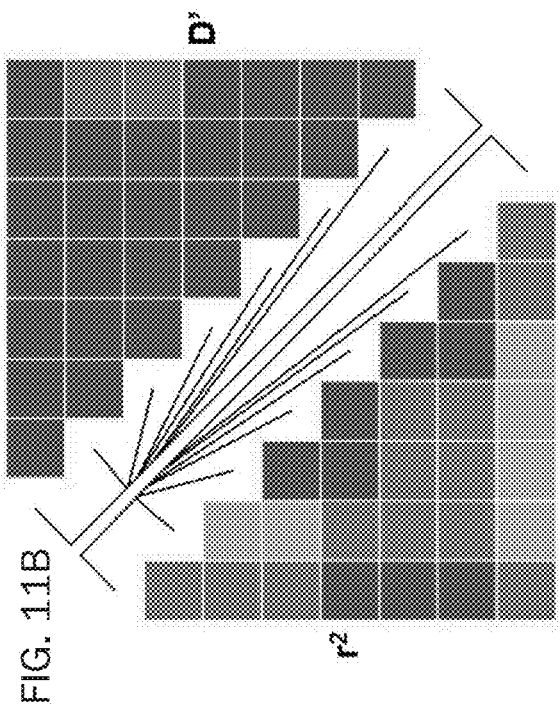
FIG. 11B Linkage disequilibrium (LD) analysis based on the 1000 Genomes Project Phase 3 database in Africans: for 8 SNPs in TP63.
Figure 11D:
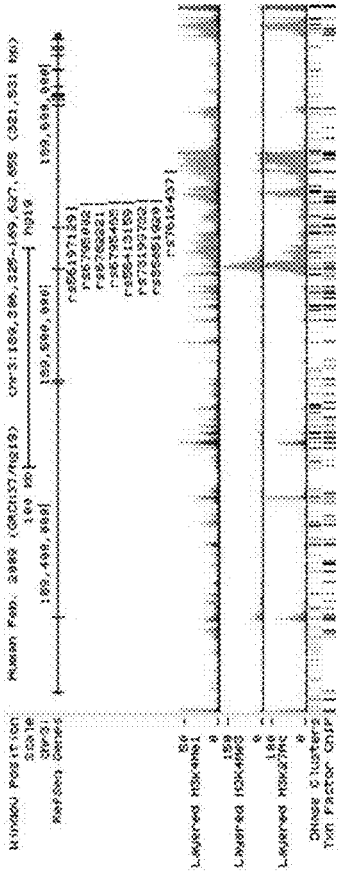
FIG. 11D Linkage disequilibrium (LD) analysis in Africans: for 13 SNPs in MET.
Figure 11E:
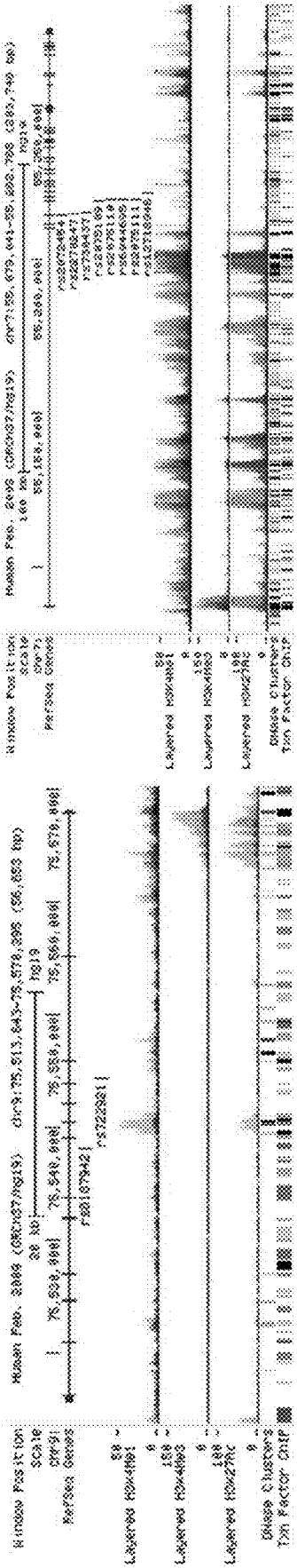
FIG. 11E Overview of the top SNPs in the two racial populations based on the 1000 Genomes Project Phase 3 database. Genome browser of gene regions from UCSC browser (NCBI37/hg19) for ALDH1A1.
Figure 11G:
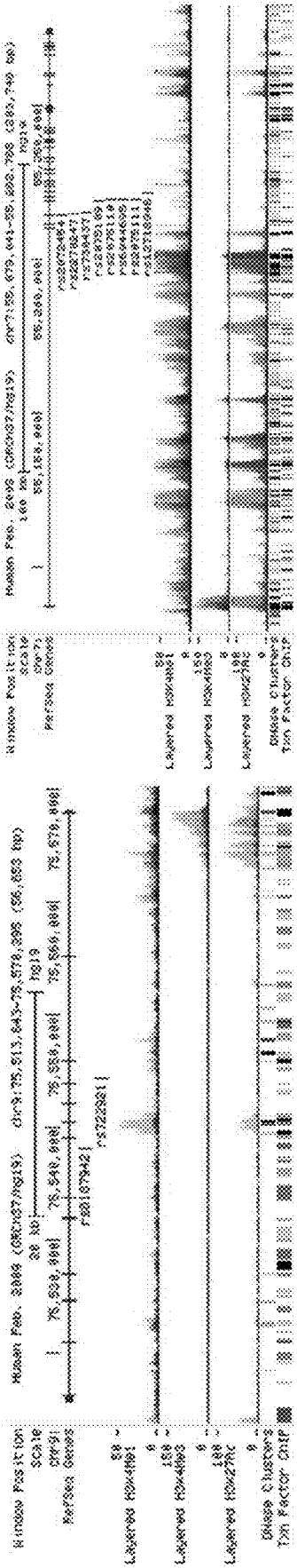
FIG. 11G Overview of the top SNPs in the two racial populations based on the 1000 Genomes Project Phase 3 database. Genome browser of gene regions from UCSC browser (NCBI37/hg19) for EGFR.
Figure 11H:
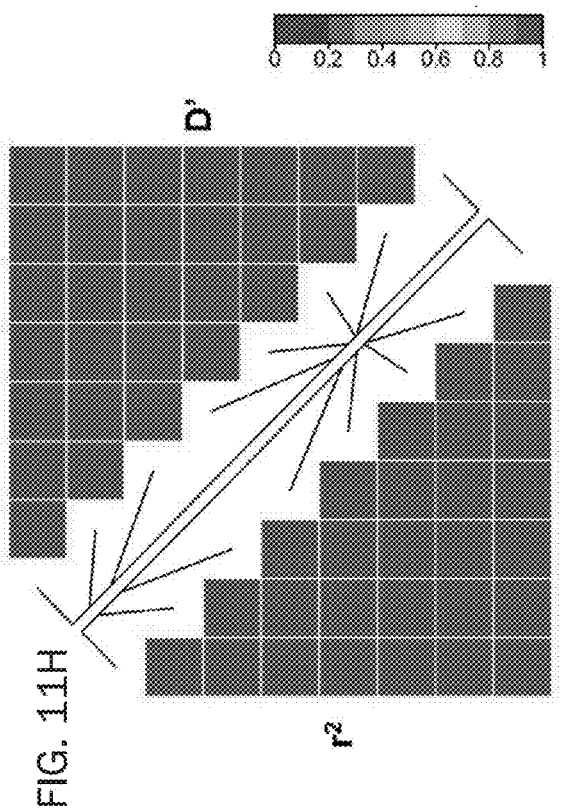
FIG. 11H Linkage disequilibrium (LD) in Europeans for 8 SNPs in EGFR.
Figure 11F:
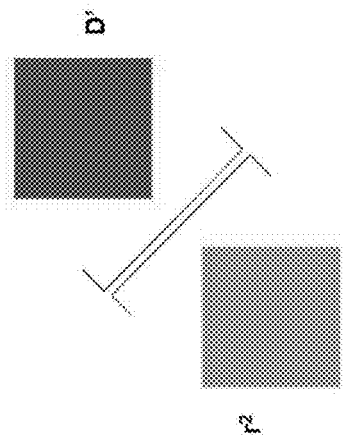
FIG. 11F Linkage disequilibrium (LD) analysis based on the 1000 Genomes Project Phase 3 database in Africans: for 2 SNPs in ALDH1A1.
Figure 12B:
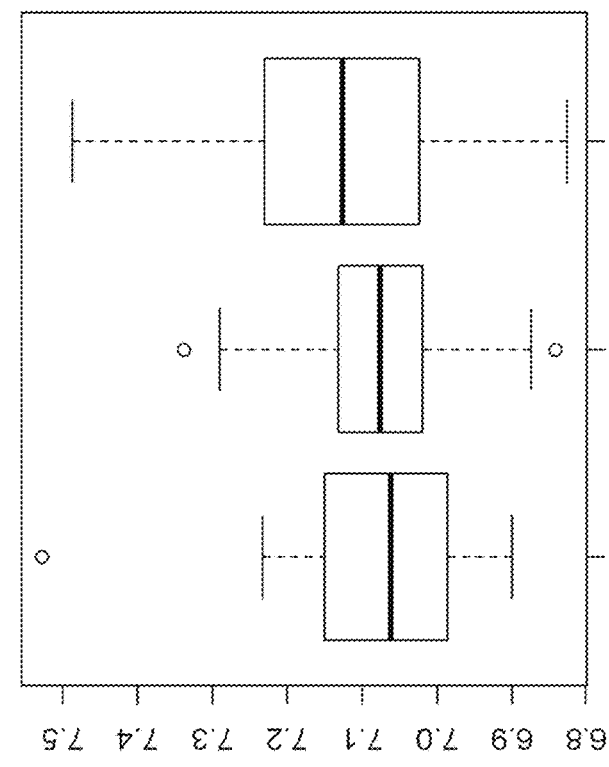
FIG. 12B Correlation between SNPs and their corresponding mRNA expression level in lymphoblastoid cell lines from the HapMap 3 Project. rs2072454 and EGFR mRNA expression level in 107 Europeans.
Figure 12A:
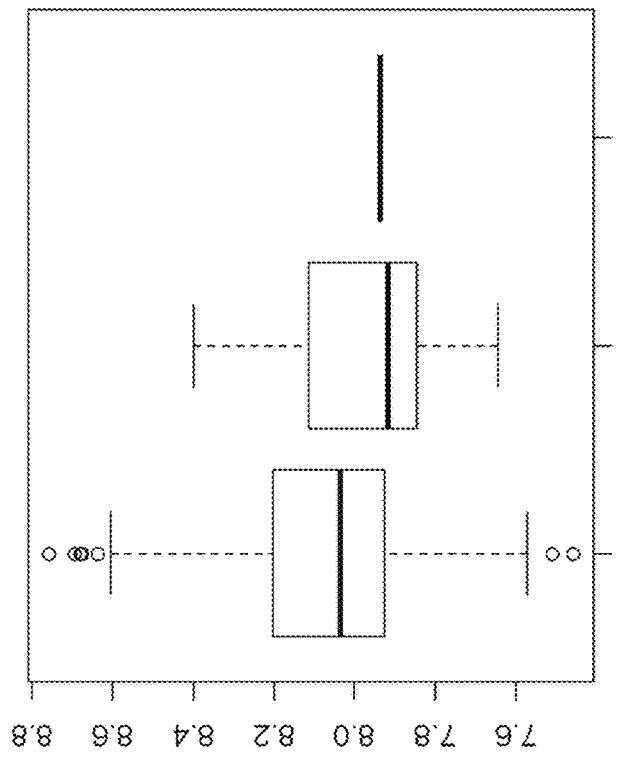
FIG. 12A Correlation between SNPs and their corresponding mRNA expression level in lymphoblastoid cell lines from the HapMap 3 Project. rs116458171 and MET mRNA expression level in 326 Africans.

We further analyzed the LD between the top SNPs that were identified to be associated with prostate cancer risk in the study populations of the two races (i.e. 24 SNPs in four genes of African descent and 8 SNPs in EGFR of non-Hispanic whites). Based on the African reference dataset from the 1000 Genome Project, the eight SNPs in TP63 were all located in the intronic regions and in moderate to high LD (all r2>0.7) (FIG. 11A). In the MET gene, the 12 SNPs also share a moderate to high LD (r2=0.6-1.00), except for the intronic SNP rs116458171 of African descent (FIG. 11B). The two SNPs in ALDH1A1 of African descent were in low LD (r2=0.44) (FIG. 11C). The eight SNPs in EGFR were all in high LD according to the 1000 Genomes European dataset (all r2>0.8) (FIG. 11D). Therefore, we chose the SNPs predicted to have a functional role and exhibiting heterogeneity between populations in each gene based on a threshold of r2=0.6 for the LD analysis. As a result, seven SNPs in five genes (TP63 rs7616437, MET rs114707545, MET rs116458171, ALDH1A1 rs8187942, ALDH1A1 rs72291, WNT1 rs855723, and EGFR r52072454) were selected for further stratified analysis in the study populations of the two races.

Stratified Analysis for Tumor Aggressiveness

We first conducted a subgroup analysis regarding prostate tumor aggressiveness in the available datasets, including MEC for African Americans and PLCO for non-Hispanic whites (Table 21). In six selected SNPs in four genes of African descent, SNPs in TP63, MET, and WNT1 showed risk effects in both non-aggressive and aggressive disease, and two SNPs in ALDH1A1 showed protective effects in both groups in the MEC study. In the PLCO study of non-Hispanic whites, rs2072454 was associated with an increased risk of prostate cancer in both groups. However, no heterogeneity was identified between subgroups of aggressiveness in different races.

Discussion

To determine whether genetic variants in prostate cancer-related sternness pathway genes contribute to prostate cancer susceptibility among different racial groups, we used the genotyping data from published GWASs of two racial groups (populations of African descent and non-Hispanic whites) from Ghana, MEC, PLCO and BPC3 studies. In populations of African descent, we identified a number of SNPs in TP63, MET, and WNT1 that were associated with an increased risk of prostate cancer and SNPs in ALDH1A1 that were associated with a decreased risk. The 13 MET SNPs with over a 1.50-fold increased risk and rs8187942 in ALDH1A1 with a 40% decreased risk were genetic variants only found in populations of African descent. In non-Hispanic whites, SNPs in EGFR were associated with increased risk of prostate cancer. Moreover, we found four SNPs in TP63, one SNP in ALDH1A1, one SNP in WNT1, and eight SNPs in EGFR that showed heterogeneity between populations of African descent and non-Hispanic whites. Regarding predictions of function of the SNPs associated with prostate cancer risk, rs2072454 in EGFR was predicted to be involved in RNA splicing regulation and the risk allele was associated with higher mRNA expression of EGFR. In addition, seven SNPs in MET and one in ALDH1A1 were in moderate to high linkage disequilibrium (LD) (r2>0.6) with the variants in the corresponding genes, and were also predicted to be involved in regulation of RNA splicing.

Eight SNPs in TP63 were significantly associated with prostate cancer risk in men of African descent, four of which showed heterogeneity between African and non-Hispanic white groups. The TP63 gene is a homolog of TP53, a member of the tumor suppressor gene p53 family. Unlike TP53's role as a tumor suppressor, the biological mechanism of TP63 is much more complex because of its various isoforms with antagonistic functions (34). In brief, TP63 encodes two isoforms generated as a result of alternative RNA splicing, TAp63, which contains a Nterminal transactivation (TA) domain functions as a tumor suppressor whereas DNp63, which lacks the TA domain functions as a proto-oncogene (34). DNp63 plays a role in the maintenance of proliferative potential of epidermal progenitor cells, including bladder and prostate epithelial cells (35). The ratio of these TP63 isoforms plays a critical role in monitoring the stem cells in epithelia. It has been reported that overexpressed TP63 can change the ratio of TAp63/DNp63, with a relatively higher expression of DNp63 in tumor tissue compared with that of normal tissue (34). Several SNPs in 3q28 within the TP63 gene region were previously reported to be associated with risk of lung cancer and bladder cancer (36,37).

We also identified SNPs in WNT1 and ALDH1A1 that were risk-associated in African descendants and heterogeneous between the African and non-Hispanic white populations. WNT1 is part of the WNT signaling pathway, which plays crucial roles in cell proliferation, cell migration, cell fate and renewal of stem cells (38). SNP rs855723 was previously reported to be correlated with WNT1 mRNA expression levels in lymphoblastoid cells from Europeans (39). In addition, we confirmed that the rs855723G allele was significantly associated with lower WNT1 mRNA expression level in 107 Europeans from the HapMap 3 project. This variant was predicted to affect transcription factor binding and to be within the CCCTC-Binding Factor (CTCF) binding site by the ENCODE Project chromatin immunoprecipitation sequencing (CHIPseq) data from HaploReg. CTCF is a conserved zinc finger protein implicated in diverse roles in transcriptional activity and chromatin instability (40). Distinct epigenetic patterns including DNA methylation and histone methylation of CTCF binding sites have been documented in benign prostate hyperplasia versus prostate cancer (40).

ALDH1A1 is part of the aldehyde dehydrogenase family, which is involved in intracellular retinoic acid production (41). Aldehyde dehydrogenase performs other functions, including ester hydrolysis, serving as a binding protein for metabolic molecules and potentially functions as an antioxidant, which links to the maintenance of stemness phenotype (41). In particular, one study has shown that ALDH1A1(+) prostate cancer cells exhibit high clonogenic and tumorigenic capacities (42). Moreover, two isoforms of ALDH1A1 generated by alternative RNA splicing were found to be related to different expression levels of the gene in patients with endometrial adenocarcinoma (42). In the present study, a SNP in the exonic region of ALDH1A1 that is predicted to affect alternative RNA splicing is in LD of the SNP we have identified to associate with prostate cancer risk.

MET, also known as hepatocyte growth factor receptor (HGFR), is a proto-oncogenic receptor tyrosine kinase that transduces signals from the extracellular matrix to the cytoplasm (43). A recent study reported that a splice site alteration involving exon 14 in MET was found in multiple cancer types (44). The altered MET has constitutive activity and plays a role in oncogenic transformation (44). In the present study, the identified risk-associated SNPs in MET are in LD with a SNP predicted to play a role in RNA splicing regulation. The SNPs identified here provide novel genetic variation in MET that contributes to prostate cancer risk, enriched in populations of African descent. In addition, the risk allele of rs116458171 was associated with lower mRNA expression of MET, consistent with an oncogenic role in cancer. This variant is located in an intronic region and predicted to play a role in transcription regulation. Taken together, these results indicate that further studies are warranted to elucidate the biological functions of the observed associations.

EGFR rs2072454, located in the coding region, may have an effect on regulation of RNA splicing, as predicted by SNPinfo. EGFR, also known as ERBB1, encodes a well-known transmembrane glycoprotein that is a member of the receptor tyrosine kinase superfamily (45). Growth factors selectively bind to EGFR, triggering intracellular signaling, which ultimately results in cell proliferation (45). The increased expression of EGFR and other growth factors, frequently observed in cancer, causes abnormal proliferation of tumor cells (45). In non-small cell lung cancer, somatic mutations of EGFR are well-recognized markers for targeted cancer therapies (45). Similar to lung cancer, somatic mutations in exons 20 and 21 of EGFR have also been observed in prostate cancer with a highly proliferative and invasive phenotype (46). It has been reported that EGFR overexpression in prostate cancer tissues is significantly more common in men of African American ancestry than white men (47).

Genome-wide analyses of transcriptomes have revealed extensive alternative RNA splicing, which generates enormous biological diversity (48). Specifically, next-generation sequencing data suggest that almost 95% of genes in the human genome undergo alternative RNA splicing (48). During this process, regions of the pre-mRNA are rearranged to generate multiple messenger RNAs that translate into distinct protein isoforms with divergent biological functions (48). The connection between alternative RNA splicing and cancer risk and progression is becoming significantly appreciated because of a considerable number of recent studies that indicate that alternative and aberrant isoforms can activate signaling pathways contributing to oncogenesis (48). The cis-regulatory splicing elements, a part of the regulatory system controlling RNA splicing, consist of exonic and intronic splicing enhancers (ESEs and ISEs) and silencers (ESSs and ISSs). In the present study, EGFR rs2072454 T>C, MET rs13223756, and ALDH1A1 rs13959 (the latter two are in LD with the identified SNPs) were annotated within ESE sequences, as predicted by SNPinfo. Specifically, we found that the rs2072454 C allele was associated with an increased risk of prostate cancer and higher EGFR mRNA expression levels in European populations. These results provide preliminary evidence for a biological mechanism underlying the observed association between the aforementioned SNPs and prostate cancer risk.

Genetic patterns vary across different populations, such as allele frequency of SNPs and LD by haplotype structure (49). Therefore, the heterogeneity in SNPs, haplotypes, and gene-gene interactions could provide broad aspects of genetic diversity in multiple dimensions. In the present study, we have shown that the number of common SNPs in populations of African descent were greater than in non-Hispanic whites. Furthermore, we found that risk-associated SNPs in MET and ALDH1A1 were specific for populations of African descent. In addition to genetic factors, social determinants of health have also been evaluated as contributors to cancer disparities among racial and ethnic groups (49). The gene-environment interaction would plausibly contribute to the disparity between different populations. Studies combining interrogation of genetic variants and social determinants of health are warranted to provide further insight into prostate cancer disparities among racial and ethnic groups and to pave the way toward development of precision risk assessment, detection and treatment of prostate cancer.

In the future, studies using GWAS datasets with larger sample sizes and additional validation analysis as well as incorporating annotation of social determinants of health may provide more extensive evidence for the role of SNPs that regulate alternative splicing in predicting cancer risk among racial and ethnic groups. Low-frequency SNPs with minor allele frequency less than 0.05 were not included in the GWAS datasets used in the present study. Several studies have shown that such rare variants may be responsible for a substantial portion of inherited susceptibility to prostate cancer (50). Additional mechanistic studies are needed to investigate whether SNPs associated with prostate cancer risk and predicted to play a role in RNA splicing regulation in fact affect RNA splicing of the corresponding genes.

Conclusions

In conclusion, using available GWAS data, we analyzed the association between genetic variants in 25 prostate cancer-related stemness pathway genes and prostate cancer risk, providing evidence for disparity of genetic variants in populations of African descent and non-Hispanic whites, including 2,753 cases and 3,666 controls. SNPs in TP63, MET, and WNT1 were found to be associated with increased risk, and SNPs in ALDH1A1 were found to be associated with decreased risk in populations of African descent. SNPs in EGFR were found to be associated with increased risk in non-Hispanic whites. Several SNPs in the aforementioned genes showed heterogeneity between populations of African descent and non-Hispanic whites and were predicted to be functional, playing roles in RNA splicing and transcriptional regulation. Such SNPs may serve as novel biomarkers for prostate cancer risk. Our findings provide new insight into molecular mechanisms underlying racial disparity in prostate cancer risk.

REFERENCES

1. Ferlay, J., et al. (2015) Cancer incidence and mortality worldwide: sources, methods and major patterns in GLOBOCAN 2012. Int J Cancer, 136, E359-86.
2. Siegel, R. L., et al. (2016) Cancer statistics, 2016. CA Cancer J Clin, 66, 7-30.

3. Howlander N, N. A., Krapcho M, Miller D, Bishop K, Altekruse S F, Kosary C L, Yu M, Ruhl J, Tatalovich Z, Mariotto A, Lewis D R, Chen H S, Feuer E J, Cronin K A (eds). SEER Cancer Statistics Review, 1975-2013. National Cancer Institute. Bethesda, Md., http://seer.cancer.gov/csr/1975_2013/.
4. Powell, I. J., et al. (2004) The effect of race/ethnicity on prostate cancer treatment outcome is conditional: a review of Wayne State University data. J Urol, 171, 1508-12.
5. Genomes Project, C., et al. (2012) An integrated map of genetic variation from 1,092 human genomes. Nature, 491, 56-65.
6. Consortium, E. P. (2012) An integrated encyclopedia of DNA elements in the human genome. Nature, 489, 57-74.
7. Jorde, L. B., et al. (2004) Genetic variation, classification and 'race'. Nat Genet, 36, S28-33.
8. Tan, D. S., et al. (2016) Cancer Genomics: Diversity and Disparity Across Ethnicity and Geography. J Clin Oncol, 34, 91-101.
9. Welter, D., et al. (2014) The NHGRI GWAS Catalog, a curated resource of SNP-trait associations. Nucleic Acids Res, 42, D1001-6.
10. Lichtenstein, P., et al. (2000) Environmental and heritable factors in the causation of cancer—analyses of cohorts of twins from Sweden, Denmark, and Finland. N Engl J Med, 343, 78-85.
11. Amin Al Olama, A., et al. (2015) Risk Analysis of Prostate Cancer in PRACTICAL, a Multinational Consortium, Using 25 Known Prostate Cancer Susceptibility Loci. Cancer Epidemiol Biomarkers Prev, 24, 1121-9.
12. Choudhury, A. D., et al. (2012) The role of genetic markers in the management of prostate cancer. Eur Urol, 62, 577-87.
13. Haiman, C. A., et al. (2011) Genome-wide association study of prostate cancer in men of African ancestry identifies a susceptibility locus at 17q21. Nat Genet, 43, 570-3.
14. Chang, B. L., et al. (2011) Validation of genome-wide prostate cancer associations in men of African descent. Cancer Epidemiol Biomarkers Prev, 20, 23-32.
15. Cook, M. B., et al. (2014) A genome-wide association study of prostate cancer in West African men. Hum Genet, 133, 509-21.
16. Haiman, C. A., et al. (2011) Characterizing genetic risk at known prostate cancer susceptibility loci in African Americans. PLoS Genet, 7, e1001387.
17. Andriole, G. L., et al. (2012) Prostate cancer screening in the randomized Prostate, Lung, Colorectal, and Ovarian Cancer Screening Trial: mortality results after 13 years of follow-up. J Natl Cancer Inst, 104, 125-32.
18. Kolonel, L. N., et al. (2004) The multiethnic cohort study: exploring genes, lifestyle and cancer risk. Nat Rev Cancer, 4, 519-27.
19. National Comprehensive Cancer Network. Prostate cancer (Version 2.2016). http://www.nccn.org/professionals/physician_gls/pdf/prostate.pdf.
20. Lilj a, H., et al. (2008) Prostate-specific antigen and prostate cancer: prediction, detection and monitoring. Nat Rev Cancer, 8, 268-78.
21. Qin, J., et al. (2012) The PSA(-/lo) prostate cancer cell population harbors self-renewing long-term tumor-propagating cells that resist castration. Cell Stem Cell, 10, 556-69.
22. Medema, J. P. (2013) Cancer stem cells: the challenges ahead. Nat Cell Biol, 15, 338-44.
23. Collins, A. T., et al. (2005) Prospective identification of tumorigenic prostate cancer stem cells. Cancer Res, 65, 10946-51.
24. Oken, M. M., et al. (2005) Baseline chest radiograph for lung cancer detection in the randomized Prostate, Lung, Colorectal and Ovarian Cancer Screening Trial. J Natl Cancer Inst, 97, 1832-9.
25. Tryka, K. A., et al. (2014) NCBI's Database of Genotypes and Phenotypes: dbGaP. Nucleic Acids Res, 42, D975-9.
26. Yeager, M., et al. (2007) Genome-wide association study of prostate cancer identifies a second risk locus at 8q24. Nat Genet, 39, 645-9.
27. Schumacher, F. R., et al. (2011) Genome-wide association study identifies new prostate cancer susceptibility loci. Hum Mol Genet, 20, 3867-75.
28. Kolonel, L. N., et al. (2000) A multiethnic cohort in Hawaii and Los Angeles: baseline characteristics. Am J Epidemiol, 151, 346-57.
29. Howie, B. N., et al. (2009) A flexible and accurate genotype imputation method for the next generation of genome-wide association studies. PLoS Genet, 5, e1000529.
30. Yang, J., et al. (2011) GCTA: a tool for genome-wide complex trait analysis. Am J Hum Genet, 88, 76-82.
31. Benjamini, Y., et al. (2001) Controlling the false discovery rate in behavior genetics research. Behav Brain Res, 125, 279-84.
32. Higgins, J. P., et al. (2002) Quantifying heterogeneity in a meta-analysis. Stat Med, 21, 1539-58.
33. Stranger, B. E., et al. (2012) Patterns of cis regulatory variation in diverse human populations. PLoS Genet, 8, e1002639.
34. Candi, E., et al. (2007) TAp63 and DeltaNp63 in cancer and epidermal development. Cell Cycle, 6, 274-85.
35. Pignon, J. C., et al. (2013) p63-expressing cells are the stem cells of developing prostate, bladder, and colorectal epithelia. Proc Natl Acad Sci USA, 110, 8105-10.
36. Hu, Z., et al. (2011) A genome-wide association study identifies two new lung cancer susceptibility loci at 13q12.12 and 22q12.2 in Han Chinese. Nat Genet, 43, 792-6.
37. Kiemeney, L. A., et al. (2008) Sequence variant on 8q24 confers susceptibility to urinary bladder cancer. Nat Genet, 40, 1307-12.
38. Anastas, J. N., et al. (2013) WNT signalling pathways as therapeutic targets in cancer. Nat Rev Cancer, 13, 11-26.
39. Lappalainen, T., et al. (2013) Transcriptome and genome sequencing uncovers functional variation in humans. Nature, 501, 506-11.
40. Paradowska, A., et al. (2009) Aberrant epigenetic modifications in the CTCF binding domain of the IGF2/H19 gene in prostate cancer compared with benign prostate hyperplasia. Int J Oncol, 35, 87-96.
41. Marcato, P., et al. (2011) Aldehyde dehydrogenase: its role as a cancer stem cell marker comes down to the specific isoform. Cell Cycle, 10, 1378-84.
42. Mamat, S., et al. (2011) Transcriptional Regulation of Aldehyde Dehydrogenase 1A1 Gene by Alternative Spliced Forms of Nuclear Factor Y in Tumorigenic Population of Endometrial Adenocarcinoma. Genes Cancer, 2, 979-84.
43. Jeffers, M., et al. (1997) Activating mutations for the met tyrosine kinase receptor in human cancer. Proc Natl Acad Sci USA, 94, 11445-50.
44. Frampton, G. M., et al. (2015) Activation of MET via diverse exon 14 splicing alterations occurs in multiple tumor types and confers clinical sensitivity to MET inhibitors. Cancer Discov, 5, 850-9.
45. Ciardiello, F., et al. (2008) EGFR antagonists in cancer treatment. N Engl J Med, 358, 1160-74.
46. Peraldo-Neia, C., et al. (2011) Epidermal Growth Factor Receptor (EGFR) mutation analysis, gene expression profiling and EGFR protein expression in primary prostate cancer. BMC Cancer, 11, 31.
47. Shuch, B., et al. (2004) Racial disparity of epidermal growth factor receptor expression in prostate cancer. J Clin Oncol, 22, 4725-9.
48. Kornblihtt, A. R., et al. (2013) Alternative splicing: a pivotal step between eukaryotic transcription and translation. Nat Rev Mol Cell Biol, 14, 153-65.
49. Rosenberg, N. A., et al. (2015) Genetic Diversity and Societally Important Disparities. Genetics, 201, 1-12.
50. Mancuso, N., et al. (2016) The contribution of rare variation to prostate cancer heritability. Nat Genet, 48, 30-5.

What is claimed is:

1. A method for treating a subject suspected of having an aggressive prostate cancer, the method comprising:
   (i) obtaining a blood sample from a subject having prostate cancer;
   (ii) isolating genomic DNA from the sample;
   (iii) detecting the presence of a C allele at the rs2248490 SNP and a G allele at the rs15736 SNP in the WDR4 gene in the sample, wherein the presence of a C allele at the rs2248490 SNP and a G allele at the rs15736 SNP is associated with aggressive prostate cancer, and;
   (iv) administering to the subject at least one cancer therapy for the treatment of prostate cancer.

2. The method of claim 1, wherein the method further comprises:
   (v) detecting -the allele present at at least one additional SNP in a gene, wherein the at least one additional SNP is rs362708 in the RELN gene.

3. The method of claim 2, wherein the method step of (v) further comprises detecting the allele present at rs3817552 or rs764291 in the MYBPC1 gene.

4. The method of claim 3, wherein the method of step (v) further comprises detecting the allele present at rs8546 in the NCOR2 gene.

5. The method of claim 1, wherein the subject is African American.

6. The method of claim 1, wherein the cancer therapy is selected from the group consisting of chemotherapy, hormone therapy, androgen therapy, radiation, surgery, vaccine therapy, immunotherapy and combinations thereof.

7. The method of claim 4, wherein the method step of (iii) further comprises detecting the allele present at rs11911090 in the WDR4 gene.

8. The method of claim 1, wherein the method step of (iii) comprises detecting the allele present of a SNP at rs3817552 or rs764291 in the MYBPC1 gene.

9. The method of claim 1, wherein the method step of (iii) further comprises detecting the allele present at rs8546 in the NCOR2 gene.

10. The method of claim 1, wherein the method step of (iii) further comprises detecting the allele present at rs3817552 in the MYBPC1 gene.

11. The method of claim 1, wherein the method step of (iii) further comprises detecting the allele present at rs11911090 in the WDR4 gene.

* * * * *

UNITED STATES PATENT AND TRADEMARK OFFICE
CERTIFICATE OF CORRECTION

PATENT NO. : 10,982,285 B2  
APPLICATION NO. : 15/344222  
DATED : April 20, 2021  
INVENTOR(S) : Jennifer Freedman et al.

It is certified that error appears in the above-identified patent and that said Letters Patent is hereby corrected as shown below:

In the Specification

Column 15, Line 8, TABLE 1, "r511651" should be --rs11651--.

Column 15, Line 18, TABLE 2, "r515736" should be --rs15736--.

Column 21, Line 42, "r5218699" should be --rs218699--.

Column 21, Line 43, "r510228436" should be --rs10228436--.

Column 23, Line 31, "r59666607" should be --rs9666607--.

Column 23, Line 31, "r535605" should be --rs35605--.

Column 23, Line 32, "r5212091" should be --rs212091--.

Column 23, Line 32, "r51058587" should be --rs1058587--.

Column 23, Line 32, "r511009151" should be --rs11009151--.

Column 23, Line 55, "sternness" should be --stemness--.

Column 23, Line 64, "sternness" should be --stemness--.

Column 24, Line 28, "sternness" should be --stemness--.

Column 26, Line 51, "r59666607" should be --rs9666607--.

Column 26, Line 50, "RR" should be --HR--.

Signed and Sealed this  
Twenty-second Day of June, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,982,285 B2

Column 29, Line 49, "sternness" should be --stemness--.

Column 29, Line 55, "sternness" should be --stemness--.

Column 29, Line 66, "sternness" should be --stemness--.

Column 30, Line 22, "sternness" should be --stemness--.

Column 33, Line 47, "sternness" should be --stemness--.

Column 33, Line 51, "sternness-related" should be --stemness-related--.

Column 33, Line 61, "sternness" should be --stemness--.

Column 35, Line 19, "a2" should be --α2--.

Column 36, Line 50, "sternness-related" should be --stemness-related--.

Column 37, Line 31, "12" should be --I2--.

Column 37, Line 36, "12" should be --I2--.

Column 37, Line 37, "12" should be --I2--.

Column 38, Line 33, "r5139335187" should be --rs139335187--.

Column 38, Line 34, "r5567033632" should be --rs567033632--.

Column 38, Line 35, "r5377420134" should be --rs377420134--.

Column 39, Line 20, "12" should be --I2--.

Column 39, Line 42, "r52072454" should be --rs2072454--.

Column 39, Line 60, "sternness" should be --stemness--.

Column 42, Line 44, "sternness" should be --stemness--.

Column 43, Line 59, "Lilj a" should be --Lilja--.